United States Patent [19]
Von Langen et al.

[11] Patent Number: 6,048,869
[45] Date of Patent: Apr. 11, 2000

[54] TRICYCLIC COMPOUNDS

[75] Inventors: Derek Von Langen, Fanwood; Susan D. Aster, Teaneck; Donald W. Graham, Mountainside, all of N.J.

[73] Assignee: Merck & Co., Inc., Rahway, N.J.

[21] Appl. No.: 09/360,266

[22] Filed: Jul. 26, 1999

Related U.S. Application Data

[60] Provisional application No. 60/094,521, Jul. 29, 1998.

[51] Int. Cl.$^7$ .......................... A61K 31/47; C07D 221/06
[52] U.S. Cl. .......................... 514/290; 514/248; 514/249; 514/253; 514/256; 514/259; 514/260; 514/272; 514/274; 544/234; 544/238; 544/288; 544/335; 544/336; 544/353; 544/354; 544/408; 546/98; 546/101; 546/110
[58] Field of Search .............................. 514/290; 546/110

[56] References Cited

U.S. PATENT DOCUMENTS

| | | | |
|---|---|---|---|
| 5,239,075 | 8/1993 | Audia et al. | 546/110 |
| 5,495,021 | 2/1996 | Audia et al. | 546/101 |
| 5,541,190 | 7/1996 | Audia et al. | 514/290 |
| 5,550,134 | 8/1996 | Audia et al. | 514/284 |
| 5,574,160 | 11/1996 | Audia et al. | 546/110 |
| 5,578,724 | 11/1996 | Haehl et al. | 544/234 |
| 5,621,104 | 4/1997 | Graham et al. | 546/108 |
| 5,622,961 | 4/1997 | Audia et al. | 514/290 |
| 5,622,962 | 4/1997 | Audia et al. | 514/290 |
| 5,629,007 | 5/1997 | Audia et al. | 424/423 |
| 5,635,197 | 6/1997 | Audia et al. | 424/423 |
| 5,670,514 | 9/1997 | Audia et al. | 514/298 |
| 5,719,158 | 2/1998 | Durette et al. | 514/284 |
| 5,739,137 | 4/1998 | Durette et al. | 514/256 |
| 5,910,497 | 6/1999 | Durette et al. | 514/253 |

FOREIGN PATENT DOCUMENTS

| | | |
|---|---|---|
| 0 532 190 A2 | 3/1993 | European Pat. Off. |
| 0 564 193 A1 | 10/1993 | European Pat. Off. |
| 0 591 582 A1 | 4/1994 | European Pat. Off. |
| 0 591 583 A1 | 4/1994 | European Pat. Off. |
| 0 703 221 A1 | 9/1994 | European Pat. Off. |
| 0 684 234 A1 | 11/1995 | European Pat. Off. |
| 0 733 365 A2 | 9/1996 | European Pat. Off. |
| 0 743 303 A1 | 11/1996 | European Pat. Off. |
| 0 926 148 A1 | 6/1999 | European Pat. Off. |
| WO 98/18757 | 5/1998 | WIPO. |

OTHER PUBLICATIONS

Jones et al., J. Med. Chem., vol. 36 (1993), pp. 421–423, "Nonsteroidal inhibitors of human Type 1 steroid 5–alpha–reductase".

Neubauer et al., Drugs fo the Future, vol. 20 (1995), pp. 144–147, "Type 1 steroid 5–alpha–reductase inhibitor: treatment of androgenic alopecia".

Smith et al., 211th ACS Nat'l Meeting, Mar. 1996, MEDI 154, "Synthesis and 5–alpha–reductase inhibitory activity of benzoquinolinones derived from palladium mediated coupling reactions".

Bakshi et al., J. Med. Chem., vol. 37 (1994), pp. 3871–3874, "4,7beta–Dimethyl–4–azacholestan–3–one (MK–386) and related 4–azateroids as selective inhibitors of human Type I 5–alpha–reductase".

Mook et al., Tetra. Lett., vol. 36 (1995), pp. 3969–3972, "Synthesis of phenanthridin–3–one derivatives: non–Steroidal inhibitors of steroid 5–alpha–reductase".

Hartmann et al., Eur. J. Med. Chem., vol. 29 (1994), pp. 807–817, "Novel 5alpha–reductase inhibitors. Synthesis and structure–activity studies of 5–substituted 1–methyl–2–pyridones and 1–methyl–2–piperidones".

Graham et al., Abstracts of the 218th ACS Nat'l Mtg., New Orleans, LA, Aug. 22–26, 1999, MEDI 6, "Synthesis of potent nonsteroidal tricyclic Type I specific 5alpha–reductase inhibitors".

Smith et al., Bioorg. & Med. Chem. Lett., vol. 8 (1998), pp. 395–398, "Synthesis and 5alpha–reductase inhibitory activity of 8–substitued benzo[f]quinolinones derived from palladium . . . ".

Abell et al., Bioorg. & Med. Chem. Lett., vol. 4 (1994), pp. 1365–1368, "Preparative chiral HPLC separation of all possible steroisomers of LY191704 and LY266111 and their invitro inhibition . . . ".

(List continued on next page.)

Primary Examiner—Evelyn Mei Huang
Attorney, Agent, or Firm—Catherine D. Fitch; Philippe L. Durette; Melvin Winokur

[57] ABSTRACT

The novel compounds of the present invention are those of structural formula I:

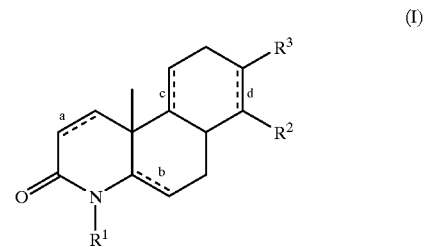

or a pharmaceutically acceptable salt, ester, or stereoisomer thereof, which are inhibitors of 5α-reductase. The compounds of formula I are useful in the oral, systemic, parenteral or topical treatment of hyperandrogenic conditions. Methods of using the compounds of formula I for the treatment of hyperandrogenic conditions such as acne vulgaris, seborrhea, androgenic alopecia, male pattern baldness, female hirsutism, benign prostatic hyperplasia, and the prevention and treatment of prostatic carcinoma, as well as the treatment of prostatitis the treatment of sweat-related conditions such as apocrine gland sweating, hyperhidrosis, and hydradenitis suppurativa, the treatment of polycystic ovary syndrome, the prevention and treatment of bone loss and related diseases, and the prevention and treatment of premature labor are provided, as well as pharmaceutical compositions for the compounds of formula I.

32 Claims, No Drawings

OTHER PUBLICATIONS

Wikel et al., Bioorg. & Med. Chem. Lett., vol. 3 (1993), pp. 1157–1162, "Qsar study of benzoquinolinones as inhibitors of human Type 1 5–alpha–reductase".

Kennedy, J. of Chromatog. A., vol. 725 (1996), pp. 219–224, "Comparison of chiral separations on polysaccharide chiral stationary phases to an improved Pirkle phase".

Anderson et al., J. Org. Chem., vol. 63 (1998), pp. 8224–8228, "Cooperative catalyst effects in palladium – mediated cyanation reactions of aryl halides and triflates".

Audia et al., Tet. Lett., vol. 34 (1993), pp. 7001–7004, "Synthesis of the individual enantiomers of the benzoquinolinone human Type 1 steroid 5–alpha–reductase inhibitors LY191704 and LY266111".

Audia et al., Tet. Lett., vol. 37 (1996), pp. 4121–4124, "A diastereoselective tandem metalloenamine alkylation/ aza–annulation of beta–tetralones expedites the synthesis of benzoquinolinones".

TRICYCLIC COMPOUNDS

CROSS-REFERENCE TO RELATED APPLICATIONS

The present invention is related to U.S. provisional application Ser. No. 60/094,521, filed Jul. 29, 1998, the contents of which are hereby incorporated by reference.

BACKGROUND OF THE INVENTION

The present invention provides novel compounds, novel compositions, methods of their use and methods of their manufacture, where such compounds are generally pharmacologically useful as agents in therapies whose mechanism of action rely on the inhibition of 5α-reductase.

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endocrinol. 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of testosterone-5α-reductase. Inhibitors of testosterone-5α-reductase will serve to prevent or lessen symptoms of hyperandrogenic stimulation in these organs. See especially U.S. Pat. No. 4,377,584, issued Mar. 22, 1983, and U.S. Pat. No. 4,760,071, issued Jul. 26, 1988, both assigned to Merck & Co., Inc.

The enzyme 5α-reductase catalyzes the reduction of testosterone to the more potent androgen, dihydrotestosterone, as shown below:

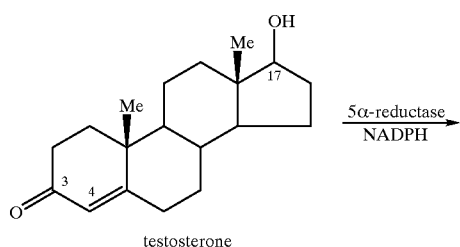
testosterone

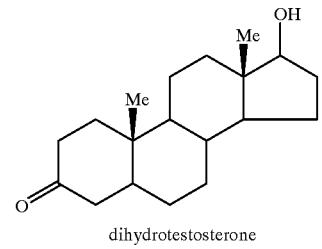
dihydrotestosterone

Finasteride, (17,-(N-tert-butylcarbamoyl)-3-oxo-4-aza-5 α-androst-1-ene-3-one) as shown below, is a potent inhibitor of the human prostate enzyme.

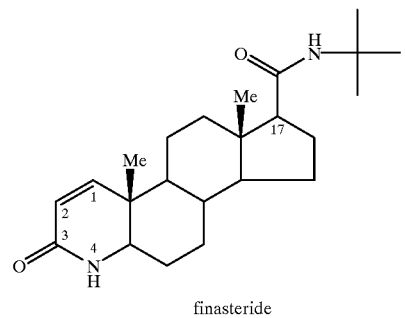
finasteride

Under the trade name PROSCAR®, finasteride is known to be useful in the treatment of hyperandrogenic conditions; see eg. U.S. Pat. No. 4,760,071. Finasteride is currently prescribed for the treatment of benign prostatic hyperplasia (BPH), a condition afflicting to some degree the majority of men over age 55. Under the trade name PROPECIA®, a lower dose of finasteride is prescribed for the treatment of male pattern hair loss. Finasteride's utility in the treatment of androgenic alopecia and prostatic carcinoma is also disclosed in the following documents: EP 0 285,382, published Oct. 5, 1988; EP 0 285,383, published Oct. 5, 1988; Canadian Patent No. 1,302,277; and Canadian Patent No. 1,302,276.

There are two isozymes of 5α-reductase in humans. One isozyme (type 1 or 5α-reductase 1) predominates in sebaceous glands of facial and skin tissue and is relatively insensitive to finasteride (see, e.g., G. Harris, et al., Proc. Natl. Acad. Sci. USA, Vol. 89, pp. 10787–10791 (Nov. 1992)); the other (type 2 or 5α-reductase 2) predominates in the prostate and is potently inhibited by finasteride.

Nonsteroidal type 1 (LY-191704) and type 2 (FK143) 5α-reductase inhibitors have been reported.

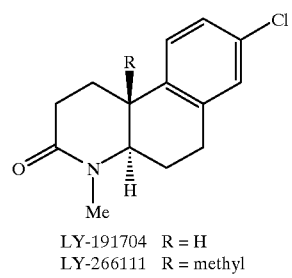
LY-191704 R = H
LY-266111 R = methyl

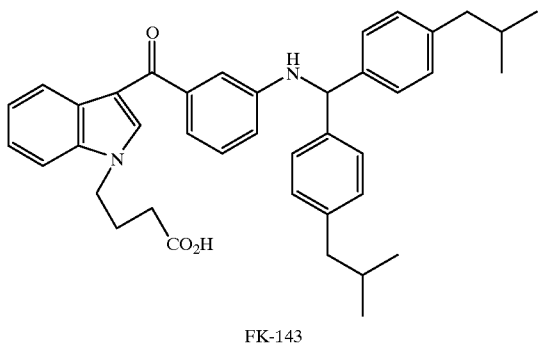

FK-143

Since 5α-reductase and its isozymes convert testosterone to DHT, inhibition of either or both of the isozymes would serve to alleviate the conditions and diseases mediated by DHT. The present invention addresses this by providing novel compounds that are active as inhibitors of 5α-reductase, and particularly provides novel compounds with potent type 1 selective activity.

SUMMARY OF THE INVENTION

The novel compounds of the present invention are those of structural formula I:

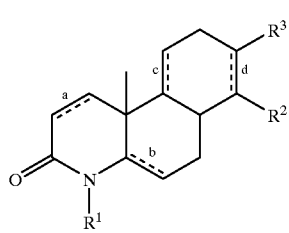
(I)

or pharmaceutically acceptable salts, esters, or stereoisomers thereof, which are inhibitors of 5α-reductase. The compounds of formula I are useful in the oral, systemic, parenteral or topical treatment of hyperandrogenic conditions such as acne vulgaris, seborrhea, androgenic alopecia which includes female and male pattern baldness, female hirsutism, benign prostatic hyperplasia, and the prevention and treatment of prostatic carcinoma, as well as in the treatment of prostatitis, the treatment of sweat-related conditions such as apocrine gland sweating, hyperhidrosis, and hydradenitis suppurativa, the treatment of polycystic ovary syndrome, the prevention and treatment of bone loss and related diseases, and the prevention and treatment of premature labor. The compounds of the present invention may also be useful to raise HDL cholesterol levels.

Therefore, it is an object of this invention to provide compounds that have sufficient activity in the inhibition of 5α-reductase. It is an additional object of this invention to provide methods of using the compounds of formula I for the treatment of hyperandrogenic conditions such as acne vulgaris, seborrhea, androgenic alopecia, male pattern baldness, female hirsutism, benign prostatic hyperplasia, and the prevention and treatment of prostatic carcinoma, as well as the treatment of prostatitis, the treatment of sweat-related conditions such as apocrine gland sweating, hyperhidrosis, and hydradenitis suppurativa, the treatment of polycystic ovary syndrome, the prevention and treatment of bone loss and related diseases, and the prevention and treatment of premature labor. Methods of employing the compounds of formula I to raise HDL cholesterol levels are also provided. Still another object of the present invention is to provide for a method of manufacture of a medicament useful for the treatment of hyperandrogenic condtions. It is a further object of this invention to provide pharmaceutical compositions for the compounds of formula I. Another object of this invention is to provide compounds of formula I in combination with other active agents, for example with finasteride, or a potassium channel opener, such as minoxidil, or a retinoic acid or a derivative thereof, wherein such combinations would be useful in one or more of the above-mentioned methods of treatment or pharmaceutical compositions.

DETAILED DESCRIPTION OF THE INVENTION

The present invention relates to novel compounds of structural formula (I) having the natural steroidal trans-anti-trans relative configuration at the A,B and B,C ring junctures:

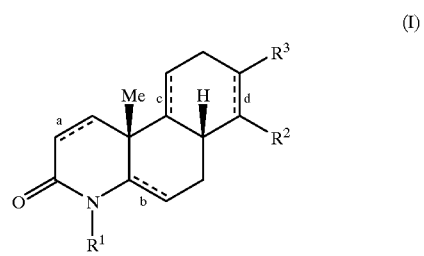
(I)

or a pharmaceutically acceptable salt, ester or stereoisomer thereof.

The bonds designated with dotted lines "a", "b", "c" and "d" may be single bonds or double bonds, provided that when "a" is a double bond, the dotted lines "b", "c" and "d" must represent single bonds; and further provided that when "b" is a double bond, "c" or both "c" and "d" must represent double bonds. In one embodiment of the instant invention "a", "b " and "d" each represent single bonds and "c" represents a double bond. In another embodiment of the present invention are compounds of formula I wherein "a" and "d" each represent single bonds and "b" and "c" each represent double bonds. In yet another embodiment of the instant invention are compounds of formula I wherein "a", "b", "c", and "d" each represent single bonds. In another embodiment of the present invention are compounds of formula I wherein "a" and "b" each represent single bonds and "c" and "d" each represent double bonds. In still another embodiment of the present invention are compounds of structural formula I wherein "b", "c", and "d" each represent single bonds and "a" represents a single bond.

$R^1$ is selected from hydrogen, $C_{1-5}$ alkyl and $CH_2R^5$. In one embodiment of the present invention, $R^1$ is selected from hydrogen and methyl. In one class of the present invention, $R^1$ is hydrogen. In another class of the present invention $R^1$ is methyl.

$R^2$ is selected from: hydrogen, $CO_2R^4$, $CONR_4R^5$,

$COR^5$, $S(O)_nR^5$, $NHCO_2R^4$, $NHCOR^4$, $NHCOR^5$, $CN$, $COSR^5$, $C_{1-5}$ alkyl, and $C_xX_y$. In one embodiment of the present invention, $R^2$ is selected from hydrogen, $CO_2R^4$, $CONR^4R^5$,

$COR^5$, $S(O)_nR^5$, $NHCO_2R^4$, CN, $COSR^5$, methyl, and $C_xX_y$. In another embodiment of the present invention, $R^2$ is selected from: hydrogen, $CO_2R^4$, —$CONR^4R^5$,

$COR^5$, $S(O)_nR^5$, $NHCO_2R^4$, $NHCOR^4$, $NHCOR^5$, CN, $COSR^5$, and $CF_3$. In one class of the present invention, $R^2$ is selected from: hydrogen, methyl, trifluoromethyl-, phenylcarbonyl-, carboxyl-, methoxycarbonyl-, ethoxycarbonyl-, t-butoxycarbonyl-, 2-pyridyl-thiocarbonyl, 1-pyrrolidinylcarbonyl, N-phenylcarbamoyl-, N-(diphenylmethyl)-carbamoyl-, N-isobutylcarbamoyl-, N-t-butylcarbamoyl-, N-(n-pentyl)-carbamoyl-, N-(3-(pentafluoroethyl)-phenyl)-carbamoyl-, N-(3-ethylphenyl)-carbamoyl-, N-(4-(trifluoromethyl)-phenyl)-carbamoyl-, N-(3-(trifluoromethyl) phenyl)-carbamoyl-, N-(3-t-butyl-phenyl)-carbamoyl-, N-(4-(t-butyl)-phenyl)-carbamoyl-, N-(3-(1,1-difluoro-2,2,2-trichloro)phenyl)-carbamoyl-, N-(4-(n-heptafluoropropyl)-phenyl)-carbamoyl-, N-(3-(n-heptafluoropropyl)-phenyl)-carbamoyl-, N-(3-(n-heptachloropropyl)-phenyl)-carbamoyl-, N-(3-biphenyl)-carbamoyl-, N-(3-(heptafluoro-i-propyl)-phenyl)-carbamoyl, N,N-(diisopropyl)-carbamoyl, N-(cyclopropylmethyl)-carbamoyl-, N-(1-adamantyl)-carbamoyl, N-(1,1,3,3-tetramethylbutyl)-carbamoyl, cyano, phenylsulfonyl, and ethoxycarbonylamino.

$R^3$ is selected from hydrogen, $C_{1-5}$alkyl, $CO_2R^4$, $CONR^4R^5$, $COR^5$, $S(O)_nR^5$, CN, and $C_xX_y$. In one embodiment of the present invention, $R^3$ is selected from hydrogen, methyl, $CO_2R^4$, $CONR^4R^5$, $COR^5$, $S(O)_nR^5$, CN, and $C_xX_y$. In another embodiment of the present invention, $R^3$ is selected from hydrogen, $CO_2R^4$, $CONR^4R^5$, $COR^5$, $S(O)_nR^5$, CN, and $CF_3$. In one class of the present invention, $R^3$ is selected from hydrogen, trifluoromethyl, methoxycarbonyl, ethoxycarbonyl, phenylsulfonyl, and cyano. In one subclass of the present invention, $R^3$ is trifluoromethyl.

$R^4$ is selected from: hydrogen, and $C_{1-10}$ straight or branched-chain alkyl. In one embodiment of the present invention, $R^4$ is selected from hydrogen, methyl, ethyl, n-propyl, isopropyl, n-butyl, isobutyl, and t-butyl. In one class of the present invention $R^4$ is selected from hydrogen, methyl, ethyl and isopropyl.

$R^5$ is selected from:
(1) hydrogen,
(2) aryl,
(3) aryl $C_{1-4}$alkyl,
(4) diaryl $C_{1-4}$alkyl,
(5) heteroaryl,
(6) heteroaryl $C_{1-4}$alkyl,
(7) $C_{3-10}$cycloalkyl, and
(8) substituted aryl substituted by one, two or three substituents independently selected from:
(a) —SH,
(b) —$SC_1$–$C_4$alkyl,
(c) —CN,
(d) —CO—$C_{1-8}$ alkyl,
(e) —CO—aryl,
(f) —$C_{1-8}$alkyl,
(g) —$C_3$–$C_8$ cycloalkyl,
(h) -aryl,
(i) -heteroaryl,
(j) —CO—heteroaryl,
(k) —$C_{1-4}$alkyl-aryl,
(l) —$CONR^6R^7$ where $R^6$ and $R^7$ are independently selected from:
(i) H,
(ii) $C_{1-8}$ alkyl,
(iii) $C_{3-8}$ cycloalkyl,
(iv) aryl,
or $R^6$ and $R^7$ together with the nitrogen to which they are attached form a 5–7 membered saturated heterocyclic ring containing 1–2 nitrogen atoms, and 0–1 oxygen atoms;
(m) —$NHCOR^6$,
(n) —$OCOR^6$,
(o) —$NR^6(CO)R^7$,
(p) —$NR^6(CO)NHR^7$,
(q) —$NHSO_2R^6$,
(r) —$OR^6$,
(s) —$NR^6R^7$,
(t) —$CO_2R^6$, and
(u) $C_xX_y$.

In one embodiment of the present invention, $R^5$ is selected from:
(1) hydrogen,
(2) aryl,
(3) aryl $C_{1-4}$alkyl,
(4) diaryl $C_{1-4}$alkyl,
(5) heteroaryl,
(6) heteroaryl $C_{1-4}$alkyl,
(7) $C_{3-10}$cycloalkyl, and
(8) substituted aryl substituted by one, two or three substituents independently selected from:
(a) —$SC_1$–$C_4$alkyl,
(b) —CN,
(c) —CO—$C_{1-8}$ alkyl,
(d) —CO—aryl,
(e) —$C_{1-8}$alkyl,
(f) —$C_3$–$C_8$ cycloalkyl,
(g) -aryl,
(h) -heteroaryl,
(i) —CO—heteroaryl,
(j) —$C_{1-4}$alkyl-aryl,
(k) —$CONR^6R^7$ where $R^6$ and $R^7$ are independently selected from:
(i) H,
(ii) $C_{1-8}$ alkyl,
(iii) $C_{3-8}$ cycloalkyl,
(iv) aryl,
or $R^6$ and $R^7$ together with the nitrogen to which they are attached form a 5–7 membered saturated heterocyclic ring containing 1–2 nitrogen atoms, and 0–1 oxygen atoms;
(l) —$NHCOR^6$,
(m) —$OCOR^6$,
(n) —$NR^6(CO)R^7$,
(o) —$NR^6(CO)NHR^7$,
(p) —$NHSO_2R^6$,
(q) —$OR^6$,
(r) —$NR^6R^7$, (s) —CO$_2$R$^6$, and (t) C$_x$X$_y$;

In another embodiment of the present invention, R$^5$ is selected from:

(1) hydrogen,
(2) aryl,
(3) aryl C$_{1-4}$alkyl,
(4) diphenylmethyl,
(5) heteroaryl,
(6) heteroaryl C$_{1-4}$alkyl,
(7) C$_{3-10}$cycloalkyl, and
(8) substituted aryl substituted by one, two or three substituents independently selected from:
 (a) —SC$_1$–C$_4$alkyl,
 (b) —CN,
 (c) —CO—C$_{1-8}$ alkyl,
 (d) —CO—aryl,
 (e) —C$_{1-8}$alkyl,
 (f) —C$_3$–C$_8$ cycloalkyl,
 (g) -aryl,
 (h) -heteroaryl,
 (i) —CO—heteroaryl,
 (j) —C$_{1-4}$alkyl-aryl,
 (k) —CONR$^6$R$^7$ where R$^6$ and R$^7$ are independently selected from:
  (i) H,
  (ii) C$_{1-8}$ alkyl,
  (iii) C$_{3-8}$ cycloalkyl,
  (iv) aryl,
  or R$^6$ and R$^7$ together with the nitrogen to which they are attached form a 5–7 membered saturated heterocyclic ring containing 1–2 nitrogen atoms, and 0–1 oxygen atoms;
 (l) —NHCOR$^6$,
 (m) —OCOR$^6$,
 (n) —NR$^6$(CO)R$^7$,
 (o) —NR$^6$(CO)NHR$^7$,
 (p) —NHSO$_2$R$^6$,
 (q) —OR$^6$,
 (r) —NR$^6$R$^7$,
 (s) —CO$_2$R$^6$, and
 (t) C$_x$X$_y$.

X is independently selected from F and Cl at each occurrence.

n is selected from 1 and 2;
x is an integer from 1 to 4;
y is 2x+1; and
z is an integer from 3 to 5.

In one embodiment of the instant invention are compounds of formula I wherein "a", "b", and "d" each represent single bonds and "c" represents a double bond.

In one class of the compounds of this embodiment are compounds wherein R$^1$ is methyl. Further illustrating this class are the compounds depicted in Table 1 below. Note that the substituents enclosed in parentheses have not been definitively assigned, and the actual R$^2$, R$^3$ assignment may be reversed.

TABLE 1

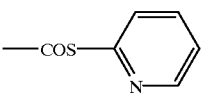

| Compound | R$^2$ | R$^3$ | |
|---|---|---|---|
| 16a,b | —H | —H | |
| 14a–c | —(H) | —(CO$_2$CH$_3$) | |
| 17a–c | —(CH$_3$) | —(CO$_2$CH$_2$CH$_3$) | |
| 15a,b | —(H) | —(SO$_2$Ph) | |
| 15c | —(SO$_2$Ph) | —(H) | |
| 18a,b | —CO$_2$CH$_2$CH$_3$ | —CO$_2$CH$_2$CH$_3$ | |
| 19a,b | —CN | —CN | |
| 23a,b | —(CN) | —(CF$_3$) | |
| 22a–d | —(CO$_2$CH$_2$CH$_3$) | —(CF$_3$) | |
| 24a,b | —(COPh) | —(CF$_3$) | Isomers A,B,C |
| 24a,b | —CO—Ph | —CF$_3$ | Isomer A |
| 24a,b | —CO—Ph | —CF$_3$ | Isomer B&C |
| 25a,b,c | 4-(trifluoro-methyl)-phenyl-carbamoyl | —CF$_3$ | |

In a subclass of the class of this embodiment where R$^1$ is methyl are compounds wherein R$^3$ is trifluoromethyl.

Further illustrating this subclass are the compounds in Table 2 below:

TABLE 2

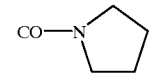

| Compound | R$^2$ |
|---|---|
| 29a,b | —COS-2-pyridyl |
| 28a,b | —CO$_2$—C(CH$_3$)$_3$ |
| 27 | —CO$_2$CH$_3$ |
| 26a–c | CO$_2$H |
| 32a,b | —CONHCH(Ph)$_2$ |
| 33a,b | —CONHCH$_2$CH(CH$_3$)$_2$ |
| 34a,b | —CO—N(pyrrolidine) |
| 35a,b | —CONH—C(CH$_3$)$_3$ |
| 36a,b | —CONH(CH$_2$)$_4$CH$_3$ |

TABLE 2-continued

[Structure: steroid-like scaffold with Me, CF₃, R², N-CH₃, ketone]

| Compound | R² |
|---|---|
| 31a,b | —CONH—(3-CF₂CF₃-phenyl) |
| 36a,b | —CONH—C(CH₃)₃ |
| 37a,b | —CONH—(3-C₂H₅-phenyl) |
| 38a,b | —CONH—(4-CF₃-phenyl) |
| 39a,b | —CONH—(3-CF₃-phenyl) |
| 40a,b | —CONH—(3-CF₂CCl₃-phenyl) |
| 41a,b | —CONH—(4-CF₂CF₂CF₃-phenyl) |
| 42a,b | —CONH—(3-CF₂CF₂CF₃-phenyl) |
| 43a,b | —CONH—(3-CCl₂CCl₃-phenyl) |
| 44a,b | —CONH—phenyl |
| 45a,b | —CONH—(3-Ph-phenyl) |
| 46a,b | —CONH—(3-CF(CF₃)₂-phenyl) |
| 47a,b | —CON—(CH(CH₃)₂)₂ |
| 48a,b | —CONH—CH₂—cyclopropyl |
| 49a,b | —CONH—adamantyl |
| 50a,b | —CONHC(CH₃)₂CH₂C(CH₃)₃ |

In a second embodiment of the present invention are compounds of formula I wherein "a" and "d" each represent single bonds and "b" and "c" each represent double bonds.

In one class of the compounds of this embodiment are compounds wherein $R^1$ is methyl. Further exemplifying this class are the compounds depicted in Table 3 below:

TABLE 3

[Structure: steroid-like scaffold with Me, R³, H, R², N-CH₃, ketone, with double bonds at b and c]

| Compound | R² | R³ |
|---|---|---|
| 51a,b | —CO₂CH₂CH₃ | —CF₃ |
| 52a,b | —CONH—(4-C(CH₃)₂-phenyl) | —CF₃ |
| 53 | —CO₂H | —CF₃ |
| 54 | —NHCO₂CH₂CH₃ | —CF₃ |

TABLE 3-continued

[Structure: tetracyclic compound with Me, R³, R², and N-CH₃, C=O groups; with double bonds in ring]

| Compound | R² | R³ |
|---|---|---|
| 55 | —CONH—C₆H₄—C(CH₃)₃ (meta) | —CF₃ |
| 56 | —CONHC(CH₃)₂CH₂C(CH₃)₃ | —CF₃ |
| 57 | —CONHC(CH₃)₃ | —CF₃ |

In a third embodiment of the instant invention are compounds of formula I wherein "a", "b", "c", and "d" each represent single bonds. In one class of the compounds of this embodiment are compounds wherein R¹ is methyl. Further illustrating this class are the compounds of Table 4 below:

TABLE 4

[Structure: fully saturated tetracyclic compound with Me, H, R³, R², N-CH₃, C=O]

| Compound | R² | R³ |
|---|---|---|
| 60 | —CONH—C₆H₅ | —CF₃ |
| 59 | —CO₂H | —CF₃ |
| 58 | —CO₂CH₃ | —CF₃ |
| 61 | —COHN—C₆H₄—CF₂CF₃ (meta) | —CF₃ |
| 68 | —CONHC(CH₃)₃ | —CF₃ |
| 69 | —CONHC(CH₃)₃ | —CF₃ |
| 67 | —NHCO₂CH₂CH₃ | —CF₃ |
| 64 | —CONH—C₆H₄—CH₂CH₃ (meta) | CF₃ |

TABLE 4-continued

[Structure same as above]

| Compound | R² | R³ |
|---|---|---|
| 65 | —CONH—C₆H₄—C(CH₃)₃ (meta) | —CF₃ |
| 66 | —CO—O—C₆H₅ | —CF₃ |
| 62 | —CO₂CH₂CH₃ | —CF₃ |
| 63 | —CO₂H | —CF₃ |
| 70 | —CONHC(CH₃)₂CH₂C(CH₃)₃ | —CF₃ |

In a fourth embodiment of the present invention are compounds of formula I wherein "a" and "b" each represent single bonds and "c" and "d" each represent double bonds.

In one class of the compounds of this embodiment are compounds wherein R¹ is methyl.

Further illustrating this class are the compounds in Table 5 below:

TABLE 5

[Structure: tetracyclic compound with Me, H, R³, R², N-CH₃, C=O, with double bonds in the right ring]

| Compound | R² | R³ |
|---|---|---|
| 21a–c | —CO₂CH₂CH₃ | —CF₃ |
| 20a,b | —CF₃ | —CF₃ |
| 79a–c | —CO₂H | —CF₃ |
| 80a–c | —CONH—C₆H₄—C(CH₃)₃ (meta) | —CF₃ |
| 81a–c | —CONHC(CH₃)₃ | —CF₃ |
| 82a–c | —CONHC(CH₃)₂CH₂C(CH₃)₃ | —CF₃ |
| 83a–c | —CONH—C₆H₅ | —CF₃ |

TABLE 5-continued

| Compound | R² | R³ |
|---|---|---|
| 84a–c | —CONH-(3-CF₂CF₃-phenyl) | —CF₃ |
| 85a–c | —CONH-(3-CF₂CF₂CF₃-phenyl) | —CF₃ |
| 86a–c | —CONH-(3-CF₂CCl₃-phenyl) | —CF₃ |
| 87a–c | —CONH-(3-C₂H₅-phenyl) | —CF₃ |

In a fifth embodiment of the present invention are compounds of structural formula I wherein "b", "c", and "d" each represent single bonds and "a" represents a double bond.

In one class of the compounds of this embodiment are compounds wherein R¹ is hydrogen.

Further exemplifying this class are the compounds in Table 6 below.

TABLE 6

| Compound | R² | R³ |
|---|---|---|
| 71 | —CO₂CH₂CH₃ | —CF₃ |
| 88 | —CO₂H | —CF₃ |

TABLE 6-continued

| Compound | R² | R³ |
|---|---|---|
| 89 | —CONH-(3-C(CH₃)₃-phenyl) | —CF₃ |
| 90 | —CONHC(CH₃)₃ | —CF₃ |
| 91 | —CONHC(CH₃)₂CH₂C(CH₃)₃ | —CF₃ |
| 92 | —CONH-phenyl | —CF₃ |
| 93 | —CONH-(3-CF₂CF₃-phenyl) | —CF₃ |
| 94 | —CONH-(3-CF₂CF₂CF₃-phenyl) | —CF₃ |
| 95 | —CONH-(3-CF₂CCl₃-phenyl) | —CF₃ |
| 96 | —CONH-(3-C₂H₅-phenyl) | —CF₃ |

A sixth embodiment of the instant invention relates to novel compounds of structural formula (II) having the nonsteroidal trans-anti-trans absolute configuration at the A,B and B,C ring junctures:

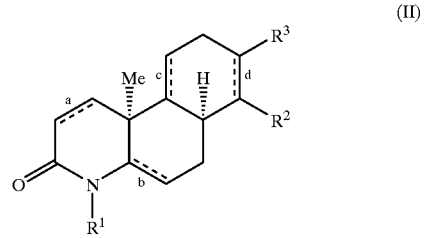

(II)

or a pharmaceutically acceptable salt, ester, or stereoisomer thereof.

In one class of this embodiment are compounds of formula (II) wherein
$R^1$ is selected from hydrogen and methyl;
$R^2$ is selected from:
(1) hydrogen,
(2) $CO_2R^4$,
(3) $CONR^4R^5$,
(4)

(5) $COR^5$,
(6) $S(O)_nR^5$,
(7) $NHCO_2R^4$,
(8) CN,
(9) $COSR^5$,
(10) methyl, and
(11) $C_xX_y$;
$R^3$ is selected from
(1) hydrogen,
(2) methyl,
(3) $CO_2R^4$,
(4) $CONR^4R^5$,
(5) $COR^5$,
(6) $S(O)_nR^5$,
(7) CN, and
(8) $C_xX_y$;
$R^4$ is selected from: hydrogen, and $C_{1-10}$ straight or branched-chain alkyl;
$R^5$ is selected from:
(1) hydrogen,
(2) aryl,
(3) aryl $C_{1-4}$alkyl,
(4) diaryl $C_{1-4}$alkyl,
(5) heteroaryl,
(6) heteroaryl $C_{1-4}$alkyl,
(7) $C_{3-10}$cycloalkyl, and
(8) substituted aryl substituted by one, two or three substituents independently selected from:
  (a) —$SC_1$–$C_4$alkyl,
  (b) —CN,
  (c) —CO—$C_{1-8}$ alkyl,
  (d) —CO—aryl,
  (e) —$C_{1-8}$alkyl,
  (f) —$C_3$–$C_8$ cycloalkyl,
  (g) -aryl,
  (h) -heteroaryl,
  (i) —CO—heteroaryl,
  (j) —$C_{1-4}$alkyl-aryl,
  (k) —$CONR^6R^7$ where $R^6$ and $R^7$ are independently selected from:
    (i) H,
    (ii) $C_{1-8}$ alkyl,
    (iii) $C_{3-8}$ cycloalkyl,
    (iv) aryl,
    or $R^6$ and $R^7$ together with the nitrogen to which they are attached form a 5–7 membered saturated heterocyclic ring containing 1–2 nitrogen atoms, and 0–1 oxygen atoms;
  (l) —$NHCOR^6$,
  (m) —$OCOR^6$,
  (n) —$NR^6(CO)R^7$,
  (o) —$NR^6(CO)NHR^7$,
  (p) —$NHSO_2R^6$,
  (q) —$OR^6$,
  (r) —$NR^6R^7$,
  (s) —$CO_2R^6$,
  (t) $C_xX_y$;
X is independently selected from F and Cl at each occurrence;
n is selected from 1 and 2;
x is an integer from 1 to 4;
y is 2x+1; and
z is an integer from 3 to 5,
or a pharmaceutically acceptable salt, ester or stereoisomer thereof.

In a subclass of this class are compounds of formula (II) wherein
$R^1$ is selected from hydrogen and methyl;
$R^2$ is selected from:
(1) hydrogen,
(2) $CO_2R^4$,
(3) $CONR^4R^5$,
(4)

(5) $COR^5$,
(6) $S(O)_nR^5$,
(7) $NHCO_2R^4$,
(8) $NHCOR^4$,
(9) $NHCOR^5$,
(10) CN,
(11) $COSR^5$, and
(12) $CF_3$;
$R^3$ is selected from:
(1) hydrogen,
(2) $CO_2R^4$,
(3) $CONR^4R^5$,
(4) $COR^5$,
(5) $S(O)_nR^5$,
(6) CN, and
(7) $CF_3$;
$R^4$ is selected from: hydrogen, and $C_{1-10}$ straight or branched-chain alkyl; $R^5$ is selected from:
(1) hydrogen,
(2) aryl,
(3) aryl $C_{1-4}$alkyl,
(4) diphenylmethyl,
(5) heteroaryl,
(6) heteroaryl $C_{1-4}$alkyl,
(7) $C_{3-10}$cycloalkyl, and
(8) substituted aryl substituted by one, two or three substituents independently selected from:
  (a) —$SC_1$–$C_4$alkyl,
  (b) —CN,
  (c) —CO—$C_{1-8}$ alkyl,
  (d) —CO—aryl,
  (e) —$C_{1-8}$alkyl,
  (f) —$C_3$–$C_8$ cycloalkyl, (g) -aryl,
(h) -heteroaryl,
(i) —CO—heteroaryl,
(j) —$C_{1-4}$alkyl-aryl,
(k) —$CONR^6R^7$ where $R^6$ and $R^7$ are independently selected from:
  (i) H,
  (ii) $C_{1-8}$ alkyl,
  (iii) $C_{3-8}$ cycloalkyl,
  (iv) aryl,
  or $R^6$ and $R^7$ together with the nitrogen to which they are attached form a 5–7 membered saturated heterocyclic ring containing 1–2 nitrogen atoms, and 0–1 oxygen atoms;
(l) —$NHCOR^6$,
(m) —$OCOR^6$,
(n) —$NR^6(CO)R^7$,
(o) —$NR^6(CO)NHR^7$,
(p) —$NHSO_2R^6$,
(q) —$OR^6$,
(r) —$NR^6R^7$,
(s) —$CO_2R^6$,
(t) $C_xX_y$;

X is independently selected from F and Cl at each occurrence;
n is selected from 1 and 2;
x is an integer from 1 to 4;
y is 2x+1; and
z is an integer from 3 to 5,
or a pharmaceutically acceptable salt, ester or stereoisomer thereof.

In a seventh embodiment of the present invention are compounds of structural formula (II) wherein "a", "b", and "d" each represent single bonds and "c" represents a double bond.

In one class of this embodiment are compounds of the following structural formula

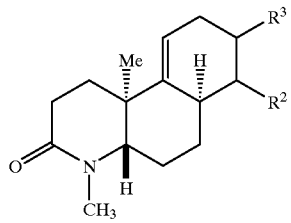

selected from:

| $R^2$ | $R^3$ | |
|---|---|---|
| —H | —H | |
| —(H) | —($CO_2CH_3$) | |
| —($CH_3$) | —($CO_2CH_2CH_3$) | |
| —(H) | —($SO_2Ph$) | |
| —($SO_2Ph$) | —(H) | |
| —$CO_2CH_2CH_3$ | —$CO_2CH_2CH_3$ | |
| —CN | —CN | |
| —(CN) | —($CF_3$) | |
| —($CO_2CH_2CH_3$) | —($CF_3$) | |
| —(COPh) | —($CF_3$) | Isomers A,B,C |
| —CO—Ph | —$CF_3$ | Isomer A |
| —CO—Ph | —$CF_3$ | Isomer B&C |

-continued

| $R^2$ | $R^3$ |
|---|---|
| 4—(trifluoromethyl)-phenylcarbamoyl | —$CF_3$ | wherein the regiochemistry of the substituents enclosed in parentheses has not been definitively assigned, and the actual $R^2$ and $R^3$ assignment may be reversed.

In a subclass of this class of this embodiment are compounds of the following structural formula

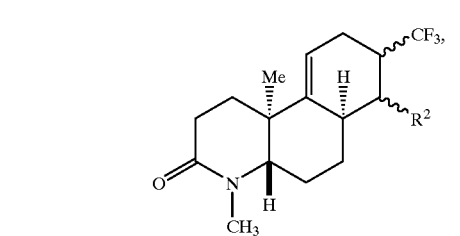

selected from $R^2$

—COS—(2-pyridyl)   —$CO_2$—$C(CH_3)_3$

—$CO_2CH_3$   —$CO_2H$   —CONHCH(Ph)$_2$

—CONHCH$_2$CH(CH$_3$)$_2$   —CO—N(pyrrolidine)

—CONH—$C(CH_3)_3$   —CONH(CH$_2$)$_4$CH$_3$

—CONH—(3-(CF$_2$CF$_3$)phenyl)   —CONH—$C(CH_3)_3$

—CONH—(3-($C_2H_5$)phenyl)

—CONH—(4-$CF_3$-phenyl)

—CONH—(3-$CF_3$-phenyl)

—CONH—(4-$CF_3CCl_3$-phenyl)

—CONH—(4-$CF_2CF_2CF_3$-phenyl)

-continued

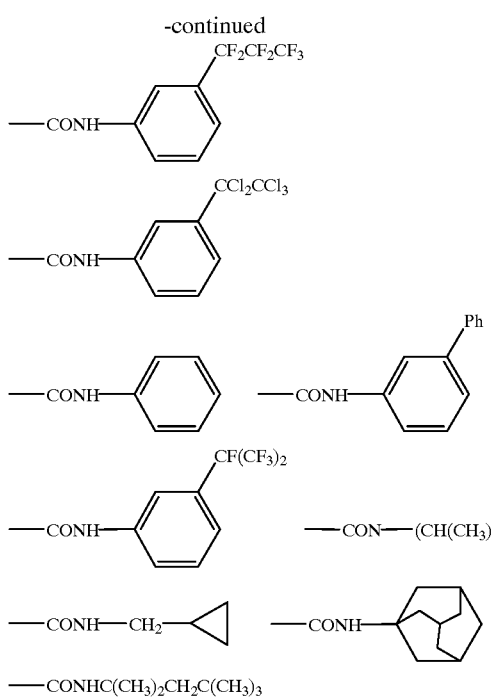

or a pharmaceutically acceptable salt, ester or stereoisomer thereof.

In an eighth embodiment of the present invention are compounds of structural formula (II) wherein "a" and "d" each represent single bonds and "b" and "c" each represent double bonds.

In a class of this embodiment are compounds of the following structural formula:

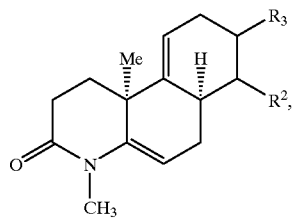

selected from:

| $R^2$ | $R^3$ |
|---|---|
| —$CO_2CH_2CH_3$ | —$CF_3$ |
| 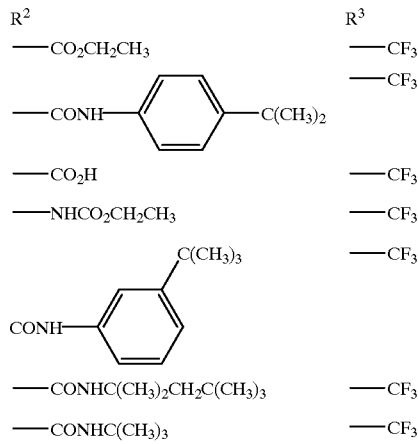 | —$CF_3$ |
| —$CO_2H$ | —$CF_3$ |
| —$NHCO_2CH_2CH_3$ | —$CF_3$ |
| | —$CF_3$ |
| —$CONHC(CH_3)_2CH_2C(CH_3)_3$ | —$CF_3$ |
| —$CONHC(CH_3)_3$ | —$CF_3$ | or a pharmaceutically acceptable salt, ester or stereoisomer thereof.

In a ninth embodiment of the present invention are compounds of formula (II) wherein "a", "b", "c", and "d" each represent single bonds.

In one class of this embodiment are compounds of the following structural formula:

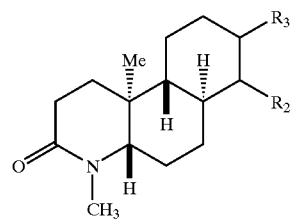

selected from:

| $R^2$ | $R^3$ |
|---|---|
| —CONH—Ph | —$CF_3$ |
| —$CO_2H$ | —$CF_3$ |
| —$CO_2CH_3$ | —$CF_3$ |
| 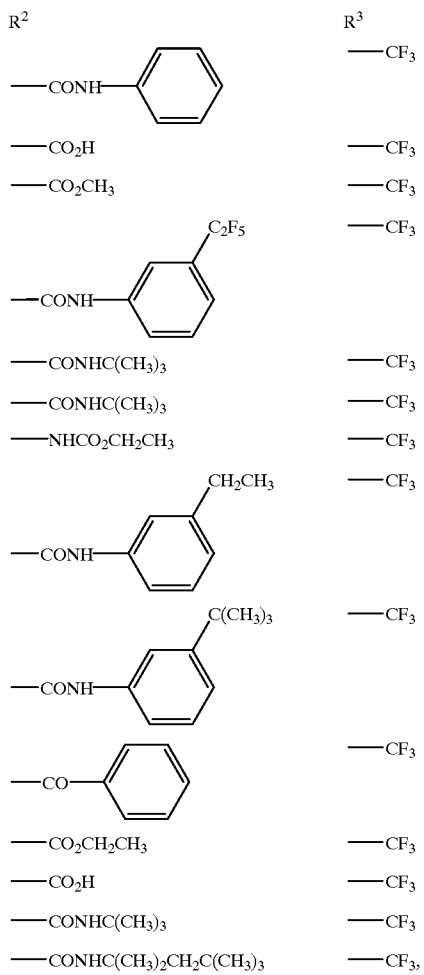 | —$CF_3$ |
| —$CONHC(CH_3)_3$ | —$CF_3$ |
| —$CONHC(CH_3)_3$ | —$CF_3$ |
| —$NHCO_2CH_2CH_3$ | —$CF_3$ |
| | —$CF_3$ |
| | —$CF_3$ |
| —CO—OPh | —$CF_3$ |
| —$CO_2CH_2CH_3$ | —$CF_3$ |
| —$CO_2H$ | —$CF_3$ |
| —$CONHC(CH_3)_3$ | —$CF_3$ |
| —$CONHC(CH_3)_2CH_2C(CH_3)_3$ | —$CF_3$, | or a pharmaceutically acceptable salt, ester or stereoisomer thereof.

In a tenth embodiment of the present invention are compounds of formula (II) wherein "a" and "b" each represent single bonds and "c" and "d" each represent double bonds.

In one class of this embodiment are compounds of the following formula

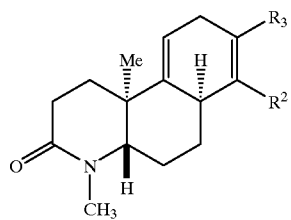

selected from:

| $R^2$ | $R^3$ |
|---|---|
| —$CO_2CH_2CH_3$ | —$CF_3$ |
| —$CF_3$ | —$CF_3$ |
| —$CO_2H$ | —$CF_3$ |
| 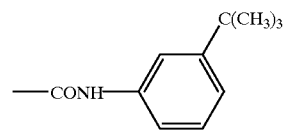 | —$CF_3$ |
| —$CONHC(CH_3)_3$ | —$CF_3$ |
| —$CONHC(CH_3)_2CH_2C(CH_3)_3$ | —$CF_3$ |
| 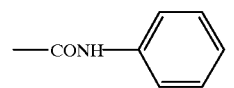 | —$CF_3$ |
| 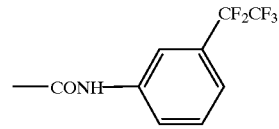 | —$CF_3$ |
| 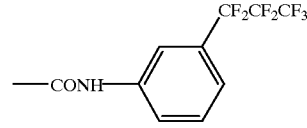 | —$CF_3$ |
| 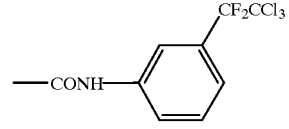 | —$CF_3$ |
| 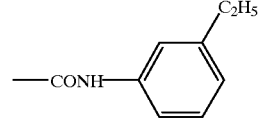 | —$CF_3$ | or a pharmaceutically acceptable salt, ester or stereoisomer thereof.

In an eleventh embodiment of the present invention are compounds of structural formula (II) wherein "b", "c", and "d" each represent single bonds and "a" represents a double bond.

In a class of this embodiment are compounds of the following structural formula

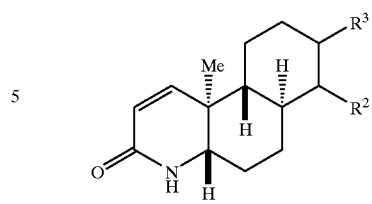

which are

| $R^2$ | $R^3$ |
|---|---|
| —$CO_2CH_2CH_3$ | —$CF_3$ |
| —$CO_2H$ | —$CF_3$ |
| 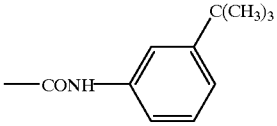 | —$CF_3$ |
| —$CONHC(CH_3)_3$ | —$CF_3$ |
| —$CONHC(CH_3)_2CH_2C(CH_3)_3$ | —$CF_3$ |
| 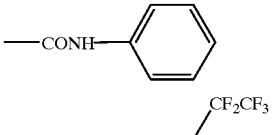 | —$CF_3$ |
| 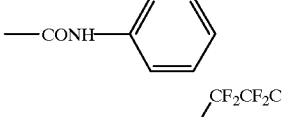 | —$CF_3$ |
| 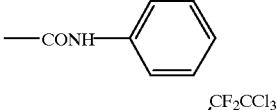 | —$CF_3$ |
| 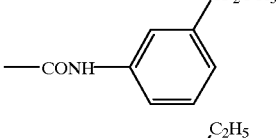 | —$CF_3$ |
| 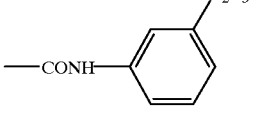 | —$CF_3$ |

When any variable (e.g., aryl, heterocycle, $R^1$, etc.) occurs more than one time in any substituent or in formula I, its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), secbutyl (s-Bu), tertbutyl (t-Bu), isopentyl, isohexyl, etc. "Alkyloxy" (or "alkoxy") represents an alkyl group having the indicated number of carbon atoms attached through an oxygen bridge, e.g., methoxy, ethoxy, propyloxy, isopropoxy, n-butoxy, iso-butoxy, sec-butoxy, t-butoxy and the like.

The term "aryl" includes phenyl and naphthyl. Preferably, aryl is phenyl (or Ph).

Heteroaryl is pyridyl, pyrazolyl, imidazolyl, furyl, isoxazolyl, pyrrolyl, oxazolyl, pyrimidinyl, quinolinyl, and pyrazinyl. In one class of the present invention, heteroaryl is selected from pyridyl, pyrimidinyl, quinolinyl and pyrazinyl.

Heterocyclic rings may be attached to structural formula I at any heteroatom (N or O) or carbon atom in the ring which results in the creation of a stable, uncharged structure.

In one class of compounds of the present invention, heterocycle is selected from: pyrrolidinyl, morpholinyl, piperazinyl, piperidyl, imidazolidinyl, imidazolinyl, pyrazolinyl and the like. In one class of compounds of the present invention, heterocycle is pyrrolidinyl.

Hydroxy and amino protecting groups are known to those of ordinary skill in the art, and any such groups may be used. For example, acetate, benzoate, ether and silyl protecting groups are suitable hydroxy protecting groups. Standard silyl protecting groups have the general formula —Si(Xa)$_3$, wherein each Xa group is independently an alkyl or aryl group, and include, e.g. trimethylsilyl, tri-ethylsilyl, tri-i-propylsilyl, triphenylsilyl as well as t-butyl-di-(Xb)-silyl where Xb is methyl, ethyl, i-propyl or phenyl (Ph). Standard amino protecting groups have the general formula —C(O)—Xc, wherein Xc is alkyl, aryl, O-alkyl or O-aryl, and include, e.g. N-t-butoxycarbonyl. See also *Protective Groups in Organic Synthesis*, T. W. Green et al. (John Wiley and Sons, 1991) for descriptions of protecting groups.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention. In particular, the following Schemes and Examples enable the preparation of compounds of structural formula (I) having the "natural" steroidal trans-anti-trans relative configuration (that is, the same configuration as testosterone at the A,B and B,C ring junctures) as racemic mixtures and compounds of structural formula (II) having the natural steroidal trans-anti-trans relative configuration, but the nonsteroidal trans-anti-trans absolute configuration (that is, the enantiomeric configuration which is opposite to the enantiomeric configuration of the natural steroid at the A,B and B,C ring junctures). By absolute configuration is meant the specification of (S) or (R) at each chiral center in the molecule. By relative configuration is meant the relationship between the configurations of two or more chiral (stereogenic) centers in a molecule independent of the (S) and (R) designation (for a discussion of stereochemical nomenclature, see E. L. Eliel, "Stereochemistry of Carbon Compounds, McGraw-Hill Book Co., New York, 1962).

The term "therapeutically effective amount" is that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated.

More particularly, the present invention relates to a method for treating hyperandrogenic conditions in a mammal in need of such treatment comprising the administration to the mammal in need of such treatment of a therapeutically effective amount of a compound of the present invention. The novel methods of treatment of this invention are for disorders known to those skilled in the art. The term "mammal" includes humans. Preferably, the method of the present invention is for treating hyperandrogenic conditions in a human in need of such treatment.

Hyperandrogenic conditions treatable by the method of the present invention include benign prostatic hyperplasia, androgenic alopecia (including male pattern baldness, female pattern baldness and female hirsutism), acne vulgaris, seborrhea, prostatitis and prostatic carcinoma. The method of the present invention may also be employed in the treatment of sweat-related conditions such as apocrine gland sweating, hyperhidrosis, and hydradenitis suppurativa, in the treatment of polycystic ovary syndrome, in the prevention and treatment of premature labor, in the prevention and treatment of bone loss, and to treat cardiovascular disease by raising HDL cholesterol levels.

The use of 5α-reductase inhibitors in the treatment of sweat related conditions is described in U.S. Pat. No. 5,512,555. Hyperhidrosis is defined as an increase above normal in sweat production. This is diagnosed when sweating occurs under conditions where it would not normally be expected or is excessive in response to emotional or thermal stimuli. Hydradenitis suppurativa (HS) is a chronic inflammatory disorder of apocrine sweat glands in which abscesses and drainage sinuses develop in the axilla and/or perineal area. The pathogenesis of HS is felt to be similar to acne: poral occlusion, bacterial colonization, androgenic stimulations and inflammation all seem to be important.

The use of 5α-reductase inhibitors to increase HDL cholesterol levels is described in PCT application US95/07215, which published as WO96/08239.

"Preventing and treating bone loss and related diseases" relates to methods of treating and/or preventing osteoporosis and osteopenia and other diseases where inhibiting bone loss may be beneficial, including: Paget's disease, malignant hypercalcemia, periodontal disease, joint loosening and metastatic bone disease, as well as reducing the risk of fractures, both vertebral and nonvertebral.

The present invention has the objective of providing methods of treating hyperandrogenic conditions including androgenic alopecia, male pattern baldness, acne vulgaris, seborrhea, and female hirsutism by oral, systemic, parenteral or topical administration of the novel compounds of formula I either alone or in combination with a 5α-reductase 2 inhibitor, preferably selected from finasteride and epristeride, or a potassium channel opener, or a retinoic acid or derivative thereof. Alternatively, treatment may encompass administration of a combination of a compound of structural formula (I) or (II) with a 5α-reductase 2 inhibitor, preferably selected from finasteride and epristeride and another active agent such as a potassium channel opener, or a retinoic acid or derivative therof. The term "treating androgenic alopecia" is intended to include the arresting and/or reversing of androgenic alopecia, and the promotion of hair growth.

The present invention has the further objective of providing methods of treating benign prostatic hyperplasia, prostatitis, and treating and/or preventing prostatic carcinoma by oral, systemic or parenteral administration of the novel compounds of formula (I) or (II) either alone or in combination with a 5α-reductase 2 inhibitor, preferably selected from finasteride and epristeride. Alternatively, treatment may encompass administration of a combination of a compound of structural formula (I) or (II) with a 5α-reductase 2 inhibitor and/or another active agent such as an α1 or an α1$_a$ adrenergic receptor antagonist (α1$_a$ receptor antagonists were formerly called α1$_c$ receptor antagonists).

The present invention also has a further objective of providing methods of treating acne vulgaris, androgenic alopecia, seborrhea, female hirsutism, benign prostatic hyperplasia, prostatitis and the preventing and/or treating of prostatic cancer, by oral, systemic, parental or topical administration of a combined therapy of a therapeutically effective amount of a compound of formula I with a therapeutically effective amount of an anti-androgen, such as, e.g., flutamide, spironolactone or casodex.

The present invention further has the objective of treating, preventing, and reducing the risk of premature labor and stopping labor preparatory to Cesarean delivery by oral, rectal, intravaginal, topical or parenteral (including subcutaneous, intramuscular and intravenous administration) administration of a compound of structural formula (I) or (II) either alone or in combination with another 5α-reductase inhibitor, either a type 1 inhibitor, a type 2 inhibitor, or a dual inhibitor, other tocolytic agents used in the treatment of preterm labor such as β-adrenergic agonists (e.g., ritodrine, isoproterenol, terbutaline, albuterol), magnesium sulfate, ethanol, other oxytocin antagonists (e.g., atosiban), calcium transport blockers (e.g., nicardipine, nifedipine), prostaglandin synthesis inhibitors (e.g., indomethacin), nitric oxide donors (e.g., nitroglycerine, S-nitroso-N-acetylpenicillamine), phosphodiesterase inhibitors, and progestins (e.g., progesterone). The compound of structural formula (I) or (II) of the instant invention may also be used in combination with antenatal steroids (e.g., dexamethasone). This particular combination has beneficial effects on the neonate by both decreasing uterine activity to prolong gestation and increasing fetal maturation. It will be understood that the scope of combinations of the compounds of this invention with other agents useful for treating preterm labor related conditions includes in principle any combination with any pharmaceutical composition useful for treating preterm labor, or stopping labor prior to Cesarean delivery.

The present invention further has the objective of treating apocrine gland sweating and hyperhidrosis, by administration of a compound of structural formula (I) or (II) either alone or in combination with a therapeutically effective amount of a topical antiperspirant such as an aluminum salt, e.g. aluminum hydroxide and/or a topical or oral anticholinergic agent and optionally including a deodorant.

Still another objective of the present invention is the treatment of hydradenitis suppurativa by administration of the compounds of structural formula (I) or (II) either alone or in combination with an anticholinergic agent, antibiotics and/or isotretinoin each of which can be administered topically or orally.

For combination treatment with more than one active agent, where the active agents are in separate dosage formulations, the active agents can be administered concomitantly, or they each can be administered at separately staggered times.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an antiandrogenic agent.

The compounds of structural formula (I) or (II) useful in the present invention are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices may be administered systemically, by oral administration or by intravenous or intramuscular injection or topically.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carriers, and placing the mixture in gelatin capsules.

Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Topical preparations containing the active drug component can be admixed with a variety of carrier materials well known in the art, such as, e.g., alcohols, aloe vera gel, allantoin, glycerine, vitamin A and E oils, mineral oil, propylene glycol, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 50 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The compounds of the present invention may be used in the preparation of a medicament useful for the treatment of hyperandrogenic disorders including: acne vulgaris, androgenic alopecia, male pattern baldness, seborrhea, female hirsutism, benign prostatic hyperplasia, prostatitis, prostatic cancer, bone-loss related diseases, polycystic ovary syndrome, and preterm labor.

For the treatment of acne vulgaris, androgenic alopecia, male pattern baldness, seborrhea, female hirsutism, benign prostatic hyperplasia, prostatitis and the prevention and/or treatment of prostatic cancer, as well as sweat-related conditions and bone loss, the compounds of the instant invention can be combined with a therapeutically effective amount of another 5α-reductase inhibitor, such as finasteride or epristeride, or other 5α-reductase inhibitor compounds having type 2 activity, type 1 activity or dual activity for both isozymes, in a single oral, systemic, or parenteral pharmaceutical dosage formulation. Alternatively, a combined therapy can be employed wherein the compound of formula I and the other 5α-reductase inhibitor are administered in separate oral, systemic, or parenteral dosage formulations. Also, for the skin and scalp related disorders of acne vulgaris, androgenic alopecia, male pattern baldness, seborrhea, and female hirsutism, the compounds of the instant invention and another 5α-reductase inhibitor such as finasteride or epristeride can be formulated for topical administration. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. Nos. 4,377,584 and 4,760,071 which describe dosages and formulations for 5α-reductase inhibitors.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. Therapy may further comprise the administration of a 5α-reductase type 2 inhibitor such as finasteride or epristeride, or a 5α-reductase type 1 inhibitor, or a type 1 and type 2 dual inhibitor, in combination with a compound of the present invention and a potassium channel opener such as minoxidil. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. Nos. 4,596,812, 4,139,619 and WO 92/02225, published Feb. 20, 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g. an ester or amide derivative thereof, such as e.g., tretinoin or isotretinoin. Optionally, this combined therapy for acne vulgaris may further include a 5α-reductase type 2 inhibitor such as finasteride or epristeride, or a 5α-reductase type 1 inhibitor, or a dual type 1 and type 2 inhibitory compound.

Also, for the treatment of benign prostatic hyperplasia, a combined therapy comprising a administration of a compound of formula I with a 5α-reductase type 2 inhibitor, such as e.g., finasteride, and an alpha-1 adrenergic receptor antagonist, such as e.g., terazosin, doxazosin, prazosin, bunazosin, indoramin or alfuzosin, may be employed. More particularly, the combined therapy can comprise administering a compound of formula I with a 5α-reductase type 2 inhibitor, such as e.g., finasteride, and an alpha-b $1_a$ adrenergic receptor antagonist (formerly called an alpha-$1_c$ adrenergic receptor antagonist). Compounds which are useful as alpha-$1_a$ adrenergic receptor antagonists can be identified according to procedures known to those of ordinary skill in the art, for example, as described in PCT/US93/09187 (WO94/08040, published Apr. 14, 1994); PCT/US94/03852 (WO 94/22829, published Oct. 13, 1994); PCT/US94/10162 (WO 95/07075, published Mar. 16, 1995), and U.S. Pat. No. 5,403,847.

Also, for the treatment of acne vulgaris, androgenic alopecia, seborrhea, female hirsutism, benign prostatic hyperplasia, prostatitis and the prevention and/or treatment of prostatic cancer, a combined therapy can be used by administering a therapeutically effective amount of a compound of formula I with a therapeutically effective amount of an anti-androgen, such as, e.g., flutamide, spironolactone or casodex.

For combination treatment with more than one active agent, where the active agents are in separate dosage formulations, the active agents can be administered concurrently, or they each can be administered at separately staggered times.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The starting diene 6 can be prepared as shown in Scheme 1. 2-Methyl-1,3-cyclohexanedione, acrylamide, and p-toluenesulfonic acid in N,N-dimethylacetamide were warmed to 75° for 16 hrs, then heated at reflux for 6.5 hrs to form the bicyclic enone 1. Other strong organic acids such as benzenesulfonic acid and trifluroacetic acid, and polar solvents such as dimethylformamide and formamide may be used.

The lactam nitrogen in 1 was methylated with a strong base, sodium hydride, and methyl iodide in dimethylformamide at 0° C. and then at room temperature to form 2. Other bases such as potassium hydride and potassium t-butoxide, methylating agents such as methyl bromide and dimethyl sulfate, and solvents such as dimethylsulfoxide and N,N-dimethylacetamide may be employed. Also phase transfer conditions such as methyl chloride with concentrated aqueous sodium hydroxide, a nonpolar solvent such as ether or hexane, and a phase transfer agent such as tetrabutylammonium chloride may be used.

The double bond and ketone in the enone 2 were reduced to the saturated alcohol 3 by hydrogenation at room temperature with platinum oxide catalyst in acetic acid with hydrogen at atmospheric pressure. Other catalysts such as palladium on carbon and solvents such as methanol and ethyl acetate could be employed. Also transfer hydrogenation conditions using palladium on carbon catalyst and cyclohexene or 1,3-cyclohexadiene as a hydrogen donor could be employed.

The alcohol 3 was oxidized to the ketone 4 with N-methylmorpholine-N-oxide, powdered molecular sieves, and tetrapropylammonium perruthenate in methylene chloride at room temperature. Other mild oxidizing agents such as dimethylsulfoxideoxalyl chloride, dimethylsulfoxide-sulfur trioxide, and pyridinium dichromate may be employed.

The ketone 4 was converted into the enol triflate 5 with a strong base, potassium hexamethyldisilazide in toluene, and the triflating agent, N-phenyltrifluoromethylsulfonimide, in tetrahydrofuran at 10° C. to room temperature. Other strong bases such as lithium and sodium hexamethyldisilazide, lithium diisopropylamide, and sodium hydride, other triflating agents such as 4 -pyridyltrifluoromethylsulfonimide, and solvents such diethyl ether and dimethoxyethane may be employed.

The enol triflate 5 was reacted with tributyl(vinyl)tin, anhydrous lithium chloride, and tetrakis (triphenylphosphine)-palladium(0) in tetrahydrofuran at 65° C. to form the diene 6.

SCHEME 1

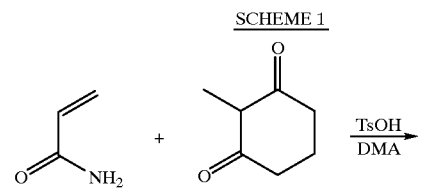

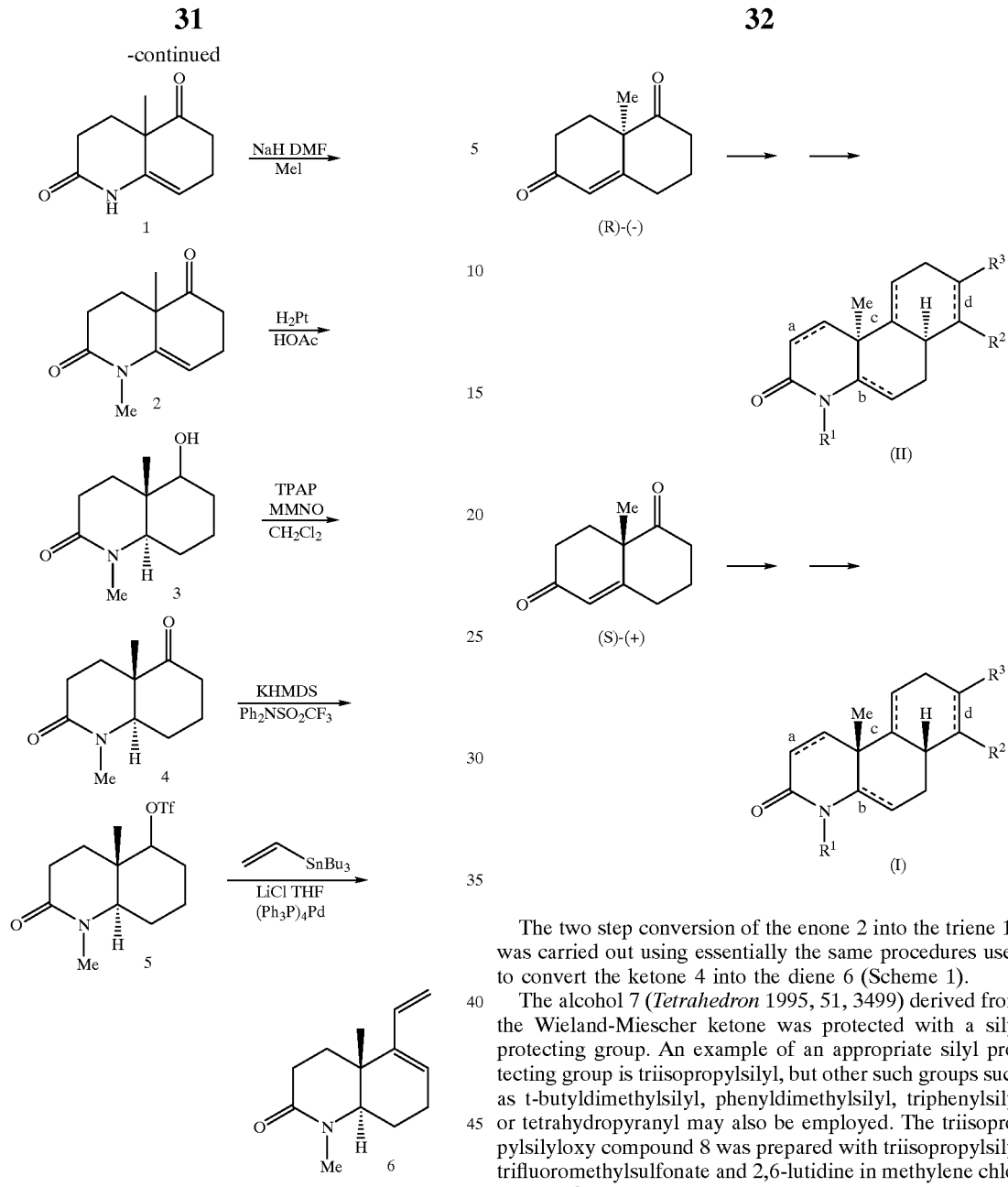

Scheme 2 outlines the synthesis of the bicyclic trienes 13 and 75 starting from either the bicyclic enone 2 (Scheme 1) or the bicyclic alcohol 7 derived from the Wieland-Miescher ketone. The latter route was used to prepare the (+)- and (−) enantiomers of 13 starting from the (−) or (+) Wieland-Miescher ketone, respectively, as well as for the synthesis of the 4-(2,4-dimethoxybenzyl) triene 75. The (S)-(+) Wieland-Miescher ketone enantiomer affords the bicyclic trienes 13 and 75 and final tricyclic compounds of structural formula (I) of the present invention having both the natural steroid trans-anti-trans relative and absolute configurations. The (R)-(−) Wieland-Miescher ketone enantiomer affords the bicyclic trienes 13 and 75 and final tricyclic compounds of structural formula (II) of the present invention having the natural steroid trans-anti-trans relative configuration but nonsteroidal trans-anti-trans absolute configuration.

The two step conversion of the enone 2 into the triene 13 was carried out using essentially the same procedures used to convert the ketone 4 into the diene 6 (Scheme 1).

The alcohol 7 (*Tetrahedron* 1995, 51, 3499) derived from the Wieland-Miescher ketone was protected with a silyl protecting group. An example of an appropriate silyl protecting group is triisopropylsilyl, but other such groups such as t-butyldimethylsilyl, phenyldimethylsilyl, triphenylsilyl or tetrahydropyranyl may also be employed. The triisopropylsilyloxy compound 8 was prepared with triisopropylsilyl trifluoromethylsulfonate and 2,6-lutidine in methylene chloride at 0° to room temperature. Other silylating conditions such as triisopropylsilylchloride and imidazole in dimethylformamide may be employed.

The silyloxy enone 8 was oxidized to the seco acid 9 using sodium periodate with a catalytic amount of potassium permanganate in aqueous t-butanol and sodium carbonate at 110°. Ozonization in methylene chloride-methanol followed by aqueous sodium hydroxide may also be employed. The seco acid 9 was converted into the bicyclic lactams 10 and 72 by reaction with methylamine hydrochloride and 2,4-dimethoxybenzylamine hydrochloride, respectively, and sodium acetate in ethylene glycol at 100° to 200°. The free amines can also be employed in which case the sodium acetate can be omitted. Other solvents such as 2-ethoxyethanol and 2-methoxyethanol could be used.

The triisopropylsilyl protecting group in both 10 and 72 was removed by treatment with tetrabutylammonium fluoride in tetrahydrofuran at room temperature. Hydrofluoric acid in acetonitrile may also be employed. The alcohol product 11 from the 4-methyl compound 10 was oxidized to the ketone 2 using the same N-methylmorpholine-N-oxide/ tetrapropylammonium perruthenate conditions used to oxidize 3 to 4 (Scheme 1). The 4-(2,4-dimethoxybenzyl) compound 72 was deprotected with tetrabutylammonium fluoride and the alcohol oxidized directly to the ketone 73. The two step conversion of 2 and 73 to 13 and 75, respectively, was carried out using essentially the same procedures for converting 4 into 6 (Scheme 1).

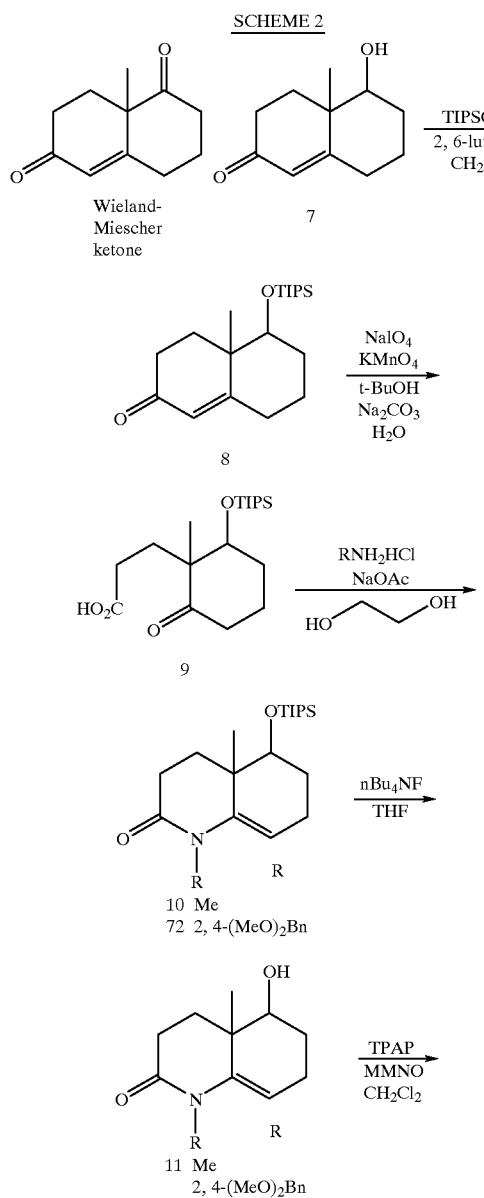

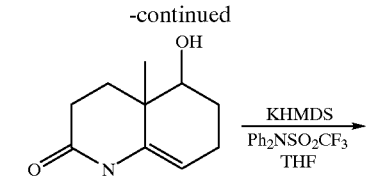

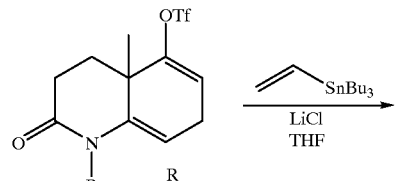

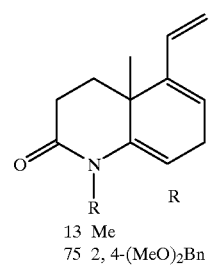

Many of the tricyclic compounds of structural formula (I) were prepared by Diels-Alder reactions between the dienes 6, 13, and 75 and various olefenic (A) and acetylenic (B) dienophiles. Other compounds of structural formula (I) were prepared by subsequent chemical transformation of these initial tricyclic Diels-Alder products.

The tricylic compounds of structural formula (I) that were prepared by the Diels-Alder reaction of the diene 6 with various olefinic dienophiles (A) are shown in Table 1. In all cases the products were mixtures of isomers.

It is well know that the Diels-Alder reaction between an asymmetric diene and an asymmetric dienophile potentially can form three types of diastereomers (Scheme 3). The regiochemical isomers C and D are formed depending upon the orientation of A with respect to the diene, while the stereochemistry in the dienophile is maintained in the products C and D. The two epimers at 6a (E and F) are formed depending on whether the dienophile approaches the diene from the D or the (x face, respectively. Finally depending upon how the dienophile interacts with the diene, the 7-exo (G) or the 7-endo (H) isomers are formed.

SCHEME 3

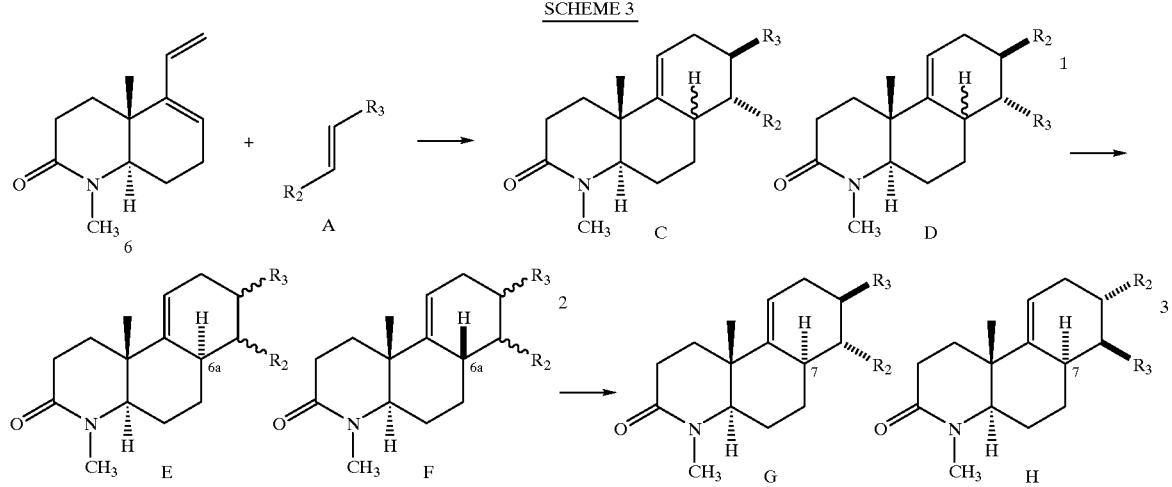

The preferred dienophile, ethyl 4,4,4-trifluorocrotonate (A, $R^2$=$CO_2$Et, $R^3$=$CF_3$), is typical (Example 11). Thermal (93° in benzene) reaction gave an inseparable mixture of tricyclic isomeric esters potentially of any of the six types (C—H) in Scheme 3. Based on the integration of the 10-vinyl, 4a, and the 10b-methyl peaks in the NMR spectrum three isomers were present in the ratio of 7:2:1. As detailed in Examples 15 and 19, this mixture of ethyl esters was saponified and the resulting carboxylic acids converted into the t-butyl amides. The mixture of amides could be separated by careful HPLC. Detailed NMR analysis established the regio- and stereochemistry of the isomers as 30a for the major, less polar isomer, and 30b for the minor, more polar isomer. Based on these amide isomer assignments, the structures of the two major ester isomers were deduced to be 22c for the major and 22d for the minor isomer. Therefore both of the major products have the D regiochemistry, while the major isomer results from reaction from the β-face of 6 (E) and a preference for 7-exo (G) stereochemistry. The 4a hydrogen in the major isomer (22c) has a large downfield shift (δ 3.51 vs 3.05) compared to the minor isomer (22d), while the 10-vinyl (δδ 5.60 vs 5.54) and 10a-methyl (δ 1.11 vs 1.05) had much smaller downfield shifts. Similar NMR patterns obtain for the t-butyl amide isomers (30a, 30b) as well as for most of the major products from the other Diels-Alder reactions listed in Table 1. This is the basis for the tentative structure assignments for the major products 14c (Example 3), 15c (Example 4), 17c (Example 6), 18b (Example 7), 19b (Example 8), 20b (Example 9), 21c (Example 10), and 24c (Example 13).

A trisubstituted dienophile ethyl 4,4,4-trifluoro-2-cyanocrotonate was reacted with 6 (Example 12). The carboethoxy group was removed by heating the product with potassium acetate in dimethylsulfoxide at 150° C. A mixture of four isomers (23a and 23b) were formed in nearly equal ratio.

N-(4'(t-butyl)phenyl)-4,4,4-trifluorocrotonamide was prepared (Example 14) by 1-(3-dimethylaminopropyl)-3-ethylcarbodiimide hydrochloride mediated condensation of 4,4,4-trifluorocrotonic acid with 4-t-butylaniline. Diels-Alder reaction with 6 gave a mixture of three isomers (A, B, C, in decreasing polarity) which could be separated by HPLC. Isomer B had an NMR spectrum consistent with isomer 25c, but the spectra for isomers A and C are too similar to assign structure 25d to either. This route provides an alternate synthesis for the preferred tricyclic 8-trifluoromethyl-7-carboxamide structures.

The phenyl vinyl sulfone Diels-Alder products 15a and 15b were reduced with sodium amalgam to a single 7,8-unsubstituted tricyclic isomer, probably 16b (Example 5).

The carboxylic acid derivatives that are derived from mixture of tricyclic 8-trifluoromethyl-7-carboethoxy isomers 22a and 22b are listed in Table 2. The ethyl esters 22a and 22b were saponified with sodium hydroxide in aqueous methanol to give the mixture of carboxylic acids 26a and 26b (Example 15). Fractional recrystallization of 26a and 26b gave a sample of the pure major isomer 26c. Isomer 26c was converted into the methyl ester 27 with trimethylsilyl-diazomethane in toluene-methanol (Example 16). The carboxylic acids 26a and 26b were reacted with N,N'-diisopropyl-O-t-butylisourea in methylene chloride and methanol to form the t-butyl ester isomers 28a and 28b (Example 17). The isomers 26a and 26b were converted into the 2-pyridylthio ester isomers 29a and 29b by the action of triphenylphosphine and 2,2'-dithiopyridine in toluene (Example 18).

The remaining compounds in Table 2 are amides formed from the carboxylic acid isomers 26a and 26b (Examples 19–39). The amides were prepared from 26a and 26b by forming the acid chloride with oxalyl chloride and pyridine in methylene chloride followed by reaction with the appropriate amine or aniline, and the acylation catalyst, pyridine or 4-dimethylaminopyridine, in dry tetrahydrofuran. Other acid chloride forming reagents such as thionyl chloride and phosphorus trichloride could be used. Also the carboxylic acids could be activated for amide formation by reaction with N,N-bis(2-oxo-3-oxazolidinyl)phosphorinic chloride or benzotriazol-1-yloxytris(dimethylamino)phosphonium hexafluorophosphate in dimethylformamide. Amide formation results in an increase in the amount of the minor isomer (typically 2:1 or 3:2 instead of 7:2) due to more facile formation or reaction of the acid chloride or both. Two of the amide isomer mixtures were separated. As outlined above the t-butylamides 30a and 30b (Example 19) were separated by straight phase HPLC on silica gel and the structures assigned based on detailed NMR studies. The 3-(pentafluoroethyl)anilides 31a and 31b (Example 20) were separated by recrystallization and reversed phase HPLC. The pattern of the NMR shifts observed for the 4a, 10a-methyl, and 10-vinyl signals for the major and minor amide isomers discussed above were consistent for the two amides that were separated as well as all of the unresolved amide mixtures.

The boron trichloride catalyzed Diels-Alder reaction with the triene 13 and ethyl 4,4,4-trifluorocrotonate (Scheme 3, Example 40) gave a 1:1 mixture of the tricyclic esters 51a and 51b. Thus more of the preferred 6ap isomer (51b) resulting from a-face reaction is produced compared to the reaction with the diene 6. Other Lewis acids such as boron trifluoride, boron tribromide, aluminum chloride, stannic chloride, titanium tetrachloride, diethylaluminum chloride, and ethylaluminum dichloride can be used. Also 51a and 51b can be readily separated by straight phase HPLC on silica gel. The structural assignments for 51a and 51b are based on hydrogenation to common fully saturated structures derived from the diene 6 (see below).

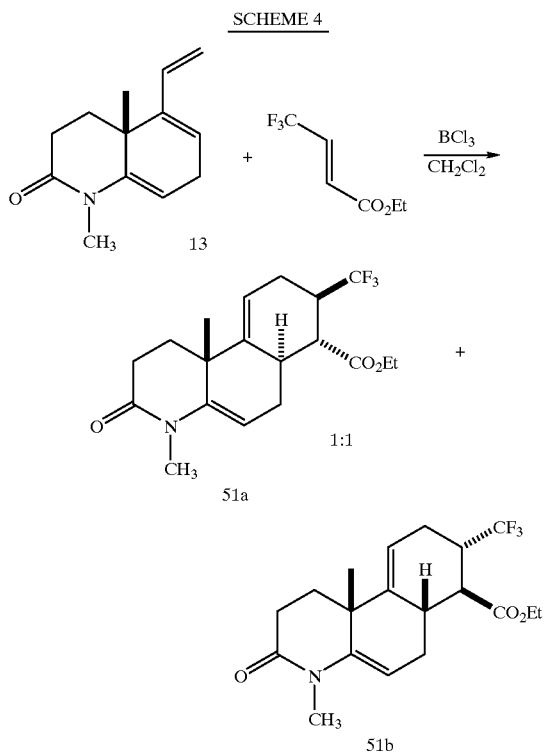

SCHEME 4

Table 3 lists the tricyclic diene compounds derived from 51a and 51b. The use of (+)- and (−)-13 gave the corresponding (+) and (−) enantiomers of 51b. Saponification of racemic, (+)- and (−)-51b gave the corresponding racemic, (+)- and (−)-acids 53 (Example 42). The (+) and (−) carboxylic acids 53 were converted into (+) and (−) 3-t-butylanilides 55 by conversion to the acid chloride with thionyl chloride and pyridine in toluene and subsequent reaction with 3-t-butylaniline and 4-dimethylaminopyridine at 90° C. in toluene (Example 44). The (−)-t-octyl amide (56)(Example 45) and the (+)-t-butyl amide (57)(Example 46) were prepared from (−)-53 and (+)-53 respectively using the same procedure. The thermal Diels-Alder reaction between 13 and N-(4'(t-butyl)phenyl)-4,4,4-trifluorocrotonamide gave a mixture of three isomers 52a and 52b (Example 41). Reaction of the racemic acid 53 with diphenylphosphoryl azide and triethylamine in ethanol under reflux for 7 hrs afforded the 7β-carboethoxyamino diene 54 (Example 43).

The fully saturated tricycles prepared by catalytic hydrogenation of the olefinic compounds in Tables 2 and 3 or derived therefrom are listed in Table 4. The major carboxylic isomer 26c was hydrogenated with platinum in acetic acid, converted to the methyl ester 58 with trimethylsilyldiazomethane for purification (Example 47). Saponification of 58 with aqueous sodium hydroxide afforded the pure saturated acid 59 (Example 48). The anilide 60 was prepared from the saturated acid 59 by first making the 2-pyridylthio ester with triphenylphosphine and 2,2'-dithiopyridine in toluene followed by reaction with aniline and silver triflate in tetrahydrofuran (Example 49). The major 3-(pentafluoroethyl)anilide isomer 31a was hydrogenated with platinum in acetic acid to give the saturated compound 61 (Example 50). Similarly the major t-butylamine isomer 30a was hydrogenated to give the saturated compound 69 (Example 59). The assignment of the 10aα stereochemistry to the hydrogenation products 58, 61, and 69 is based on the assumption of α face delivery of hydrogen and was not proven.

The minor t-butylamide isomer 30b was hydrogenated with platinum in acetic acid to give the saturated compound 68. Racemic 68 was resolved into (+)-68 and (−)-68 by HPLC on a chiral column (Example 57). The diene t-butylamide isomer (+)-57 (derived from (+)-51b) was hydrogenated to give a good yield of (+)-68 (Example 58) identical is all respects with the compound derived from 30b. This establishes the stereochemical relationship between the tricyclic compounds derived from the diene 6 and the triene 13. In particular it establishes the 6ap stereochemistry for 51b.

Hydrogenation of racemic and (−)-5 lb with platinum in acetic acid to give the saturated ester racemic and (−)-62 (Example 51). Saponification of the ester 62 was slow, and it was necessary to use 9 M potassium hydroxide in ethylene glycol at 120° for 22 hrs to produce the acid 63 (Example 52). Because of the hindered nature of the 7-carboxyl in 63, conversion of it to amides through the acid chloride was difficult. However, the 3-ethylanilide 64 (Example 53) and the 3-(t-butyl)anilide 65 (Example 54) were prepared. It is preferable to prepare the saturated amides by hydrogenation of the diene amides. Thus the t-butylamide (+)-57 (Example 58), the t-octylamide (−)-56 (Example 60), and the 3-(t-butyl)anilides (−)- and (+)-55 (Example 61) were hydrogenated with platinum in acetic acid to the saturated amides (+)-68, (−)-70, and (−)- and (+)-65, respectively. A single crystal x-ray structure determination on (−)-65 confirmed the molecular connectivity and relative stereochemistry as drawn.

The 8-benzoyl compound 66 was prepared (Example 55) from the saturated acid 63 by reacting the acid chloride derived from it with benzene and aluminum chloride in methylene chloride.

The diene urethane 54 was hydrogenated with platinum in acetic acid to give the saturated 7-carboethoxyamino compound 68 (Example 57).

SCHEME 5

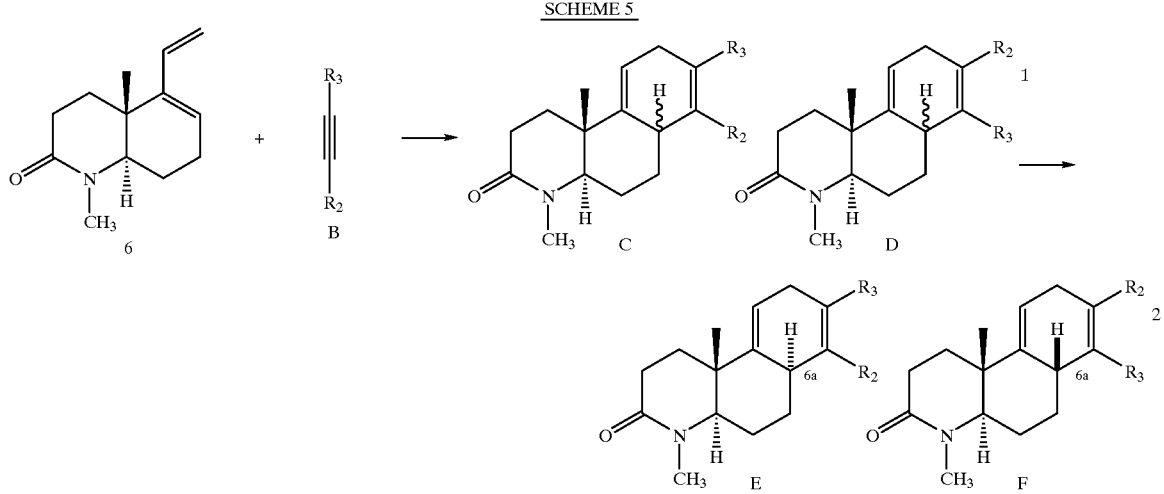

When an unsymmetric acetylenic dienophile (B) reacts with a diene such as 6 the isomer picture is simpler than with an olefinic dienophile (Scheme 3). Exo/endo isomers are not formed, and, of course, if B is symmetric, the regio isomers C and D are not formed. Table 5 lists the tricyclic dienes formed by reaction of the diene 6 with acetylenic dienophiles. The 7-carboxamides 80a,b,c–87a,b,c are prepared from the acid 79a–c which is made by saponifying the esters 21a–c (Example 63).

Compounds with a double bond at the 1-position are listed in Table 6. The triene 75 (Scheme 2) was reacted with ethyl 4,4,4-trifluorocrotonate with boron trichloride catalysis to form a 1:1 mixture of the tricyclic esters 76a and 76b that were separated by HPLC on silica gel. The preferred isomer 76b was treated with trifluoroacetic acid in methylene chloride to remove the 4-(2,4-dimethoxybenzyl) group to form 77. Hydrogenation of 77 with platinum in acetic acid afforded the saturated ester 78. The ester 78 was reacted with 2,3-dichloro-5,6-dicyanobenzoquinone using the procedure of Dolling, et al. *J. Amer. Chem. Soc.* 1988, 110, 3318–3319, to give the $\Delta^1$ ester 71. The 7-carboxamides 89–96 are prepared from the acid 88 which is made by saponifying the ester 71 (Example 64).

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

All temperatures given in the following examples are in degrees Celsius. $^1$H and $^{13}$C nuclear magnetic resonance (NMR) spectra were taken at 400 or 500 MHz at ambient temperature in the solvents indicated. Some abbreviations used herein are as follows: "Ac" represents an acetyl group, e.g., AcOH is acetic acid; "Bu" represents a butyl group; "conc." is an abbreviation for concentrated; "DMAP" is 4-dimethylaminopyridine; "DMF" is dimethylformamide; "DMSO" is dimethyl sulfoxide; "Et" represents an ethyl group; "HPLC" is high pressure liquid chromatography; "Me" represents a methyl group; "NMR", unless otherwise specified, refers to $^1$H nuclear magnetic resonance spectroscopy; "Ph" represents a phenyl group; "Tf" is —SO$_2$CF$_3$; "THF" is tetrahydrofuran, "TIPS" represents triisopropylsilyl. Unless otherwise specified, "tlc" and "TLC" refer to thin layer SiO$_2$ chromatography.

For reference, the numbering of the tricyclic ring system of compounds of structural formula I is shown below:

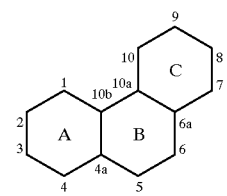

The stereochemical configurations depicted in the structures for the Examples detailed below are intended to denote only the relative configurations of the various stereogenic centers in the bicyclic and tricyclic ring systems. They are not intended to depict absolute configurations, unless the compound has been prepared from chiral (R)-(–) or (S)-(+) Wieland-Miescher ketone, which allows for assignment of absolute stereochemistry.

EXAMPLE 1

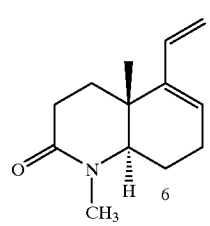

Step A: Preparation of 1

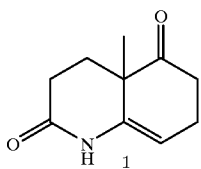

A mixture of 2-methyl-1,3-cyclohexandione (48 g, 0.369 moles), acrylamide (36 g, 0.491 moles), p-toluenesulfonic acid (3.0 g), and N,N-dimethylacetamide (200 mL) was stirred at 75O for 16 hrs, heated at reflux for 6.5 hrs, and stored at room temperature for 3 days. Cold water (200 mL) was added with stirring, and after a few minutes, the suspension was decanted from the sticky polymer. After storing at 4° C. for 30 hrs, the suspension was filtered; the solid washed with a little cold water and dried (vacuum oven, 60°) to give 1. NMR (CDCl$_3$): δ 1.29 (s, 3H); 5.10 (m, 1H); 8.32 (bs, 1H).

Step B: Preparation of 2

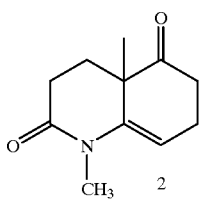

NaH (60% oil dispersion, 1.2 g., 30 mmoles) was added to a suspension of 1 (5.0 g., 27.9 mmoles) in a mixture of THF (70 mL) and DMF (30 mL) at 0°. After stirring for 1 hr at 0°, methyl iodide (1.9 mL, 30.5 mmoles) was added, the thick suspension that formed after a few minutes was broken up, and stirred at room temperature for 1 hr. The reaction was quenched with 1 N NH$_4$Cl solution and extracted twice with CH$_2$Cl$_2$. The extracts were washed with 1 N HCl, 10% NaHCO$_3$, water, and saturated NaCl solution and dried (MgSO$_4$). The residue from evaporation in vacuo was chromatographed on silica gel with EtOAc to give pure 2 as a yellow oil. NMR (CDCl$_3$): δ 1.33 (s, 3H); 3.19 (s, 3H); 5.30 (m, 1H).

Step C: Preparation of 3

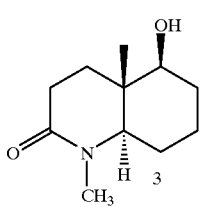

A solution of enone 2 (4.2 g, 21.7 mmole) and platinum oxide (850 mg) in 95% acetic acid (45 mL) was stirred under a balloon of hydrogen for 18 hours at room temperature. The mixture was filtered through a bed of CELITE™ diatomaceous earth and the filtrate concentrated in vacuo. The residue was dissolved in methylene chloride, dried over sodium sulfate and evaporated in vacuo to afford 3 as a solid. NMR (CDCl$_3$): δ 0.93 (s, 3H); 2.92 (s, 3H); 3.03 (dd, 1H); 3.32 (m, 1H).

Step D: Preparation of 4

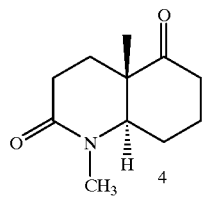

A mixture of alcohol 3 (3.56g, 18.0 mmole), N-methylmorpholine-N-oxide (3.27g, 27.0 mmole) and 4Å powdered molecular sieves (9.0g) in CH$_2$Cl$_2$ (35 mL), was treated with tetrapropylammonium perruthenate (326 mg, 0.9 mmole). The mixture was stirred at room temperature for one hour and filtered through a bed of CELITE™ diatomaceous earth, which was washed with CH$_2$Cl$_2$. The filtrate was concentrated in vacuo, and the residue chromatographed on silica gel with hexane-acetone (3:2) to afford 4 as a solid. NMR (CDCl$_3$): δ 1.29 (s, 3H); 3.00 (s, 3H); 3.38 (dd, 1H).

Step E: Preparation of 5

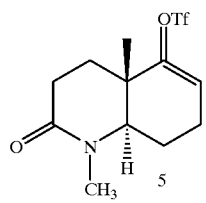

To a solution of the ketone 4 (7.48 g, 38.3 mmoles) in THF (250 mL) was added KN(SiMe$_3$)$_2$ (0.5 M in toluene, 84.3 mL, 42.2 mmoles) over 20 min with mechanical stirring in a N$_2$ atmosphere keeping the temperature below 10° with an ice bath. The suspension was stirred at 0° for 30 min, and PhN(SO$_2$CF$_3$)$_2$ (16.4 g, 45.9 mmoles) was added in several portions. After a few minutes the cold bath was removed, and the clear reaction was allowed to stir at room temperature for 1 hr. The reaction was quenched by addition of saturated NH$_4$Cl (30 mL); the precipitate was dissolved by addition of water, and most of the THF removed in vacuo. The residue was partitioned between water and EtOAc, and the aqueous phase extracted twice with EtOAc. The combined organic extracts were washed twice with water and saturated NaCl solution and dried (MgSO$_4$). The residue from evaporation in vacuo was purified by chromatography on silica gel with CH$_2$Cl$_2$—acetone (8:1) to afford 5. NMR (CDCl$_3$): δ 1.18 (s, 3H); 2.99 (s, 3H); 3.53 (dd, 1H); 5.72 (m, 1H).

Step F: Preparation of 6

A mixture of the enol triflate 5 (12.3 g, 37.6 mmoles), anhydrous LiCl (4.77 g, 113 mmoles), (n-Bu)3SnCH=CH$_2$ (11.9 mL, 40.7 mmoles), and (Ph$_3$P)$_4$Pd (867 mg, 2 mol %) in THF (260 ml) was heated under reflux in a N$_2$ atmosphere with magnetic stirring for 16 hrs. Most of the THF was removed in vacuo, and the residue was dissolved in EtOAc, washed with 10% NH$_4$OH, water (2×), and saturated brine and dried (MgSO$_4$). The residue from evaporation in vacuo was purified by chromatography on silica gel with hexane-isopropanol (8:1) to give 6 as a yellow oil. NMR (CDCl$_3$): δ 1.07 (s, 3H); 3.00 (s, 3H); 3.39 (dd, 1H); 5.00 (dd, 1H); 5.29 (dd, 1H); 5.72 (m, 1H); 6.25 (dd, 1H).

EXAMPLE 2

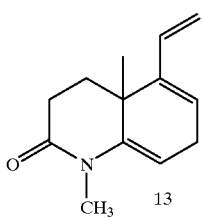

13

Step A: Preparation of 8

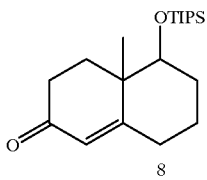

8

To a solution of the enone 7 (5.3 g, 28 mmoles; Tetrahedron 1995, 51, 3499–3506) and 2,6-lutidine (8.16 μL, 70 mmoles) in $CH_2Cl_2$ (56 mL) cooled in an ice bath was added over 15 min (iPrO)3SiOTf (11.2 mL, 41.9 mmoles). After stirring for 2 hrs in the ice bath, another 1.5 mL of (iPrO)3SiOTf was added. The mixture stirred for an additonal 1 hr., diluted with $CH_2Cl_2$ (30 mL), washed with cold 2N HCl, water (2×), and saturated brine and dried ($MgSO_4$). The residue after evaporation in vacuo was chromatographed on silica gel with hexane-EtOAc (10:1) to afford pure 8 as a colorless syrup. NMR ($CDCl_3$): δ 1.06 (d, 18H); 1.21 (s, 3H); 3.56 (m, 1H); 5.77 (d, 1H).

Step B: Preparation of 9

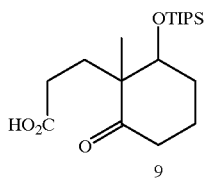

9

To a magnetically stirred mixture of the enone 8 (1.1 g, 3.27 mmoles), $Na_2CO_3$ (519 mg, 4.9 mmoles), water (2.5 mL) and tBuOH (19 mL) heated at 90° was added over 30 min a warm solution of $NaIO_4$ (4.9 g, 22.9 mmoles) and $KMnO_4$ (36 mg) in water (19 mL). A yellow brown solid formed in the two phase mixture. After heating under reflux for 2 hrs, the cooled mixture was filtered through a bed of CELITE™ diatomaceous earth. The solids were washed with water (2×). The filtrate and washes were evaporated in vacuo to remove most of the tBuOH. The aqueous phase was extracted with EtOAc and acidified with conc. HCl. The cloudy suspension was extracted with $CH_2Cl_2$ (4×). The combined extracts were washed with water (2×) and dried ($MgSO_4$). Evaporation in vacuo afforded 9 as a colorless syrup. NMR ($CDCl_3$): 1.07 (d, 18H); 1.14 (s, 3H); 3.97 (m, 1H).

Step C: Preparation of 10

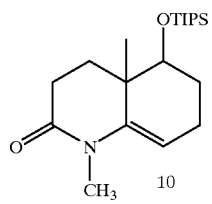

10

A mixture of the seco acid 9 (0.91 g, 2.55 mmoles), $MeNH_2.HCl$ (0.86 g, 12.7 mmoles), NaOAc (1.05 g, 12.8 nmmoles) and ethylene glycol (6 mL) was placed in an oil bath at 100° and with magnetic stirring in an $N_2$ atmosphere the temperature was raised to 1800 over 30 min. The mixture was kept at 1800 for 10 min, cooled, diluted with water, and extracted with $CH_2Cl_2$ (3×). The combined extracts were washed with water, 10% $NaHCO_3$ solution, and water and dried ($MgSO_4$). Evaporation in vacuo gave 10 as a yellow-brown syrup. NMR ($CDCl_3$): δ 1.07 (d, 18H); 1.10 (s, 3H); 3.11 (s, 3H); 3.75 (dd, 1H); 4.84 (m, 1H).

Step D: Preparation of 11

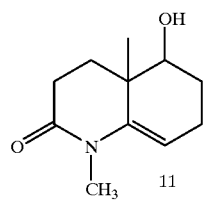

11

A solution of 10 (0.65 g, 1.85 mmoles) in 1.0 M $nBu_4NF$ in THF (9.5 mL) was kept a room temperature for 1 hr, diluted with water (20 mL), and acidified with 2 N HCl. Most of the THF was removed in vacuo, and the residual brown solution was extracted with $CH_2Cl_2$ (6×). The combined extracts were dried ($MgSO_4$). The residue after evaporation in vacuo was chromatographed on silica gel with EtOAc to afford pure 11. NMR ($CDCl_3$): δ 1.11 (s, 3H); 3.13 (s, 3H); 3.62 (m, 1H); 4.98 (m, 1H).

Step E: Preparation of 2

To a magnetically stirred mixture of 11 (0.31 g, 1.59 mmoles), N-methyl-morpholine-N-oxide (279 mg, 2.38 mmoles), powdered 4Å molecular sieves (785 mg) and $CH_2Cl_2$ (5 mL) at room temperature was added tetrapropylammonium perruthenate (28 mg, 0.077 mmole). There was a mild exotherm, and the suspension was stirred at room temperature for 45 min. It was chromatographed directly on silica gel with EtOAc to give 2, identical with the compound prepared in Example 1, Step B. NMR ($CDCl_3$): δ 1.32 (s, 3H); 3.18 (s, 3H); 5.39 (m, 1H).

Starting with (+)-7 derived from the (+)-(S)-Wieland-Miescher ketone, (−)-2 ($[α]_D$=−130° ($CHCl_3$, c=1.23)) was prepared by above sequence (Steps A–E).

Starting with (−)-7 derived from the (−)-(R)-Wieland-Miescher ketone, (+)-2 ($[α]_D$=+133°($CHCl_3$, c=1.24)) was prepared by above sequence (Steps A–E).

Step F: Preparation of 12

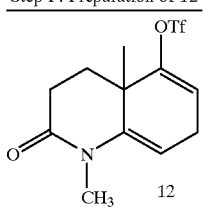

Using the procedure in Example 1, Step E, (±)-2 (6.54 g) was converted into (±)-12. NMR (CDCl₃): δ 1.39 (s, 3H); 3.18 (s, 3H); 5.12 (m, 1H); 5.84 (m, 1H).

Using the same procedure (−)-2 was converted into (−)-12 ([α]$_D$=−31.8° (CHCl₃, c=2.02)).

Using the same procedure (+)-2 was converted into (+)-12 ([α]$_D$=+32.9° (CHCl₃, c=2.04)).

Step G: Preparation of 13

Using the procedure in Example 1, Step F, (±)-12 (7.0 g) was converted into (±)-13. NMR (CDCl₃): δ 1.25 (s, 3H); 3.15 (s, 3H); 5.02 (dd, 1H); 5.11 (m, 1H); 5.37 (dd, 1H); 5.82 (m, 1H); 6.29 (dd, 1H).

Using the same procedure (−)-12 was converted into (−)-13 ([α]$_D$=−160° (CHCl₃, c=2.14)).

Using the same procedure (+)-12 was converted into (+)-13 ([α]$_D$=+163° (CHCl₃, c=2.12)).

EXAMPLE 3

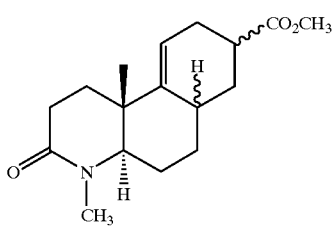

14a

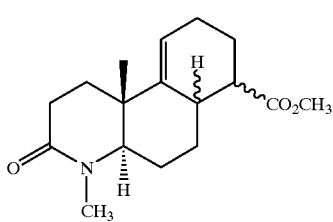

14b

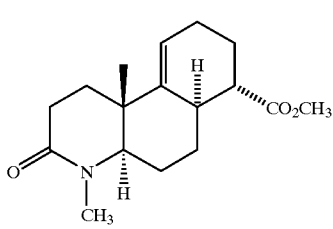

14c

A solution of 6 (43 mg) in methyl acrylate was heated at 100° for 48 hrs. Evaporation in vacuo and chromatography on silica gel with i-PrOH-hexane (1:9) gave 30 mg of a mixture of at least three isomers (14a and/or 14b) A, B, C in the ratio of 3.6:1.7:1, respectively. NMR (CDCl₃): Isomer A (probably 14c): δ 1.08 (s, 3H); 2.88 (s, 3H); 3.51 (dd, 1H); 3.69 (s, 3H); 5.59 (bs, 1H). Isomer B: δ 1.07 (s, 3H); 2.89 (s, 3H); 3.70 (s, 3H); 5.48 (m, 1H). Isomer C: δ 1.02 (s, 3H); 2.90 (s, 3H); 3.71 (s, 3H); 5.53 (bs, 1H).

EXAMPLE 4

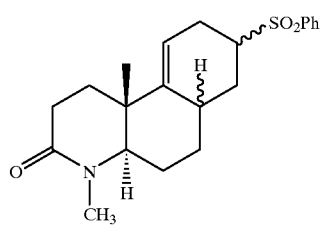

15a

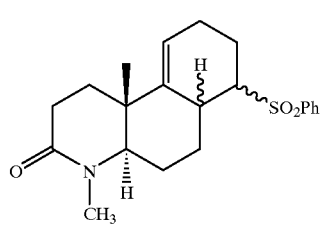

15b

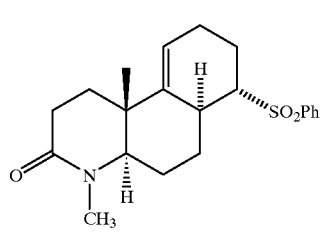

15c

A mixture of 6 (144 mg, 0.7 mmoles), phenylvinylsulfone (145 mg, 0.86 mmoles) in Cl₂CHCHCl₂ (0.5 mL) was heated in a pressure tube at 120° for 30 hrs. The cooled reaction was chromatographed directly on silica gel with hexane-ethyl acetate (1:1) to give 162 mg of a mixture of four isomers (15a and/or 15b). The two major isomers (A and B, ratio 2:1, respectively) were separated by HPLC (silica gel, hexane-iPrOH, 4:1). NMR (CDCl₃): Isomer A (probably 15c): δ 1.13 (s, 3H); 2.93 (s, 3H); 3.56 (dd, 1H); 7.70 (m, 2H); 7.69 (m, 1H); 7.90 (m, 2H). Isomer B: δ 1.04 (s, 3H); 2.90 (s, 3H); 5.51 (bs, 1H).

EXAMPLE 5

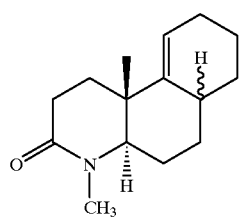

16a

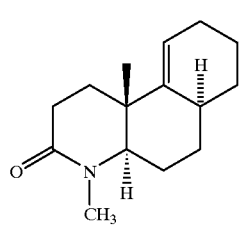

16b

The mixture of isomers 15a and 15b from Example 4 (25 mg), 6% Na/Hg (200 mg), Na₂HPO₄ (70 mg) in MeOH (0.5 mL) was stirred at room temperature for 20 hrs. The reaction was partitioned between EtOAc and water. The organic phase was dried (MgSO$_4$). The residue after evaporation in vacuo was purified by flash chromatography (hexane-EtOAc, 1:1) and HPLC (silica gel, hexane-iPrOH, 85:15) to give 16a as a single isomer, probably 16b, NMR (CDCl$_3$): δ 1.27 (s, 3H); 3.01 (s, 3H); 3.44 (dd, 1H); 4.94 (dd, 1H).

EXAMPLE 6

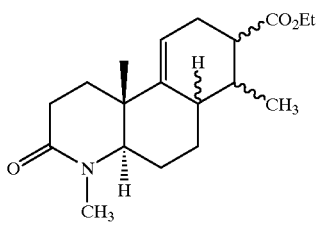
17a

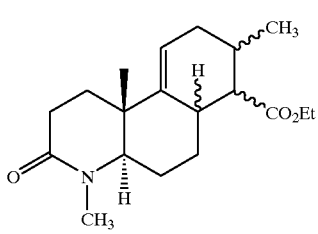
17b

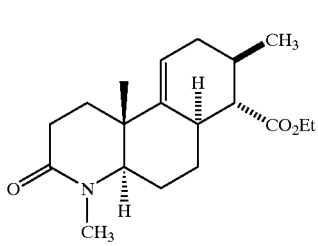
17c

A mixture of 6 (39 mg, 19 mmoles) and ethyl crotonate (0.2 mL) was heated at 100° for 2 days. Purification by flash chromatography and HPLC (silica gel, hexane-iPrOH, 85:15) gave 15 mg of a mixture of at least three isomers (17a and/or 17b) A, B, C in the ratio of 7:2:1, respectively. NMR (CDCl$_3$): Isomer A (probably 17c): δ 0.92 (d, J=5.9 Hz, 3H); 1.29 (t, J=7.1 Hz, 3H); 2.90 (s, 3H); 3.52 (dd, 1H); 4.20 (q, J=7.1 Hz, 2H); 5.57 (m, 1H). Isomer B: δ 0.92 (d, J=5.9 Hz, 3H); 1.30 (t, J=7.1, 3H); 2.93 (s, 3H); 3.04 (dd, 1H); 5.50 (m, 1H). Isomer C: δ 0.98 (d, J=5.9, 3H); 2.92 (s, 3H); 5.46 (m, 1H).

EXAMPLE 7

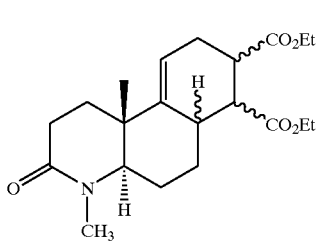
18a

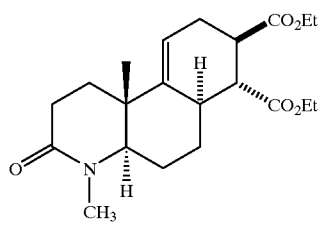
18b

A solution of 6 (105 mg, 0.51 nmmole) and diethyl fumarate (150 mg, 0.87 mmoles) in xylenes (0.5 mL) was heated at 95° for 18 hrs. Purification by flash chromatography (silica gel, hexane-iPrOH, 4:1) afforded 150 mg of three isomers (18a) A, B, and C in the ratio of 5:2:1. NMR (CDCl$_3$): Isomer A (probably 18b): δ 1.12 (s, 3H); 2.90 (s, 3H); 3.50 (dd, 1H); 5.63 (bs, 1H). Isomer B: δ 1.04 (s, 3H); 2.95 (s, 3H); 3.06 (dd, 1H); 5.56 (bs, 1H). Isomer C: δ 1.09 (s, 3H); 2.94 (s, 3H); 5.49 (m, 1H).

EXAMPLE 8

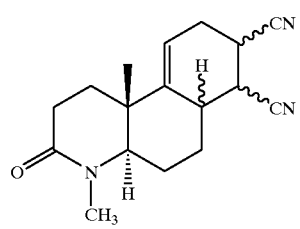
19a

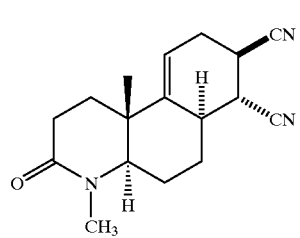
19b

A mixture of 6 (96 mg, 0.47 mmoles) and fumaronitrile (37 mg, 0.47 mmoles) was heated at 60° for 1 hr. Purification by flash chromatography (silica gel, hexane-iPrOH, 85:15) gave 105 mg of a mixture of isomers (19a) in the ratio of 8:1:1. NMR (CDCl$_3$) of the major isomer (probably 19b): δ 1.13 (s, 3H); 2.93 (s, 3H); 3.48 (dd, 1H); 5.73 (m, 1H).

EXAMPLE 9

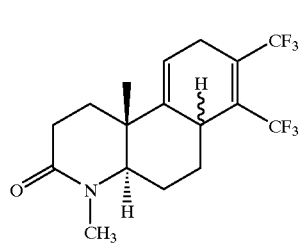
20a

EXAMPLE 11

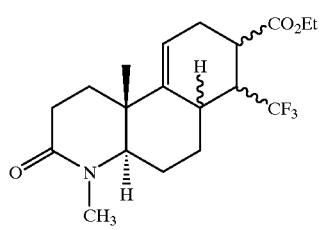
22a

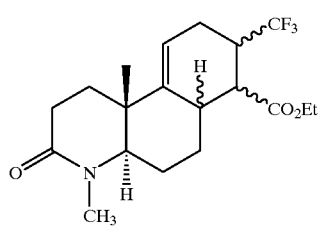
22b

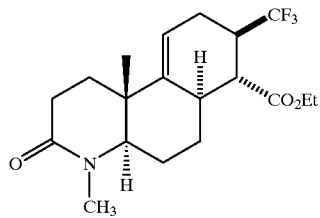
22c

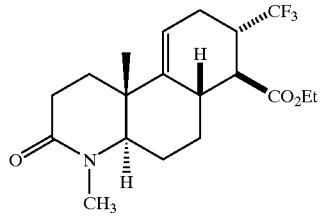
22d

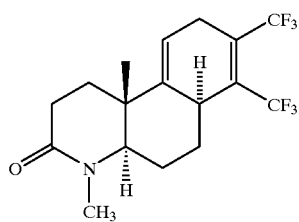
20b

Into a pressure tube cooled to -78° containing 6 (40 mg) was condensed hexafluoro-2-butyne (~2 mL). The suspension was stirred at room temperature for 16 hrs. The residue after evaporation was purified by preparative TLC (silica gel, hexane-iPrOH, 9:1) to give 100 mg of a mixture of isomers 20a in a ratio of 9:1. NMR (CDCl$_3$) of the major isomer (probably 20b): δ 1.17 (s, 3H); 2.94 (s, 3H); 3.71 (dd, 1H); 5.58 (bs, 1H).

EXAMPLE 10

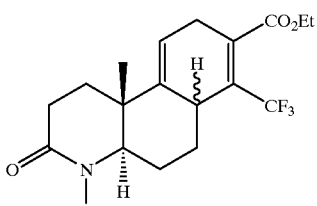
21a

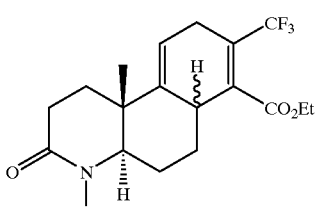
21b

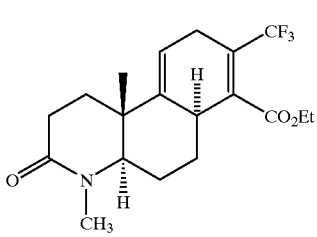
21c

A mixture of 6 (200 mg, 0.98 mmoles) and ethyl 4,4,4-trifluoro-2-butynoate (200 mg, 1.2 mmoles) spontaneously reacted with a strong exotherm. After a few minutes the mixture was warmed at 60° for 15 min. The material was purified by flash chromatography (silica gel, hexane-EtOAc, 4:1) to give a mixture of two isomers (21a and/or 21b) A and B in the ratio of 4:1, respectively. NMR (CDCl$_3$): Isomer A (probably 21c): δ 1.15 (s, 3H); 2.92 (s, 3H); 3.58 (dd, 1H); 5.65 (m, 1H). Isomer B: δ 1.08 (s, 3H); 2.94 (s, 3H); 3.06 (dd, 1H); 5.50 (m, 1H).

A solution of 6 (1.55 g, 7.56 mmoles), ethyl 4,4,4-trifluorocrotonate (1.36 mL, 9.10 mmoles) in benzene (5 mL) was heated in a pressure tube at 930 with magnetic stirring for 40 hrs. The residue from evaporation in vacuo was chromatographed (silica gel, hexane-iPrOH, 4:1) to give 1.91 g of an inseparable mixture of three isomers (22a and 22b) A, B, and C in the ratio of 7:2:1, respectively. NMR (CDCl$_3$): Isomer A (22c): δ 1.11 (s, 3H); 1.29 (t, 3H); 2.90 (s, 3H); 3.51 (dd, 1H); 4.21 (q, 2H); 5.60 (m, 1H). Isomer B (22d): δ 1.05 (s, 3H); 1.30 (t, 3H); 2.94 (s, 3H); 3.05 (dd, 1H); 4.22 (q, 2H); 5.54 (m, 1H). Isomer C: δ 1.06 (s, 3H); 2.93 (s, 3H); 5.49 (m, 1H).

EXAMPLE 12

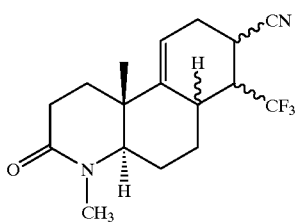
23a

51

-continued

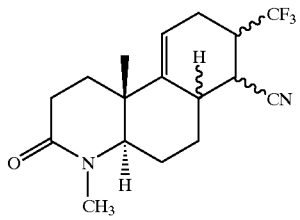
23b

A solution of 6 (118 mg, 0.574 mmole) and ethyl 4,4,4-trifluoro-2-cyanocrotonate [C. Ates et al, *Tet.Lett,* 34, 5711–14 (1993), 172 mg, 0.689 mmole] in benzene (0.5 mL) was heated in a sealed tube at 1000 for 18 hours. The mixture was cooled, evaporated in vacuo and flash chromatographed (silica gel, hexane:iPrOH, 4:1) to afford a mixture of 2 isomers, ratio 1.22:1. NMR (CDCl₃): Major isomer δ 1.20 (s, 3H); 1.39 (t, 3H); 2.93 (s, 3H); 3.45 (dd, 1H); 4.36 (m, 2H); 5.74 (s, 1H). Minor isomer: δ 1.07 (s, 3H); 1.39 (t, 3H); 2.97 (s, 3H); 3.14 (dd, 1H); 4.36 (m, 2H); 5.70 (s, 1H).

A solution of the above mixture of two isomers (120 mg, 0.30 mmole) and KOAc (58 mg, 0.690 mmole) in DMSO (1.0 mL) was stirred at 150° in a N₂ atmosphere for 2 hrs. The cooled mixture was partitioned with CH₂Cl₂-water, and the organic phase was washed with water, saturated brine, dried (MgSO₄) and concentrated in vacuo to give a mixture of four isomers (23a and 23b) A, B, C and D in the ratio of 1.56:1.11:1.06:1, respectively. NMR (CDCl₃): Isomer A: δ 1.20 (s, 3H); 2.94 (s, 3H); 3.45 (dd, 1H); 5.75 (s, 1H). Isomer B: δ 1.04 (s, 3H); 2.98 (s, 3H); 3.17 (dd, 1H); 5.70 (s, 1H). Isomer C: δ 1.06 (s, 3H); 2.98 (s, 3H); 3.50 (dd, 1H); 5.58 (s, 1H). Isomer D: δ 1.15 (s, 3H); 2.95 (s, 3H); 3.08 (dd, 1H); 5.68 (s, 1H).

EXAMPLE 13

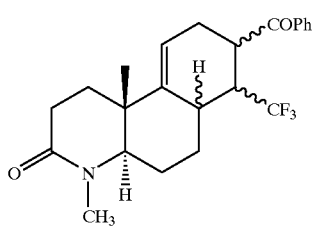
24a

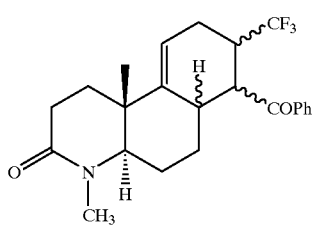
24b

52

-continued

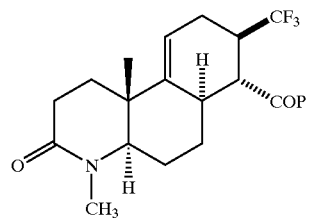
24c

Using the method of Example 12, 4,4,4-trifluoro-1-oxo-1-phenyl-2-butene [C. Ates et al, *Tet.Lett,* 34, 5711–14 (1993)] and 6 were reacted to give a mixture of three isomers (24a and/or 24b) A, B, and C in the ratio of 2:1:1, respectively. Flash chromatography and HPLC (silica gel, iPrOH:hexane (15:85) gave pure isomer A and a mixture of isomers B and C. NMR (CDCl₃): Isomer A (probably 24c): δ 1.15 (s, 3H); 2.87 (s, 3H); 3.42 (t, 1H); 3.51 (dd, 1H); 5.67 (s, 1H); 7.50–8.00 (m, 5H). Isomer B: δ 1.06 (s, 3H); 2.90 (s, 3H); 4.07 (dd, 1H); 3.42 (t, 1H); 5.56 (s, 1H); 7.50–8.00 (m, 5H). Isomer C: δ 1.08 (s, 3H); 2.90 (s, 3H); 3.42 (t, 1H); 3.02 (dd, 1H); 5.61 (s, 1H); 7.50–8.00 (m, 5H).

EXAMPLE 14

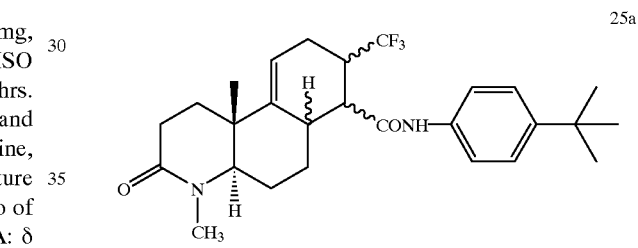
25a

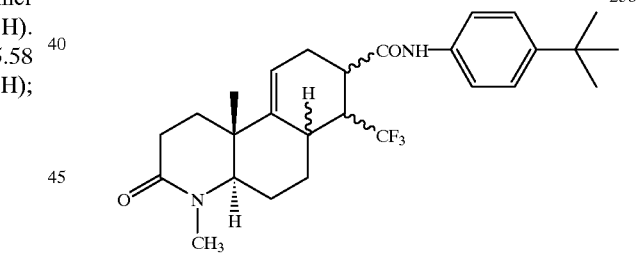
25b

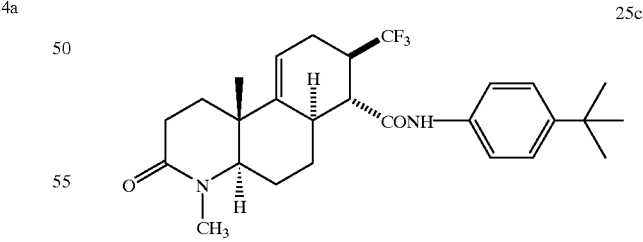
25c

Step A: Preparation of 4,4,4-Trifluorocrotonic acid

A solution of ethyl 4,4,4-trifluorocrotonate (9.85g, 65.9 mmole) and 1N NaOH (92.3 mL, 92.3 mmole) in THF (24 mL) was stirred at room temperature for 3 hours. The pH was brought to 1 with conc. HCl and the mixture extracted with Et₂O (3×). The combined extracts were dried (MgSO₄) and concentrated in vacuo to afford the title compound as an oil. NMR (CDCl₃): δ 6.55 (d, 1H); 6.89 (dq, 1H).

Step B: Preparation of N-(4'-(t-butyl)phenyl)-4,4,4-trifluorocrotonamide

A solution of 4,4,4-trifluorocrotonic acid (300 mg, 1.90 mmole), t-butylaniline (371 μL, 2.28 mmole), 1-(3-dimethylamino-propyl)-3-ethylcarbodiimide hydrochloride (510 mg, 2.66 mmole) and DMAP (8 mg) in CH₂Cl₂ (5 mL) was stirred at room temperature for 18 hrs. The mixture was diluted with CH₂Cl₂, washed with 1N NaOH, water, 1N HCl, 10% NaHCO₃ and dried (MgSO₄). Evaporation in vacuo to gave the title compound as a white solid. NMR (CDCl₃): δ 1.33 (s, 9H); 6.63 (d, 1H); 6.90 (dq, 1H); 7.37 (s, 1H); 7.39 (d, 2H); 7.51 (d, 2H).

Step C: Preparation of 25a/25b

A solution of N-(4'-(butyl)phenyl)-4,4,4-trifluorocrotonamide (159 mg, 0.585 mmole) and the 6 (100 mg, 0.487 mmole) in benzene (0.5 mL) was heated in a sealed tube at 100° for 40 hrs. After cooling and evaporation in vacuo, the crude product was chromatographed (silica gel, iPrOH:hexane, 15:85) to give 25a/25b as a mixture of three isomers. The isomers were separated by reverse phase HPLC eluting with acetonitrile:water (55:45) to give three isomers A, B and C. NMR (CDCl₃): Isomer A (probably 25c): δ 1.08 (s, 3H); 1.33 (s, 9H); 2.95 (s, 3H); 3.07 (dd, 1H); 5.56 (s, 1H); 7.23 (s, 1H); 7.39 (d, 2H); 7.47 (d, 2H). Isomer B: δ 1.14 (s, 3H); 1.33 (s, 9H); 2.90 (s, 3H); 3.54 (dd, 1H); 5.62 (s, 1H); 7.37 (s, 1H); 7.39 (d, 2H); 7.45 (d, 2H). Isomer C: δ 1.09 (s, 3H); 1.32 (s, 9H); 2.93 (s, 3H); 3.06 (dd, 1H); 5.58 (s, 1H); 7.33 (s, 1H); 7.37 (d, 2H); 7.46 (d, 2H).

EXAMPLE 15

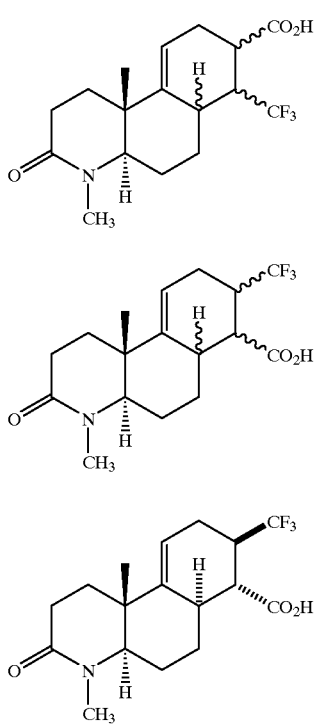

The mixture of the isomers 22a and 22b (Example 11) (2.32 g) and 5N NaOH in MeOH (100 mL) was heated under reflux in a N₂ atmosphere for 4 hrs. Most of the MeOH was removed in vacuo and water (25 mL) was added. The clear solution was extracted with diethyl ether and acidified with conc. HCl. The suspension was aged for 30 min at room temperature. The solid was filtered, washed with water (3×10 mL) and dried (vacuum over, 45°) to give a mixture of three isomers (26a and/or 26b) A, B, and C in the ratio of 7:2:1, respectively. Small amounts of isomer A (26c) could be obtained by fractional recrystallization of the isomeric mixture from CHCl₃-Et₂O and MeOH. NMR (CDCl₃): δ 1.11 (s, 3H); 2.91 (s, 3H); 3.53 (dd, 1H); 5.61 (bs, 1H).

EXAMPLE 16

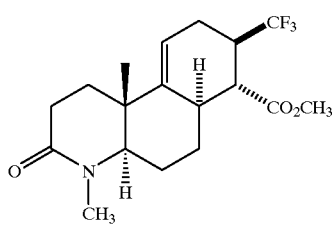

To a solution of 26c (15 mg, 044 mmoles) in toluene (0.35 mL) and MeOH (0.1 mL) was added Me₃SiCHN₂ (2 M in hexane, 50 μL) with magnetic stirring at room temperature. After a few minutes the yellow solution was evaporated in vacuo to give 27. NMR (CDCl₃): δ 1.12 (s, 3H); 2.91 (s, 3H); 3.52 (dd, 1H); 3.75 (s, 3H); 5.60 (bs, 1H).

EXAMPLE 17

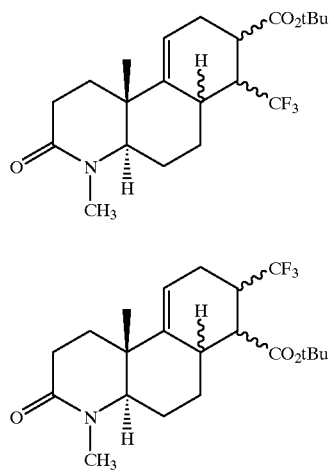

The mixture of acid isomers 26a and 26b (Example 15) (35 mg, 0.1 mmole) and N,N'-diisopropyl-O-t-butylisourea (50 μL) in CH₂Cl₂ (0.4 mL) and MeOH (50 μL) was stirred at room temperature for 24 hrs. The solid was filtered and washed with CH₂Cl₂ (2×0.5 mL). The residue from evaporation in vacuo of the filtrate was chromatographed (silica gel, hexane-iPrOH, 4:1) to give a mixture of three isomers (28a and/or 28b) A, B, and C in the ratio 7:2:1, respectively. NMR (CDCl₃): isomer A: δ 1.11 (s, 3H); 1.15 (s, 9H); 2.90 (s, 3H); 3.50 (dd, 1H); 5.59 (bs, 1H). isomer B: 3 1.05 (s, 3H); 1.16 (s, 9H); 2.95 (s, 3H); 3.04 (dd, 1H); 5.52 (m, 1H). isomer C: δ 1.06 (s, 3H); 5.47 (m, 1H).

EXAMPLE 18

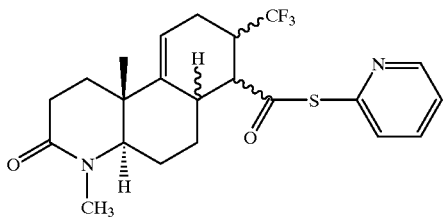

29a

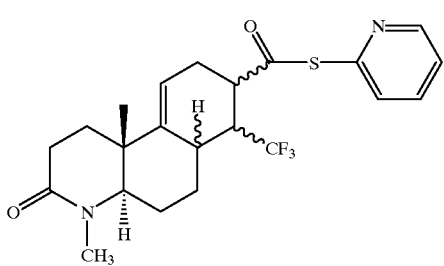

29b

A suspension of the mixture of acid isomers 26a and 26b (Example 15) (129 mg, 0.37 mmole), Ph₃P (196 mg, 0.74 mmoles), and 2,2'-dithiodipyridine (164 mg, 0.74 mmoles) in toluene (1.5 mL) was stirred at room temperature for 20 hrs. The mixture was chromatographed directly (silica gel, hexane-iPrOH, 4:1) to give 72 mg of a mixture of three isomers (29a and/or 29b) A, B, and C in the ratio 5:4:1. NMR (CDCl₃): isomer A: δ 1.15 (s, 3H); 2.90 (s, 3H); 3.47 (m, 1H); 5.62 (bs, 1H); 7.31 (m, 1H); 7.60 (m, 1H); 7.77 (m, 1H); 8.63 (m, 1H). isomer B: δ 1.03 (s, 3H); 2.95 (s, 3H); 3.08 (dd, 1H); 5.55 (m, 1H); 7.31 (m, 1H); 7.60 (m, 1H); 7.77 (m, 1H); 8.63 (m, 1H). isomer C: δ 1.05 (s, 3H); 2.92 (s, 3H); 3.32 (dd, 1H); 5.50 bs, 1H); 7.31 (m, 1H); 7.60 (m, 1H); 7.77 (m, 1H); 8.63 (m, 1H).

EXAMPLE 19

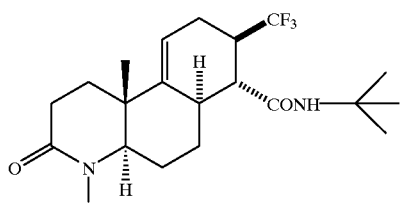

30a

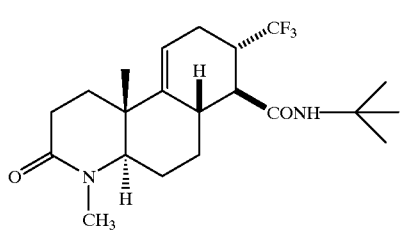

30b

To a suspension of the mixture of acid isomers 26a and 26b (Example 15) (1.20 g, 3.48 mmoles) and pyridine (0.34 mL, 4.17 mmoles) in CH₂Cl₂ (17 mL) cooled to 10° was added dropwise oxalyl chloride (0.36 mL, 4.17 mmoles). After the vigorous gas evolution subsided, the mixture was stirred at room temperature for 3 hrs. The CH₂Cl₂ was removed in vacuo, and the residue triturated with EtOAc (15 mL) and filtered. The solid was washed with EtOAc (2×10 mL). The filtrate and washes were evaporated in vacuo to afford a crude mixture of acid chloride isomers.

A solution of above acid chloride isomer mixture (464 mg, 1.16 mmoles) in dry THF (2.9 mL) was added quickly to a solution of t-butylamine (146 μL, 1.39 mmoles), pyridine (120 μL, 1.54 mmoles) and DMAP (30 mg) in dry THF (3 mL). The mixture was stirred at room temperature for 36 hrs and then warmed at 55° for 30 min. The cooled reaction was treated with 0.5 N NaOH (9 mL). After stirring at room temperature for 15 min, the mixture was diluted with water (40 mL) and extracted with CHCl₃ (4×). The combined extracts were washed with 0.5 N HCl (2×), water (2×) and dried (MgSO₄). Evaporation in vacuo gave a mixture of the t-butylamide isomers 30a and 30b in the ratio of 3:2. The mixture was separated by preparative HPLC (silica gel, hexane-iPrOH, 3:1) to give pure samples of both isomers. Detailed NMR analysis including COSY, NOESY, and HMQC techniques established the regio- and stereochemistry of the isomers as 30a for the major, less polar isomer, and 30b for the minor, more polar isomer. NMR (CDCl₃): 30a: δ 1.08 (s, 3H, 10b-Me); 1.36 (s, 9H, t-Bu); 2.88 (s, 3H, NMe); 3.50 (dd, J=6.8, 12.1 Hz, 1H, 4a-H); 5.54 (dt, J=5.2, 2.6 Hz, 10-H); 5.56 (s, 1H, NH). 30b: δ 1.04 (s, 3H, 10b-Me); 1.37 (s, 9H, t-Bu); 2.93 (s, 3H, NMe); 3.01 (dd J=3.3, 12.5 Hz, 1H, 4a-H); 5.49 (dt, J=6.0, 2.2 Hz, 10-H); 5.54 (s, 1H, NH).

EXAMPLE 20

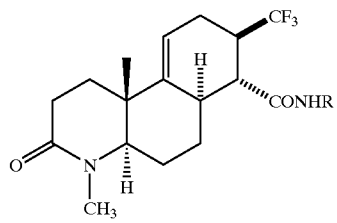

31a

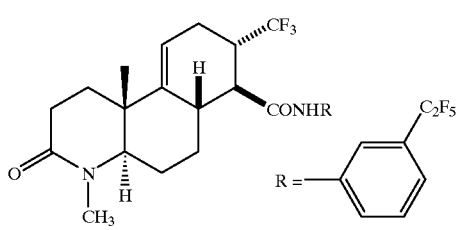

31b

Using the procedure in Example 19, 3-(pentafluoroethyl)-aniline was reacted with the acid chloride isomer mixture to give a mixture of the anilides 31a and 31b in the ratio of 2:1. Recrystallization from CH₃CN gave a pure sample of the major, less polar isomer 31a.

NMR (CDCl₃): δ 1.12 (s, 3H); 2.89 (s, 3H); 3.52 (dd, 1H); 5.62 (bs, 1H); 7.37 (d, 1H); 7.46 (t, 1H); 7.74 (d, 2H); 7.79 (d, 1H). Preparative HPLC (Zorbax RxC8, CH₃CN-water, 55:45) gave a nearly pure sample of the minor, more polar isomer 31b. NMR (CDCl₃): δ 1.07 (s, 3H); 2.95 (s, 3H); 3.07 (dd, 1H); 5.56 (m, 1H); 7.38 (d, 1H); 7.48 (t, 1H); 7.53 (t, 1H); 7.72 (d, 2H);

7.80 (d, 1H).

EXAMPLE 21

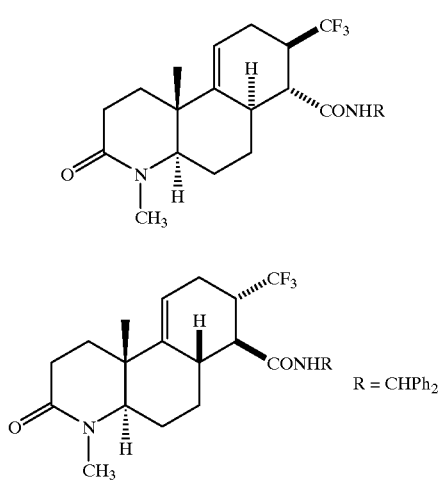

Using the procedure in Example 19, aminodiphenylmethane was reacted with the acid chloride isomer mixture to give a mixture of the amides 32a and 32b in the ratio of 3:2, respectively. NMR (CDCl$_3$): 32a: δ 1.09 (s, 3H); 2.87 (s, 3H); 3.46 (dd, 1H); 5.57 (bs, 1H); 6.29 (m, 1H); 6.43 (m, 1H); 7.17–7.48 (m, 10H). 32b: δ 1.01 (s, 3H); 2.93 (s, 3H); 3.00 (dd, 1H); 5.50 (bs, 1H); 6.29 (m, 1H); 6.43 (m, 1H); 7.17–7.48 (m, 10H).

EXAMPLE 22

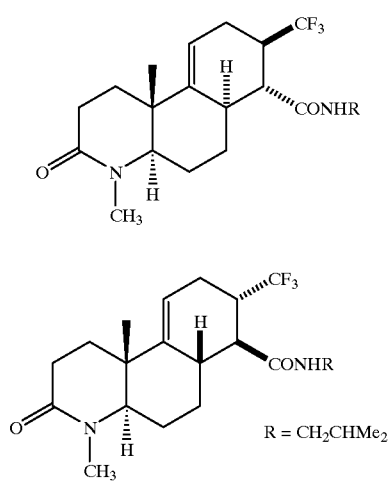

Using the procedure in Example 19, isobutylamine was reacted with the acid chloride isomer mixture to give a mixture of the amides 33a and 33b in the ratio of 3:2, respectively NMR (CDCl$_3$): 33a: δ 0.94 (d, 6H); 1.11 (s, 3H); 2.90 (s, 3H); 3.15 (m, 2H); 3.54 (dd, 1H); 5.59 (bs, 1H); 5.65 (m, 1H). 33b: δ 0.95 (d, 6H); 1.06 (s, 3H); 2.95 (s, 3H); 3.15 (m, 2H); 3.04 (dd, 1H); 5.53 (m, 1H); 5.65 (m, 1H).

EXAMPLE 23

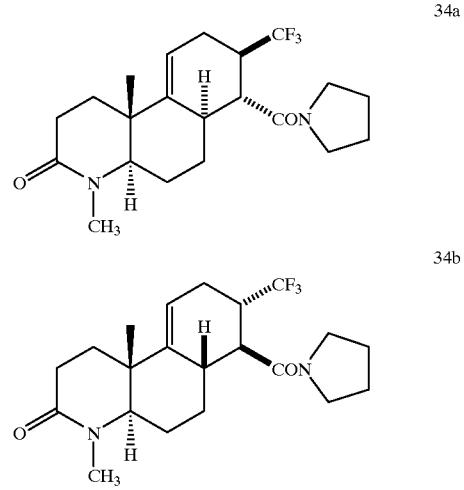

Using the procedure in Example 19, pyrrolidine was reacted with the acid chloride isomer mixture to give a mixture of the amides 34a and 34b in the ratio of 7:3, respectively. NMR (CDCl$_3$): 34a: δ 1.12 (s, 3H); 2.89 (s, 3H); 5.59 (bs, 1H). 34b: δ 1.05 (s, 3H); 2.93 (s, 3H); 3.03 (dd, 1H); 5.52 (m, 1H).

EXAMPLE 24

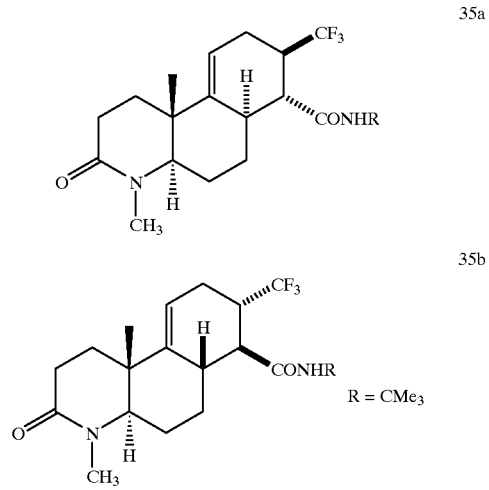

Using the procedure in Example 19, t-butylamine was reacted with the acid chloride isomer mixture to give a mixture of the amides 35α and 35b in the ratio of 7:3 NMR (CDCl$_3$): 35α: δ 1.11 (s, 3H); 1.36 (s, 9H); 2.91 (s, 3H); 3.53 (dd, 1H); 5.40 (s, 1H); 5.56 (bs, 1H). 35b: δ 1.05 (s, 3H); 1.36 (s, 9H); 2.96 (s, 3H); 3.04 (dd, 1H); 5.42 (s, 1H); 5.50 (m, 1H).

EXAMPLE 25

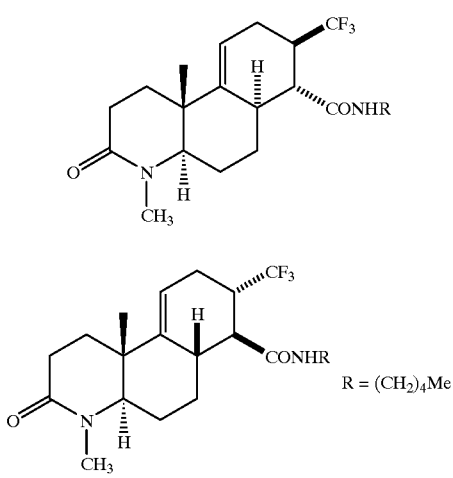

Using the procedure in Example 19, n-pentylamine was reacted with the acid chloride isomer mixture to give a mixture of the amides 36a and 36b in the ratio of 2:1, respectively. NMR (CDCl₃): 36a: δ 0.90 (t, 3H); 1.10 (s, 3H); 2.89 (s, 3H); 3.51 (dd, 1H); 5.57 (bs, 1H); 5.63 (bs, 1H). 36b: δ 0.90 (t, 3H); 1.03 (s, 3H); 2.92 (s, 3H); 3.02 (dd, 1H); 5.50 (s, 1H); 5.63 (m, 1H).

EXAMPLE 26

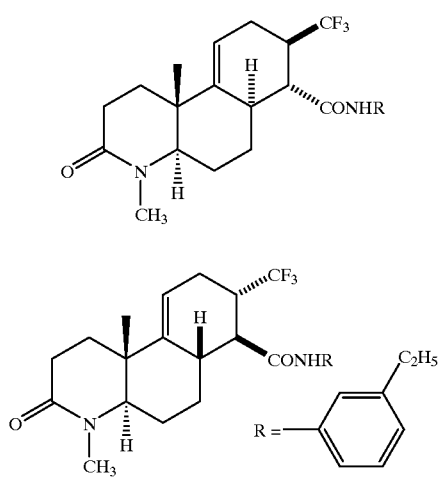

Using the procedure in Example 19, 3-ethylaniline was reacted with the acid chloride isomer mixture to give a mixture of the anilides 37a and 37b in the ratio of 2:1, respectively. NMR (CDCl₃): 37a: δ 1.15 (s, 3H); 1.26 (t, 3H); 2.67 (q, 2H); 2.90 (s, 3H); 3.54 (dd, 1H); 5.63 (s, 1H); 7.02–7.41 (m, 4H). 37b: δ 1.08 (s, 3H); 1.26 (t, 3H); 2.67 (q, 2H); 2.95 (s, 3H); 3.08 (dd, 1H); 5.56 (s, 1H); 7.02–7.41 (m, 4H).

EXAMPLE 27

Using the procedure in Example 19, 4-trifluoromethylaniline was reacted with the acid chloride isomer mixture to give a mixture of the anilides 38a and 38b in the ratio of 2:1, respectively. NMR (CDCl₃): 38a: δ 1.15 (s, 3H); 2.91 (s, 3H); 3.57 (dd, 1H); 5.64 (s, 1H); 7.62 d, 2H); 7.68 (d, 2H). 38b: δ 1.09 (s, 3H); 2.95 (s, 3H); 3.06 (dd, 1H); 5.57 (s, 1H); 7.62 (d, 2H); 7.68 (d, 2H).

EXAMPLE 28

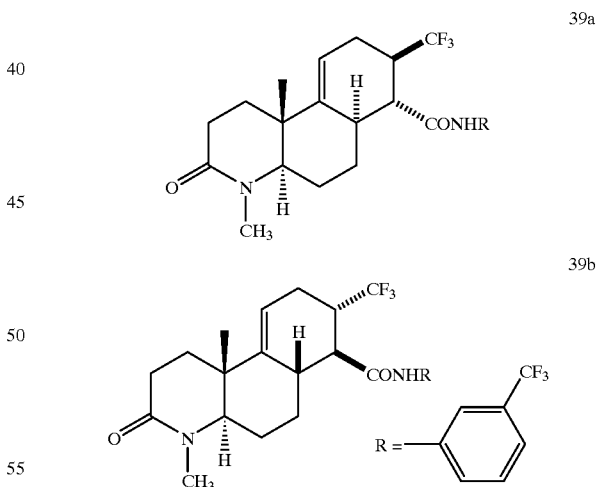

Using the procedure in Example 19, 3-trifluoromethylaniline was reacted with the acid chloride isomer mixture to give a mixture of the anilides 39a and 39b in the ratio of 2:1, respectively. NMR (CDCl₃): 39a: δ 1.15 (s, 3H); 2.91 (s, 3H); 3.56 (dd, 1H); 5.64 (s, 1H); 7.43–7.84 (m, 4 H). 39b: δ 1.09 (s, 3H); 2.95 (s, 3H); 3.07 (dd, 1H); 5.57 (s, 1H); 7.43–7.8 (m, 4H).

EXAMPLE 29

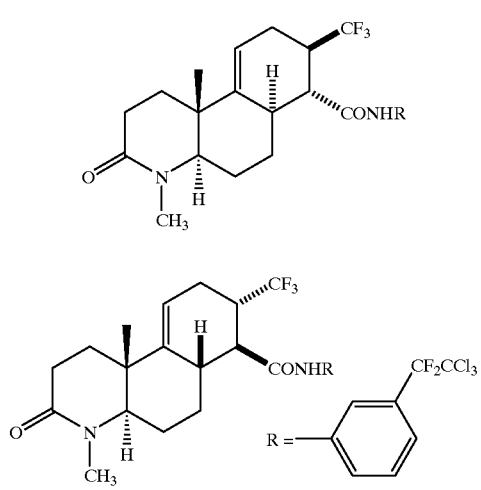

Using the procedure in Example 19, 3-(2,2,2-trichloro-1,1-difluroethyl)aniline was reacted with the acid chloride isomer mixture to give a mixture of the anilides 40a and 40b in the ratio of 2:1, respectively. NMR (CDCl$_3$): 40a: δ 1.15 (s, 3H); 2.91 (s, 3H); 3.55 (dd, 1H); 5.64 (s, 1H); 7.46–7.88 (m, 4 H). 40b: δ 1.08 (s, 3H); 2.95 (s, 3H); 3.07 (dd, 1H); 5.57 (s, 1H); 7.46–7.88 (m, 4H).

EXAMPLE 30

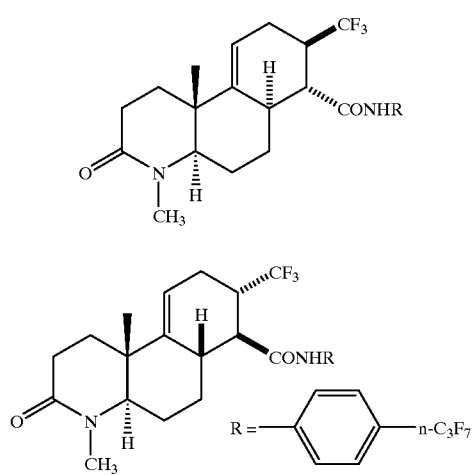

Using the procedure in Example 19, 4-(heptafluoropropyl)aniline was reacted with the acid chloride isomer mixture to give a mixture of the anilides 38a and 38b in the ratio of 1.7:1, respectively. NMR (CDCl$_3$): 38a: δ 1.15 (s, 3H); 2.91 (s, 3H); 3.56 (dd, 1H); 5.64 (s, 1H); 7.31–8.13 (m, 4H). 38b: δ 1.09 (s, 3H); 2.95 (s, 3H); 3.07 (dd, 1H); 5.58 (s, 1H); 7.31–8.13 (m, 4H).

EXAMPLE 31

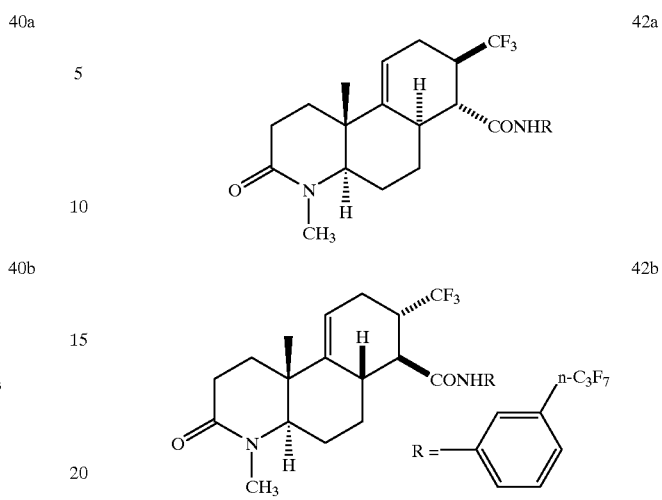

Using the procedure in Example 19, 3-(heptafluoropropyl)aniline was reacted with the acid chloride isomer mixture to give a mixture of the anilides 42a and 42b in the ratio of 1.6:1, respectively. NMR (CDCl$_3$): 42a: δ 1.15 (s, 3H); 2.91 (s, 3H); 3.55 (dd, 1H); 5.64 (s, 1H); 7.39–7.84 (m, 4H). 42b: δ 1.09 (s, 1H); 2.95 (s, 3H); 3.07 (dd, 1H); 5.57 (s, 1H); 7.39–7.84 (m, 4H).

EXAMPLE 32

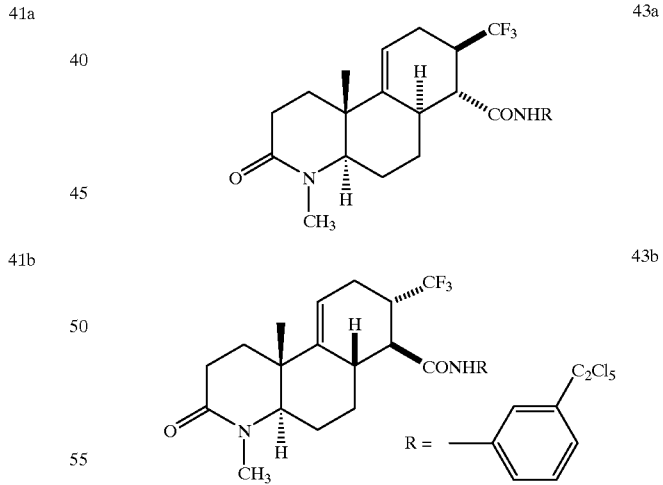

Using the procedure in Example 19, 3-(pentachloroethyl)aniline was reacted with the acid chloride isomer mixture to give a mixture of the anilides 43a and 43b in the ratio of 1.85:1, respectively. NMR (CDCl$_3$): 43a: δ 1.15 (s, 3H); 2.91 (s, 3H); 3.55 (dd, 1H); 5.64 (s, 1H); 7.38–8.20 (m, 4H). 43b: δ 1.08 (s, 3H); 2.95 (s, 3H); 3.07 (dd, 1H); 5.57 (s, 1H); 7.38–8.20 (m, 4H).

EXAMPLE 33

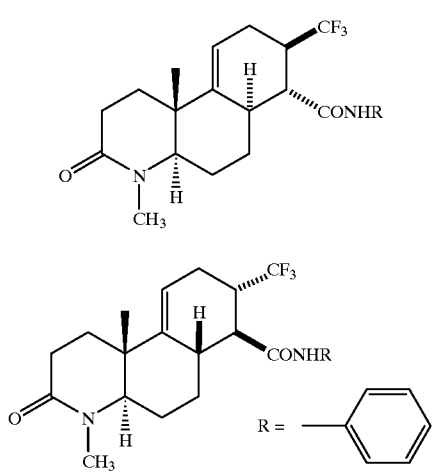

Using the procedure in Example 19, aniline was reacted with the acid chloride isomer mixture to give a mixture of the anilides 44a and 44b in the ratio of 2.7:1, respectively. NMR (CDCl$_3$): 44a: δ 1.15 (s, 3H); 2.90 (s, 3H); 3.54 (dd, 1H): 5.63 (s, 1H): 7.16–7.53 (m, 5H). 44b: δ 1.09 (s, 3H); 2.95 (s, 3H); 3.06 (dd, 1H); 5.57 (s, 1H); 7.16–7.53 (m, 5H).

EXAMPLE 34

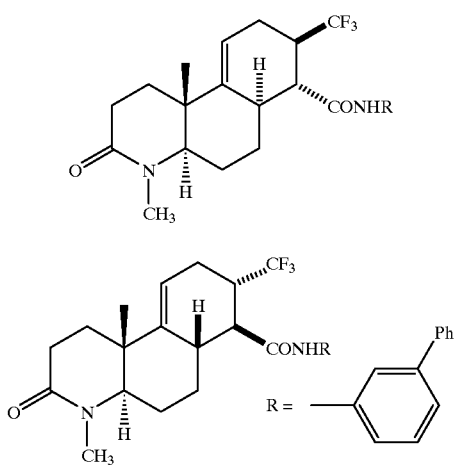

Using the procedure in Example 19, 3-aminobiphenyl was reacted with the acid chloride isomer mixture to give a mixture of the anilides 45a and 45b in the ratio of 2.5:1, respectively. NMR (CDCl$_3$): 45a: δ 1.15 (s, 3H); 2.90 (s, 3H); 3.55 (dd, 1H); 5.63 (s, 1H); 7.36–7.80 (m, 4H). 45b: δ 1.09 (s, 3H); 2.95 (s, 3H); 3.06 (dd, 1H); 5.58 (s, 1H); 7.36–7.80 (m, 4H).

EXAMPLE 35

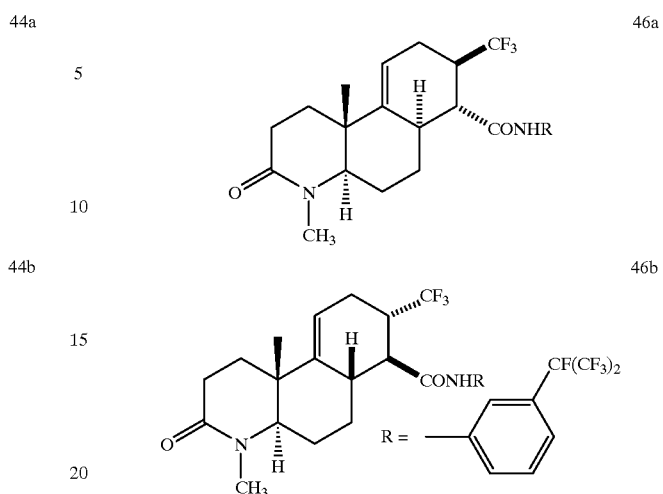

Using the procedure in Example 19, 3-(heptafluoroisopropyl)aniline was reacted with the acid chloride isomer mixture to give a mixture of the anilides 46a and 46b in the ratio of 2.6:1, respectively. NMR (CDCl$_3$): 46a: δ 1.15 (s, 3H); 2.91 (s, 3H); 3.55 (dd, 1H); 5.64 (s, 1H); 7.41–7.81 (m, 4H). 46b: δ 1.09 (s, 3H); 2.95 (s, 3H); 3.07 (dd, 1H); 5.58 (s, 1H); 7.41–7 81 (m, 4H).

EXAMPLE 36

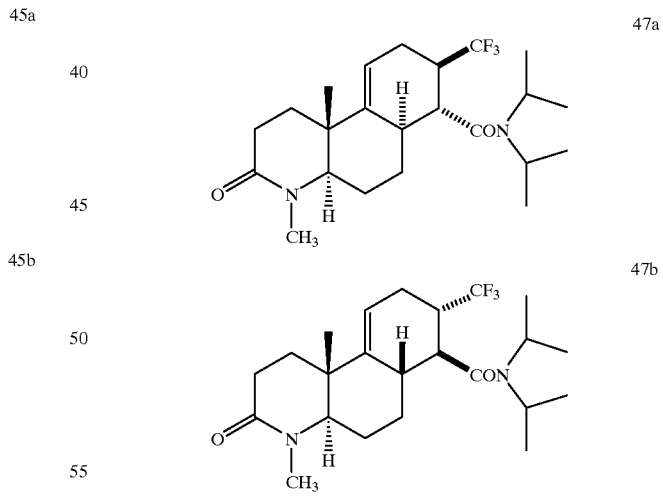

Using the procedure in Example 19, diisopropylamine was reacted with the acid chloride isomer mixture to give a mixture of the amides 47a and 47b in the ratio of 1:2, respectively. NMR (CDCl$_3$): 47a: δ 1.12 (s, 3H); 1.35–1.47 (m, 12H); 2.90 (s, 3H); 3.51 (dd, 1H); 5.58 (bs, 1H). 47b: δ 1.05 (s, 3H); 1.35–1.47 (m, 12H); 2,94 (s, 3H), 3.03 (dd, 1H); 5.52 (m, 1H).

EXAMPLE 37

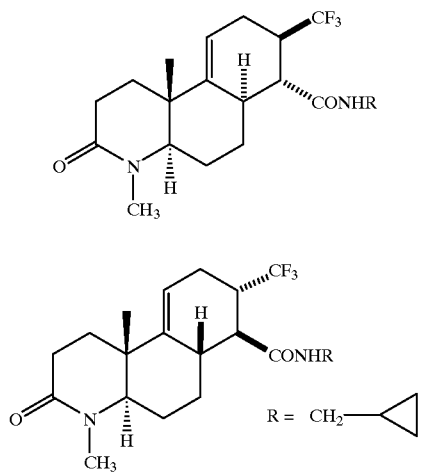

Using the procedure in Example 19, cyclopropylmethylamine was reacted with the acid chloride isomer mixture to give a mixture of the amides 48a and 48b in the ratio of 2:1, respectively. NMR (CDCl$_3$): 48a: δ 0.23 (m, 2H); 0.53 (m, 2H); 0.98 (m, 1H); 1.11 (s, 3H); 2.89 (s, 3H); 3.15 (m, 2H); 3.52 (dd, 1H); 5.58 (bs, 1H); 5.72 (m, 1H). 48b: δ 0.23 (m, 2H); 0.53 (m, 2H); 0.98 (1H); 1.05 (s, 3H); 2.94 (s, 3H); 3.03 (dd, 1H); 3.15 (m, 2H); 5.52 (m, 1H); 5.72 (m, 1H).

EXAMPLE 38

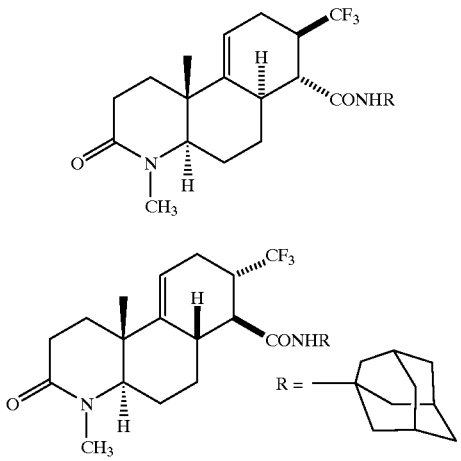

Using the procedure in Example 19, 1-adamantylamine was reacted with the acid chloride isomer mixture to give a mixture of the amides 49a and 49b in the ratio of 2:1, respectively. NMR (CDCl$_3$): 49a: δ 1.11 (s, 3H); 1.67 (bs, 6H); 2.02 (bs, 6H); 2.11 (bs, 3H); 2.90 (s, 3H); 3.51 (dd, 1H); 5.24 (s, 1H); 5.56 (bs, 1H). 49b: δ 1.04 (s, 3H); 1.67 (bs, 6H); 2.02 (bs, 6H); 2.11 (bs, 3H); 2.94 (s, 3H); 3.03 (dd, 1H); 5.27 (s, 1H); 5.49 (m, 1H).

EXAMPLE 39

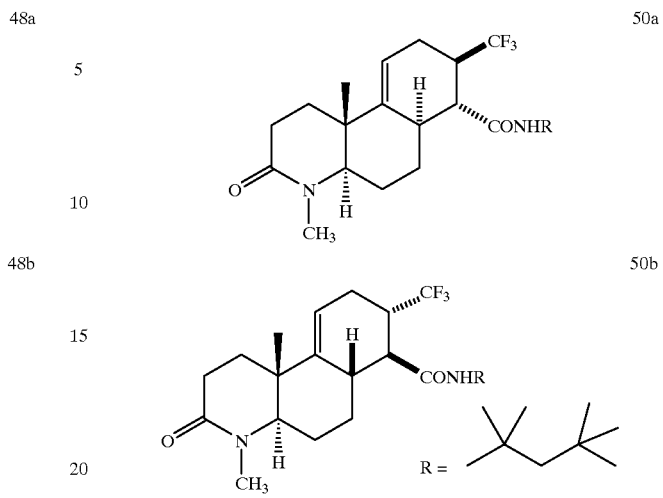

Using the procedure in Example 19, 1,1,3,3-tetramethylbutylamine was reacted with the acid chloride isomer mixture to give a mixture of the amides 50a and 50b in the ratio of 2:1, respectively. NMR (CDCl$_3$): 50a: δ 1.02 (s, 9H); 1.09 (s, 3H); 1.45 (s, 3H); 1.48 (s, 3H); 2.88 (s, 3H); 3.50 (dd, 1H); 5.51 (bs, 1H); 5.53 (bs, 1H). 50b: δ 1.02 (s, 12H); 1.45 (s, 3H); 1.48 (s, 3H); 2.92 (s, 3H); 5.47 (m, 1H); 5.53 (bs, 1H).

EXAMPLE 40

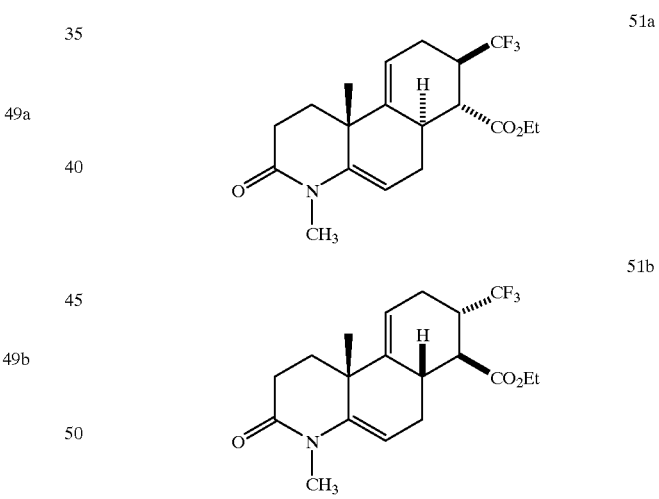

To a mixture of the triene 13 (Example 2) (2.67g, 13.1 mmoles) and ethyl 4,4,4-trifluorocrotonate (1.93 mL, 13.1 mmoles) cooled in an ice bath was added BCl$_3$ (1.0 M in CH$_2$Cl$_2$, 32.7 mL). The dark mixture was stirred at room temperature for 6 hrs, poured onto ice/1N HCl. The acid phase was washed with CH$_2$Cl$_2$ (2×). The combined CH$_2$Cl$_2$ phases were washed with water and saturated brine and dried (MgSO$_4$). The residue from evaporation in vacuo was flash chromatographed (silica gel, hexane-iPrOH, 9:1) to give 3.24 g of a 1:1 mixture of 51a and 51b. The isomers could be separated by preparative HPLC (silica gel, Waters Porasil™ 15–20 μm, 40×300 mm column, hexane-iPrOH, 95:5) to give the pure isomers. NMR (CDCl$_3$): 51a (less polar): δ 1.28 (s, 3H); 1.29 (t, 3H); 3.12 (s, 3H); 4.22 (q, 2H); 5.21 (dd, 1H); 5.68 (bs, 1H). 61b (more polar): δ 1.24 (s, 3H); 1.29 (t, 3H); 3.13 (s, 3H); 4.22 (q, 2H); 5.05 (dd, 1H); 5.63 (m, 1H).

Starting with (−)-13 (Example 2), the above procedure afforded (−)-51b, [α]$_{D=-131.5}$° (CHCl$_3$, c=1.52).

Starting with (+)-13 (Example 2), the above procedure afforded (+)-51b, [α]$_D$=+156° (CHCl$_3$, c=1.58).

EXAMPLE 41

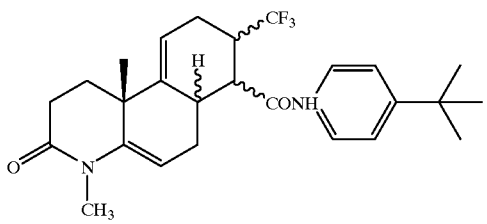

52a

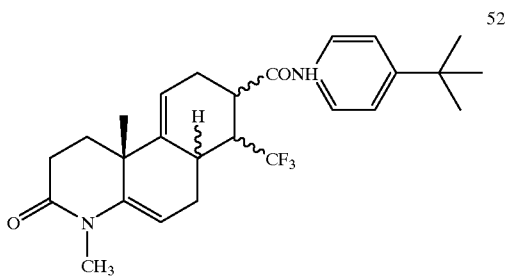

52b

Using the method of Example 14, step C, substituting the triene 13 for the diene 6, a mixture of 3 isomers (52a and 52b) A, B, and C in the ratio of 1.6:2:1, respectively, was obtained. NMR (CDCl$_3$): isomer A: δ 1.22 (s, 3H); 1.33 (s, 9H); 3.12 (s, 3H); 5.20 (d, 1H); 5.69 (s, 1H); 7.28 (s, 1H); 7.37–7.49 (m, 4H). isomer B: δ 1.27 (s, 3H); 1.33 (s, 9H); 3.12 (s, 3H); 5.04 (d, 1H); 5.68 (s, 1H); 7.28 (s, 1H); 7.37–7.49 (m, 4H). isomer C: δ 1.23 (s, 3H); 1.32 (s, 9H); 3.12 (s, 3H); 5.06 (d, 1H); 5.53 (s, 1H); 7.28 (s, 1H); 7.37–7.49 (m, 4H).

EXAMPLE 42

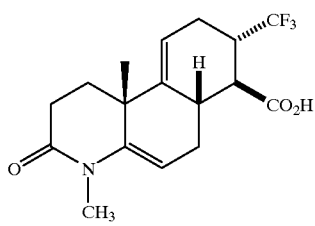

53

A mixture of 51b (0.99 g, 2.67 mmoles), 5N NaOH (12 mL), and MeOH (46 mL) was allowed to stand at room temperature in a N$_2$ atmosphere for 18 hrs. After heating at 50° for 1 hr, most of the MeOH was evaporated in vacuo, water (30 mL) was added, and the mixture acidified to pH 2 with conc HCl. The suspension was warmed with stirring for a few minutes, and cooled in an ice bath for 1 hr. The solid was filtered, washed with cold water (3×), and dried to give 53 as a colorless powder. NMR (CDCl$_3$): 1.25 (s, 3H); 3.15 (s, 3H); 5.08 (dd, 1H); 5.65 (m, 1H).

Starting with (−)-51b, the above procedure gave (−)-53, [α]$_D$=−160° (CHCl$_3$, c=1.05).

Starting with (+)-51b, the above procedure gave (+)-53, [α]$_D$=+164° (CHCl$_3$, c=1.07).

EXAMPLE 43

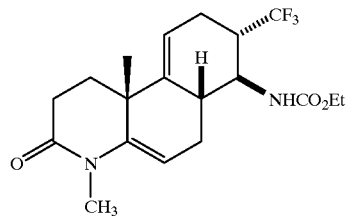

54

A solution of the diene acid 53 (Example 42, 32 mg, 0.093 mmole), diphenylphosphoryl azide (20 mL, 0.093 mmole) and triethylamine (13 μL, 0.093 mmole) in ethanol (1.0 mL) was refluxed for 7 hours. The cooled reaction mix was concentrated in vacuo . The residue was dissolved in CH$_2$Cl$_2$, washed with 1N HCl, water, 10% NaHCO$_3$, and dried (MgSO$_4$). Evaporation in vacuo gave 54. NMR (CDCl$_3$): δ 1.23 (s, 3H); 1.27 (t, 3H); 3.15 (s, 3H); 3.66 (q, 1H); 4.15 (q, 2H); 4.74 (d, 1H); 5.10 (s, 1H); 5.61 (s, 1H).

EXAMPLE 44

55

The diene acid (−)-53 (Example 42, 64 mg, 0.186 mmoles) was suspended in toluene (2.5 mL). About 0.7 mL was distilled; the suspension cooled in an ice bath and pyridine (38 μl, 0.47 mmoles), 1 drop of DMF, and SOCl$_2$ (16 μl, 0.219 mmoles) were added. The suspension was stirred at room temperature for 1.5 hrs and warmed to 90° for 5 min. 3-t-Butylaniline (44 μl, 0.279 mmoles) and DMAP (0.5 mg) was added, and the mixture was heated at 90° for 1 hr. The reaction was diluted with CH$_2$Cl$_2$ (20 mL) and washed with 1N HCl, water, 1N NaOH and water and dried (MgSO$_4$). The residue from evaporation in vacuo was purified by preparative TLC (silica gel, hexane-EtOAc, 1:1) to afford (−)-55 [α]$_D$=−123° (CHCl$_3$, c=0.80). NMR (CDCl$_3$): δ 1.24 (s, 3H); 1.30 (s, 9H); 3.10 (s, 3H); 5.02 (m, 1H); 5.64 (d, 1H); 7.18 (dd, 1H); 7.23–7.31 (m, 2H); 7.36 (dd, 1H); 7.50 (m, 1H).

Starting with (+)-53, the above procedure gave (+)-55, [α]$_D$=+116° (CHCl$_3$, c=0.80).

EXAMPLE 45

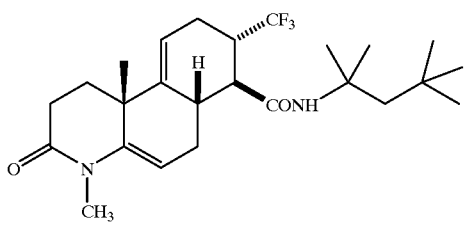

Using the procedure in Example 44, (−)-53 and 1,1,3,3-tetramethylbutylamine gave (−)-56, $[\alpha]_D=-187°$ (CHCl$_3$, c=0.80). NMR (CDCl$_3$): δ 1.03 (s, 9H); 1.22 (s, 3H); 1.44 (s, 3H); 1.47 (s, 3H); 3.10 (s, 3H); 5.02 (m, 1H); 5.53 (bs, 1H); 5.58 (d, 1H).

EXAMPLE 46

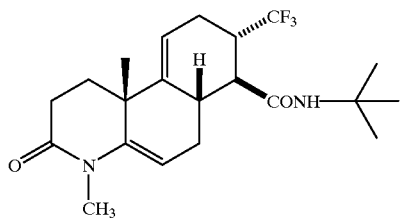

Using the procedure in Example 44, (+)-53 and t-butylamine afforded (+)-57, $[\alpha]_D=+116°$ (CHCl$_3$, c=0.80). NMR (CDCl$_3$): δ 1.22 (s, 3H); 1.36 (s, 9H); 3.10 (s, 3H); 5.03 (m, 1H); 5.43 (bs, 1H); 5.59 (m, 1H).

EXAMPLE 47

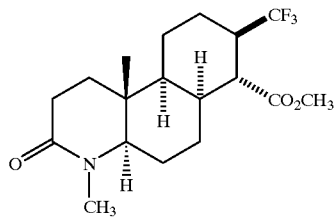

The acid 26c (Example 15) (122 mg) in HOAc (3.5 mL) was hydrogenated at atmospheric pressure with PtO$_2$ (13 mg). After 5 days at room temperature the reaction was not complete. Another 13 mg of catalyst was added, and the hydrogenation continued at 60° for 6 hrs. The catalyst was filtered and washed with HOAc (2×). The residue after removal of the HOAc in vacuo was dissolved in toluene (3 mL) and MeOH (0.75 mL) and treated with Me$_3$SiCH=N$_2$ (2.0 M in hexane) until N$_2$ evolution stopped and a yellow color persisted. The residue after removal of the solvent in vacuo was purified by flash chromatography (silica gel, CH$_2$Cl$_2$-acetone, 5:1) to give pure 58. NMR (CDCl$_3$): δ 1.03 (s, 3H); 2.94 (s, 3H); 3.08 (dd, 1H); 3.75 (s, 3H).

EXAMPLE 48

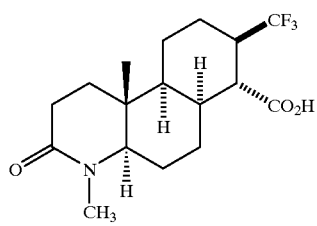

The ester 58 (Example 47) (40 mg) was heated under reflux with 5N NaOH (0.5 mL) and EtOH (2.0 mL) for 4 hrs. Most of the EtOH was removed in vacuo; and the residue acidified with conc HCl. The suspension was aged for 1 hr, filtered, and the solid washed with water (2×) and dried to give 59. NMR (CDCl$_3$/trace CD$_3$OD): δ 1.00 (s, 3H); 2.95 (s, 3H); 3.11 (m, 1H).

EXAMPLE 49

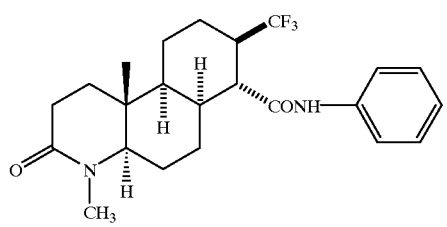

Using the procedure in Example 18, the acid 59 (61 mg) was converted into the corresponding thiopyridyl ester (38 mg). NMR (CDCl$_3$): δ 1.03 (s, 3H); 2.92 (s, 3H); 3.05 (m, 1H); 7.32 (m, 1H); 7.58 (d, 1H); 7.76 (m, 1H); 8.62 (d, 1H).

To a solution of the thiopyridyl ester (38 mg, 0.086 mmoles) and aniline (32 μl, 0.347 mmoles) in THF (1 mL) was added AgOTf (27 mg, 0.105 mmoles). The yellow suspension was heated under reflux for 4 hrs. The solid was filtered and washed with CHCl$_3$ (3×). The filtrate was washed with water, 5% NH$_4$OH, 1 N HCl, and saturated brine and dried (MgSO$_4$). The residue after evaporation in vacuo was purified by preparative TLC (silica gel, CH$_2$Cl$_2$-acetone, 4:1) and preparative HPLC (silica gel, hexane-iPrOH, 80:20) to afford pure anilide 60 (18 mg). NMR (CDCl$_3$): δ 1.03 (s, 3H); 2.92 (s, 3H); 3.10 (dd, 1H); 7.12 (t, 1H); 7.31 (t, 2H); 7.53 (d, 2H); 8.24 (s, 1H).

EXAMPLE 50

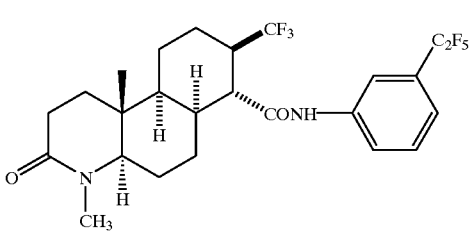

The anilide 31a (Example 20) (35 mg) in HOAc (1 mL) was hydrogenated at atmospheric pressure with PtO$_2$ (4 mg).

After 18 hrs the catalyst was filtered and washed with HOAc. Most of the HOAc was removed in vacuo. The residue was dissolved in $CH_2Cl_2$, washed with 10% $NaHCO_3$, water, and saturated brine and dried ($MgSO_4$). The solvent was removed in vacuo to pure 61. NMR ($CDCl_3$): δ 1.02 (s, 3H); 2.94 (s, 3H); 3.15 (dd, 1H); 7.31 (d, 1H); 7.43 (t, 1H); 7.67 (s, 1H); 7.96 (d, 1H); 9.32 (bs, 1H).

EXAMPLE 51

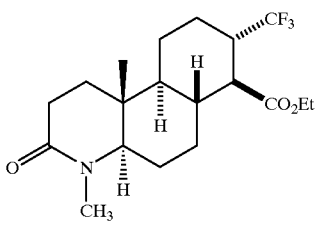

62

The diene ester 51b (Example 40) (950 mg) in HOAc (15 mL) was hydrogenated at atmospheric pressure with $PtO_2$ (270 mg). After 18 hrs at room temperature, the reaction was not complete. Another 280 mg of $PtO_2$ was added and the hydrogenated continued at 50° for 5 hrs. The catalyst was filtered and washed with HOAc. Most of the HOAc was removed in vacuo. The residue was dissolved in $CH_2Cl_2$ and washed with 10% $NaHCO_3$ and dried ($MgSO_4$). The residue after removal of the solvent in vacuo was purified by flash chromatography (silica gel, hexane-iPrOH, 85:15) to give pure 62. NMR ($CDCl_3$): δ 0.88 (s, 3H); 1.39 (t, 3H); 2.94 (s, 3H); 3.06 (dd, 1H); 4.19 (q, 2H).

Starting with (−)-51b (Example 40), the above procedure afforded (−)-62, $[\alpha]_D$=−7.25° ($CHCl_3$, c=0.81).

EXAMPLE 52

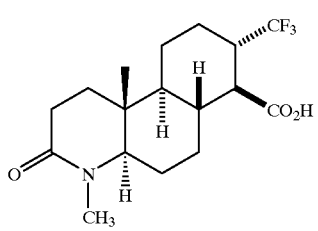

63

A mixture of the ester 62 (Example 51) (141 mg, 0.376 mmoles), 9 M KOH (250 μl, 2.25 mmoles) and ethylene glycol (1.5 mL) was heated at 120° for 22 hrs. The reaction was diluted with water and acidified with conc HCl. The suspension was aged for 1 hr and filtered. The solid was washed with water and dried to give 63. NMR ($CDCl_3$): δ 0.88 (s, 3H); 2.94 (s, 3H); 3.06 (dd, 1H).

EXAMPLE 53

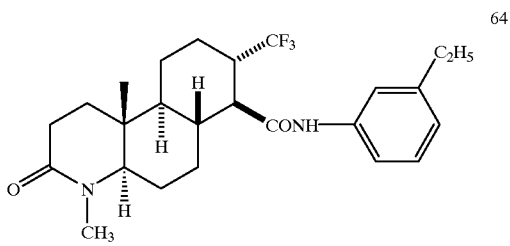

64

The saturated acid 63 (105 mg) was converted into the acid chloride and reacted with 3-ethylaniline using the procedures in Example 19. Both reactions were hampered by the insolubility of the acid 63 and its acid chloride. DMF catalysis was used for the acid chloride preparation, and the reaction of it with the aniline was carried out at 500 for 18 hrs. Purification by preparative TLC (silica gel, hexane-iPrOH, 4:1) gave 64. NMR ($CDCl_3$): δ 0.90 (s, 3H); 1.26 (t, 3H); 2.66 (q, 2H); 2.93 (s, 3H); 3.06 (dd, 1H); 7.02–7.39 (m, 4H).

EXAMPLE 54

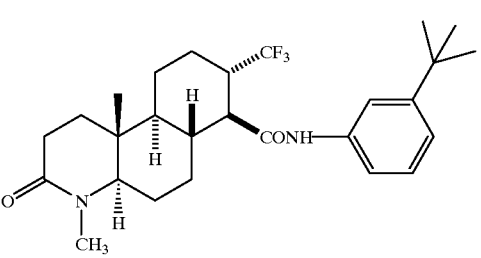

65

Using the procedure in Example 53, 63 (53 mg) and 3-t-butylaniline were reacted to afford 65. NMR ($CDCl_3$): δ 0.90 (s, 3H); 1.34 (s, 9H); 2.93 (s, 3H); 3.06 (dd, 1H); 7.19–7.48 (m, 5H).

EXAMPLE 55

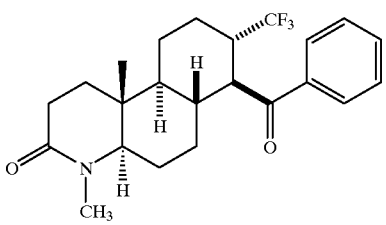

66

To a solution of 63 (Example 52) (73 mg, 0.209 mmole), pyridine (53 μL, 0.626 mmole) and DMF (10 μL) in $CH_2Cl_2$ (2 mL) at 0° in a $N_2$ atmosphere, was added, dropwise, $SOCl_2$ (18 μL, 0.245 mmole). After stirring at room temperature for 3 hours the reaction mixture was cooled and washed with a cold 1N HCl, brine, dried ($MgSO_4$), and concentrated in vacuo to give the crude acid chloride. $CH_2Cl_2$ (1 mL) was added, and the solution added dropwise to a suspension of $AlCl_3$ (96 mg, 0.72 mmole) in benzene (64 μL, 0.72 mmole) and $CH_2Cl_2$ (1 mL) at 0° in a $N_2$ atmosphere. After stirring at room temperature for 2 hours, the solution was treated slowly with 2N HCl. The resulting mixture was diluted with CH₂Cl₂ and washed with water, 10% NaHCO₃, saturated brine, dried (MgSO₄), and concentrated in vacuo to give a yellow solid (140 mg). The solid was purified by flash chromatography (silica gel, hexane-iPrOH, 88:12) and HPLC (silica gel, hexane-iPrOH, 85:15) to give the ketone 66. NMR (CDCl₃): δ 0.90 (s, 3H); 2.87 (s, 3H); 3.05 (dd, 1H); 3.34 (t, 1H); 7.51 (t, 2H); 7.61 (t, 1H); 7.96 (d, 2H).

EXAMPLE 56

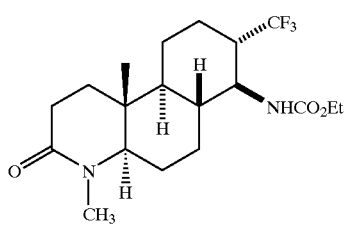

Using the procedure in Example 51, the diene urethane 54 (13 mg) (Example 43) was hydrogenated at 50° for 18 hrs to give 67. NMR (CDCl₃): δ 0.86 (s, 3H); 1.25 (t, 3H); 2.94 (s, 3H); 3.06 (dd, 1H); 4.13 (q, 2H); 4.54 (s, 1H).

EXAMPLE 57

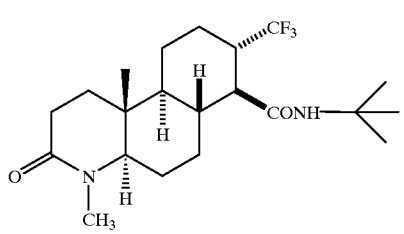

Using the procedure in Example 51, the amide 30b (Example 19) (30 mg) was hydrogenated at 50° for 18 hrs to give 68. NMR (CDCl₃): 0.85 (s, 3H); 1.34 (s, 9H); 2.91 (s, 3H); 3.01 (dd, 1H); 5.28 (bs, 1H). Racemic 68 could be resolved into its enantiomers by preparative chiral HPLC on a ChiralPak AD column with hexane-iPrOH (85:15) to give samples of (+)-68 (faster moving), [α]$_D$=+10° (CHCl₃, c=1.1) and (−)-68 (slower moving), [α]$_D$=−10° (CHCl₃, c=1.2).

EXAMPLE 58

Using the procedure in Example 51, (+)-57 (Example 46) (56 mg) was hydrogenated at 50° for 18 hrs, and the product purified by recrystallization from Et₂O-CH₂Cl₂ to give pure (+)-68, [a]$_D$=+11.3° (CHCl₃, c=1.05). The NMR spectrum is identical with 68 prepared in Example 57.

EXAMPLE 59

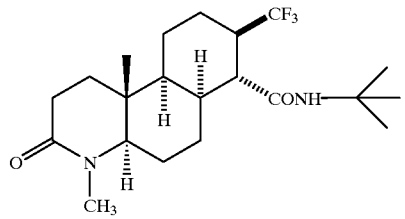

Using the procedures in Examples 51 and 57, the amide 30a was hydrogenated to give 69, NMR (CDCl₃): 1.00 (s, 3H); 1.35 (s, 9H); 2.94 (s, 3H); 3.07 (dd, 1H); 5.44 (bs, 1H).

EXAMPLE 60

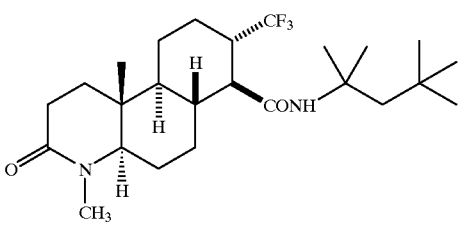

Using the procedures in Example 51 and 57, the amide (−)-56 (Example 45) was hydrogenated to give (−)-70, [α]$_D$=−8.3° (CHCl₃, c=0.875). NMR (CDCl₃): δ 0.83 (s, 3H);1.02 (s, 9H); 1.41 (s, 3H); 1.44 (s, 3H); 2.90 (s, 3H); 3.00 (dd, 1H); 5.42 (bs, 1H).

EXAMPLE 61

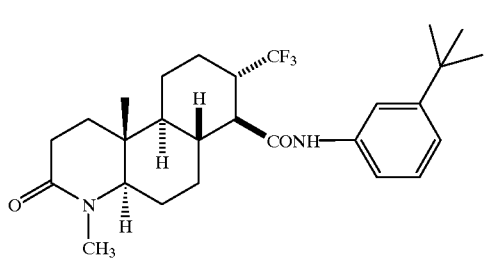

Using the procedures in Example 51 and 57, the anilide (−)-55 (Example 44) was hydrogenated at room temperature for two days. Purification by recrystallization from Et₂O-CH₂Cl₂ gave pure (−)-65, [α]$_D$=−20.8° (CHCl₃, c=1.05). NMR (CDCl₃): δ 0.86(s, 3H); 1.31 (s, 9H); 2.89 (s, 3H); 3.03 (dd, 1H); 5.64 (d, 1H); 7.17 (dd, 1H); 7.28 (dd, 2H); 7.36 (dd, 2H); 7.45 (m, 1H).

Using the above procedure, (+)-55 (Example 44) gave after recrystallization from EtOAc pure (+)-65, [α]$_D$=+21.1° (CHCl₃, c=1.07). The NMR spectrum is identical with (−)-65.

EXAMPLE 62

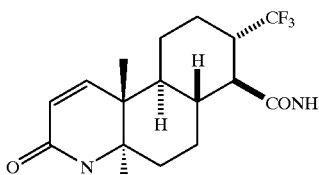

Step A: Preparation of 72

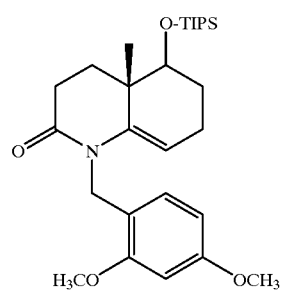

A solution of 9 (Example 2, Step B) (8.29 g, 23.2 mmole), NaOAc (2.38 g, 29.0 mmole) and 2,4-dimethoxybenzylamine.HCl (6.09 g, 29.0 mmole) in xylene (330 mL) was refluxed for 5.5 hrs employing a Dean-Stark trap. The mixture was cooled, diluted with water and extracted with EtOAc (2x). The combined extracts were washed with water, brine, dried (MgSO$_4$) and concentrated in vacuo to give the crude product. Chromatography (silica gel, hexane:EtOAc, 4:1) afforded 72 as a solid. NMR (CDCl$_3$): δ 1.09 (s, 18H); 1.13 (s, 3H); 3.79 (s, 3H); 3.83 (s, 3H); 4.57 (d, 1H); 4.86 (s, 1H); 5.09 (d, 1H); 6.42 (m, 2H); 6.81 (d, 1H).

Step B: Preparation of 73

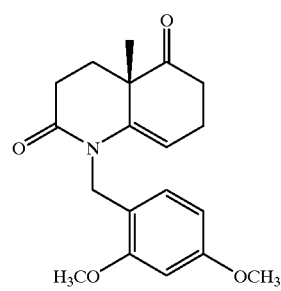

To a solution of 1M n-Bu$_4$NF in THF (100 mL) was added 72 (13.1g, 26.9 mmole), and the mixture refluxed for 10 minutes, cooled and concentrated in vacuo. The residue was partitioned with EtOAc and water, and the organic phase washed with water, brine, dried (MgSO$_4$) and concentrated in vacuo to give the crude alcohol which was used without purification in the next reaction.

To a mixture of the alcohol (14.6 g, 26.9 mmole), N-methylmorpholine-N-oxide (4.89 g, 40.3 mmole), and 4Å powdered molecular sieves (15 g) in CH$_2$Cl$_2$ (125 mL) was added tetrapropylammonium perruthenate(VII) (496 mg, 1.35 mmole). The mixture was stirred rapidly for 30 min and chromatographed (silica gel, hexane-EtOAc, 3:2 then EtOAc:hexane (7:3) to afford 73 as a gum. NMR (CDCl$_3$):

δ 1.31 (s, 3H); 3.80 (s, 3H); 3.85 (s, 3H); 4.80 (d, 1H); 5.01 (d, 1H); 5.23 (t, 1H); 6.42 (d, 1H); 6.46 (s, 1H); 6.84 (d, 1H).

Step C: Preparation of 74

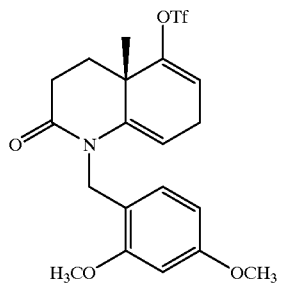

To a solution of 73 (8.0 g, 24.29 mmole) in THF (250 mL) at 0° in a N$_2$ atmosphere was added KN(SiMe$_3$)$_2$ (0.5M in toluene, 53.4 mL, 26.72 mmole). After stirring at 0° for 45 min, PhN(Tf)$_2$ (10.41 g, 29.15 mmole) was added and the reaction was stirred at room temperature for 1.5 hours. The mixture was treated with a small amount of saturated NH$_4$Cl solution, water and extracted with EtOAc (2x). The combined extracts were washed with water, brine and (MgSO$_4$). Evaporation in vacuo and chromatography (silica gel, hexane-EtOAc, 4:1, then hexane-EtOAc, 3:2) afforded 74 as a gum. NMR (CDCl$_3$): δ 1.36 (s, 3H); 3.80 (s, 3H); 3.84 (s, 3H); 4.75 (d, 1H); 5.02 (d, 1H); 5.07 (t, 1H); 5.79 (t, 1H); 6.43 (dd, 1H); 6.46 (d, 1H); 6.88 (d, 1H).

Step D: Preparation of 75

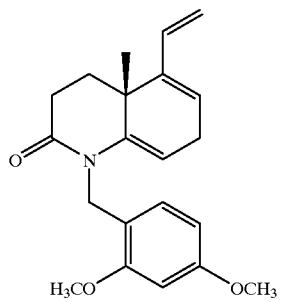

A solution of 74 (8.79 g, 19.05 mmole), tributyl(vinyl)tin (6.0 mL, 20.0 mmole), LiCl (2.42 g, 57.15 mmole) and (Ph$_3$P)$_4$Pd (440 mg, 0.381 mmole) in THF (150 mL) was refluxed in a N$_2$ atmosphere for 18 hours. The cooled mixture was concentrated in vacuo, and the residue dissolved in EtOAc, washed with 10% NH$_4$OH, water (2x), brine and dried (MgSO$_4$). Evaporation in vacuo and chromatography (silica gel, hexane-EtOAc, 3:2) afforded 75 as an off-white solid. NMR (CDCl$_3$): δ 1.28 (3H); 3.79 (s, 3H); 3.84 (s, 3H); 4.67 (d, 1H); 5.09 (m, 4H); 5.38 (d, 1H); 5.82 (s, 1H); 6.35 (m, 1H); 6.42 (d, 1H); 6.45 (s, 1H); 6.88 (d, 1H).

77

Step E: Preparation of 76a and 76b

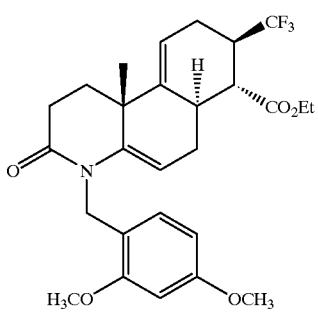

76a

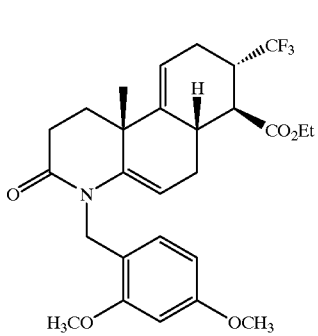

76b

To a mixture of 75 (5 g, 14.7 mmole) and ethyl 4,4,4-trifluorocrotonate (2.21 mL, 15.2 mmole) at 5° in a $N_2$ atmosphere, was added dropwise $BCl_3$ (1M in $CH_2Cl_2$, 36.8 mL). The mixture was stirred at room temperature for 4.5 hours, cooled to 10° and 1N HCl (40 mL) added dropwise. The mixture was extracted with $CH_2Cl_2$ and the organic phase washed with water and brine and dried ($MgSO_4$). Evaporation in vacuo and chromatography (silica gel, hexane-EtOAc, 7:3, then 3:2, and finally 1:1) provided the title compound as a 1:1 mixture of isomers (76a, 76b). The isomers were separated by HPLC (silica gel, hexane-EtOAc, 65:35). Isomer 76a (less polar): NMR ($CDCl_3$): δ 1.28 (t, 3H); 1.30 (s, 3H); 3.80 (s, 3H); 3.83 (s, 3H); 5.12 (q, 2H); 4.71 (d, 1H); 4.99 (d, 1H); 5.12 (d, 1H); 5.7 (s, 1H); 6.42 (d, 1H); 6.45 (s, 1H); 6.83 (d, 1H). Isomer 76b (more polar): δ 1.27 (s, 3H); 1.28 (t, 3H); 3.79 (s, 3H); 3.82 (s, 3H); 4.20 (q, 2H); 4.60 (d, 1H); 4.98 (dd, 1H); 5.09 (d, 1H); 5.67 (d, 1H); 6.40 (d, 1H); 6.42 (s, 1H); 6.81 (d, 1H).

Step F: Preparation of 77

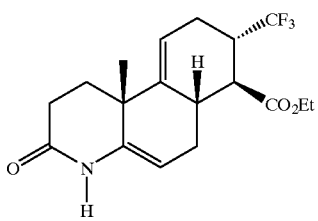

77

A solution of 76b (953 mg, 1.88 mmole) and TFA (3.5 mL) in $CH_2Cl_2$ (3.5 mL) was stirred at room temperature for 24 hours. The mixture was concentrated (cold) in vacuo, and the residue dissolved in $CH_2Cl_2$ and brought to pH 7 with 10% potassium carbonate. The organic phase was washed with water and brine and dried ($MgSO_4$). Evaporation in vacuo and preparative reverse phase HPLC (C-8 column, MeOH-water gradient, 80:20 to 100% methanol) afforded 77. NMR ($CDCl_3$): δ 1.30 (t, 3H); 1.31 (s, 3H); 4.24 (q, 2H); 4.85 (dd, 1H); 5.64 (d, 1H); 7.39 (s, 1H).

Step G: Preparation of 78

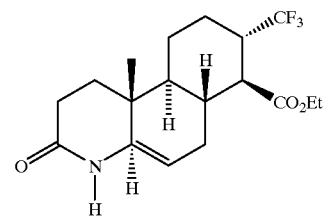

78

A solution of 77 (75 mg, 0.21 mmole) and $PtO_2$ (70 mg) in HOAc (1.5 mL) was stirred under a balloon of hydrogen for 5.5 hrs at room temperature. The solvent was pipetted away from the catalyst and combined with several HOAc washings of the residue. The combined washings were dissolved in $CH_2Cl_2$, washed with water, 10% $NaHCO_3$, and brine and dried ($MgSO_4$). Evaporation in vacuo to afforded 78. NMR ($CDCl_3$): δ 0.89 (s, 3H); 1.28 (t, 3H); 3.09 (dd, 1H); 4.18 (q, 2H); 6.36 (s, 1H). Step H: Preparation of 71 A solution of 78 (96 mg, 0.266 mmole), DDQ (74 mg, 0.319 mmole), bis(trimethylsilyl)trifluoroacetamide (285 μL, 1.064 mmole) and trifluoromethanesulfonic acid (2 μL, 0.02 mmole) in toluene (3 mL) was stirred at room temperature for 24 hours. Methyl acetoacetate (3 μL, 0.206 mmole) was added; the mixture stirred for 1.5 hours and then refluxed for 24 hours. The cooled solution was partitioned with $CH_2Cl_2$ and water (9 mL) containing $Na_2CO_3$ (135 mg) and $NaHSO_3$ (70 mg). The organic phase was washed with 5% $NaHCO_3$, water, and brine and dried ($MgSO_4$). Evaporation in vacuo and chromatography (silica gel, acetone-$CH_2Cl_2$ (15:85) afforded 71. NMR ($CDCl_3$): δ 0.96 (s, 3H); 1.29 (t, 3H); 3.36 (t, 1H); 4.20 (q, 2H); 5.38 (s, 1H); 5.88 (d, 1H); 6.75 (d, 1H).

EXAMPLE 63

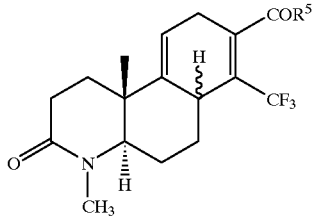

79a–87a

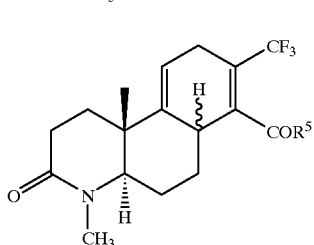

79b–87b

79 -continued

79c–87c

[Structure: tricyclic steroid-like core with CF₃ group, COR⁵ substituent, N-CH₃ lactam]

| | R⁵ |
|---|---|
| 79 | OH |
| 80 | NH–C₆H₄–C(CH₃)₃ (meta) |
| 81 | NHC(CH₃)₃ |
| 82 | NHC(CH₃)₂CH₂C(CH₃)₃ |
| 83 | NH–C₆H₅ |
| 84 | NH–C₆H₄–CF₂CF₃ (meta) |
| 85 | NH–C₆H₄–CF₂CF₂CF₃ (meta) |
| 86 | NH–C₆H₄–CF₂CCl₃ (meta) |
| 87 | NH–C₆H₄–C₂H₅ (meta) |

Using the procedure in Example 15, the ester isomers 21a–c are saponified to form the carboxylic acids 79a–c. Using the procedure in Example 19, the acid chlorides formed from 79a–c are reacted with the appropriate amine to give the amides 80a,b,c–87a,b,c.

EXAMPLE 64

88–96

[Structure: tricyclic steroid-like core with CF₃ group, COR⁵ substituent, N-H lactam with double bond]

| | R⁵ |
|---|---|
| 88 | OH |
| 89 | NH–C₆H₄–C(CH₃)₃ (meta) |
| 90 | NHC(CH₃)₃ |
| 91 | NHC(CH₃)₂CH₂C(CH₃)₃ |
| 92 | NH–C₆H₅ |
| 93 | NH–C₆H₄–CF₂CF₃ (meta) |
| 94 | NH–C₆H₄–CF₂CF₂CF₃ (meta) |
| 95 | NH–C₆H₄–CF₂CCl₃ (meta) |
| 96 | NH–C₆H₄–C₂H₅ (meta) |

Using the procedure in Example 15 except that t-butanol is used in place of methanol, the ester 71 are saponified to form the carboxylic acid 88. Using the procedure in Example 19, the acid chloride formed from 88 are reacted with the appropriate amine to give the amides 89–96.

EXAMPLE 65

ORAL COMPOSITION

As a specific embodiment of an oral composition of a compound of this invention, 5 mg of a compound of structural formula I is formulated with sufficient finely divided lactose to provide a total amount of 580 to 590 mg to fill a size 0 hard gelatin capsule.

Biological Assays

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25 M sucrose using a Potter-Elvehjem homogenizer. A crude nuclear pellet was prepared by centrifugation of the homogenate at 1,500× g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase Assay:
Inhibition studies

For $IC_{50}$ determinations, the inhibitors were dissolved in ethanol and serially diluted to the appropriate concentration. Human scalp or recombinantly-expressed enzyme can be used as the source of type 1 5α-reductase. Human prostate or recombinantly-expressed enzyme can be the source of type 2 5α-reductase. Typically, the type 1 enzyme was preincubated with inhibitor (0.1–1,000 nM) in 40 mM sodium phosphate, pH 7.0, 500 µM NADPH, 1 mM DTT and 1 mg/mL BSA for 18 h at 4° C. The reaction was initiated by the addition of [7-3H]T (NEN, 20 Ci/mmol) and NADPH to final concentrations of 5 µM and 500 µM, respectively. The reaction was incubated at 37° C. for 90 min. Similarly, type 2 5α-reductase was preincubated with inhibitor (1–10,000 nM) in 40 mM sodium citrate, pH 5.5, 500 µM NADPH, 1 mM DTT and 1 mg/mL BSA for 18 h at 4° C. The reaction was initiated by the addition of [7-3H]T (NEN, 20 Ci/mmol) and NADPH to a final concentration of 0.3 µM and 500 µM, respectively. The conversion of T to DHT was monitored using a radioflow detector following separation by reverse phase HPLC (Whatman RACII C18 column, 1 mL/min 0.1% TFA in water:methanol (42:58); retention times T, 6.3 min, DHT, 9.7 min).

A compound referred to herein as a 5α-reductase 1 inhibitor is a compound that shows inhibition of the 5α-reductase 1 isozyme in the above-described assay, having an $IC_{50}$ value of about or under 100 nM.

Compounds of the present invention with the above 5α-reductase 1 isozyme inhibitory properties possess the natural steroidal trans-anti-trans relative configuration at the A,B and B,C ring junctures as depicted in general structural formula (I). Moreover, compounds of the present invention with the above 5α-reductase 1 isozyme possess the nonsteroidal trans-anti-trans absolute configuration at the A,B and B,C ring junctures as depicted in general structural formula (II).

A compound referred to herein as a 5α-reductase 2 inhibitor is a compound that shows inhibition of the 5α-reductase 2 isozyme in the above-described assay, having an $IC_{50}$ value of about or under 100 nM.

Human Dermal Papilla Cell Assay

The dermal papilla is a small group of cells at the base of each hair follicle, and it is presently thought that these cells are stem cells that form the basis for hair growth. These cells have been shown to have 5α reductase activity, and it is therefore possible to test inhibitors of 5α. reductase in these cell culture systems.

Isolated and cultured dermal papilla cells are prepared according to the methods of Messenger, A. G., "The Culture of Dermal Papilla Cells From Human Hair Follicles," *Br. J. Dermatol.*, 110:685–689 (1984) and Itami, S. et al., "5α-reductase Activity In Cultured Human Dermal Papilla Cells From Beard Compared With Reticular Dermal Fibroblasts," *J. Invest. Dermatol.*, 94:150–152 (1990). Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min. at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α.-reductase, the cell homogenate is centrifuged at 800× g for 10 min. to yield a crude nuclear pellet. The resultant supernatant is centrifuged at 10,000× g for 15 min. to produce a crude mitochondrial pellet. The supernatant is centrifuged at 100,000× g for 60 min. to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 mL of the cell homogenate, in a final volume of 100 mL. Each tube contains 50–100 mg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et al., "Protein Measurement With The Folin Phenol Reagent," *J. Biol. Chem.*, 193:265–275 (1951).

After incubation, the reaction is stopped by adding 4 times volume of chloroform-methanol (2/1:V/V) containing 110 mg each of carrier steroids. The extracted steroids are analyzed by thin-layer chromatography as previously described by Gomez, et al., "In Vitro Metabolism Of Testosterone-4-$^{14}$C and D-androstene-3,17-dione-4-$^{14}$C In Human Skin.," *Biochem.*, 7:24–32 (1968), and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

The following describes an example of methodology that can be used for detection of hair growth.

Macrophotography and Global Photography Procedure for Detection OF Hair Growth

A. Macrouhotograuhic Procedure

| | |
|---|---|
| Location: | ID card |
| | Haircount target area |
| Equipment: | Film: Kodak-T-max 24 exposure each of same emulsion lot number |
| Camera: | Nikon N-6000 |

-continued

| | |
|---|---|
| Lens: | Nikkor 60 mm f2.8 |
| Flashes: | Nikon SB-21B Macroflash |
| Device: | registration device |

Photographic Procedure:

In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.
2. Magnification: Each lens supplied has a fixed reproduction ratio of 1:1.2.
   Aperture: Every photograph is taken at f/22.
   Film: T-Max 100 (24 exposure) is used.
3. Patient's haircount target area. Three exposures (−2/3, 0, and +2/3 f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and DeLong, E., *J. American Academy of Dermatology*, Vol. 23, p.470 (1990).

B. Global Photographic Procedure

| | |
|---|---|
| Locations: | Color card/patient Id |
| | Global photograph |
| Equipment: | Film: Kodachrome KR-64 24 exposure each of same emulsion lot number |
| Camera: | Nikon N-6000 |
| Lens: | Nikkor 60 mm f2.8 |
| Flashes: | Nikon SB-23 |

Photographic Procedure In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.
2. Magnification: Each lens supplied has a fixed reproduction ratio of 1:6.
   Aperture: Every photograph will be taken at f/11.
   Film: Kodachrome (24 exposure) is used.
3. Patient's global photographs. Three exposures at zero compensation.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula (I) having the natural steroidal trans-anti-trans relative configuration at the A,B and B,C ring junctures:

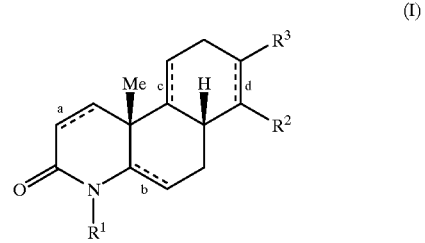

or a pharmaceutically acceptable salt, ester or stereoisomer thereof, wherein:

the bonds designated with dotted lines "a", "b", "c" and "d" may be single bonds or double bonds, provided that when "a" is a double bond, the dotted lines "b", "c" and "d" must represent single bonds; and further provided that when "b" is a double bond, "c" or both "c" and "d" must represent double bonds;

$R^1$ is selected from hydrogen, $C_{1-5}$ alkyl and $CH_2R^5$;

$R^2$ is selected from:
(1) hydrogen,
(2) $CO_2R^4$,
(3) $CONR^4R^5$,
(4)

(5) $COR^5$,
(6) $S(O)_nR^5$,
(7) $NHCO_2R^4$,
(8) $NHCOR^4$,
(9) $NHCOR^5$,
(10) CN,
(11) $COSR^5$,
(12) $C_{15}$ alkyl, and
(13) $C_xX_y$;

$R^3$ is selected from:
(1) hydrogen,
(2) $C_{1-5}$ alkyl,
(3) $CO_2R^4$,
(4) $CONR^4R^5$,
(5) $COR^5$,
(6) $S(O)_nR^5$,
(7) CN, and
(8) $C_xX_y$;

$R^4$ is selected from: hydrogen, and $C_{1-10}$ straight or branched-chain alkyl;

$R^5$ is selected from:
(1) hydrogen,
(2) aryl,
(3) aryl $C_{1-4}$alkyl,
(4) diaryl $C_{1-4}$alkyl,
(5) heteroaryl,
(6) heteroaryl $C_{1-4}$alkyl,
(7) $C_{3-10}$cycloalkyl, and
(8) substituted aryl substituted by one, two or three substituents independently selected from:
  (a) —SH,
  (b) —$SC_1$–$C_4$alkyl,
  (c) —CN,
  (d) —CO—$C_{1-8}$ alkyl,
  (e) —CO—aryl,
  (f) —$C_{1-8}$alkyl,
  (g) —$C_3$–$C_8$ cycloalkyl,
  (h) -aryl,
  (i) -heteroaryl,
  (j) —CO—heteroaryl,
  (k) —$C_{1-4}$alkyl-aryl,
  (l) —$CONR^6R^7$ where $R^6$ and $R^7$ are independently selected from:
    (i) H,
    (ii) $C_{1-8}$ alkyl,
    (iii) $C_{3-8}$ cycloalkyl,
    (iv) aryl,
    or $R^6$ and $R^7$ together with the nitrogen to which they are attached form a 5–7 membered saturated heterocyclic ring containing 1–2 nitrogen atoms, and 0–1 oxygen atoms;
  (m) —$NHCOR^6$,
  (n) —$OCOR^6$,
  (o) —$NR^6(CO)R^7$,
  (p) —$NR^6(CO)NHR^7$,
  (q) —$NHSO_2R^6$,
  (r) —$OR^6$,
  (s) —$NR^6R^7$,
  (t) —$CO_2R^6$, and
  (u) $C_xX_y$;

X is independently selected from F and Cl at each occurrence;

n is selected from 1 and 2;

x is an integer from 1 to 4;

y is 2x+1; and z is an integer from 3 to 5.

2. The compound of claim 1 wherein:

$R^1$ is selected from hydrogen and methyl;

$R^2$ is selected from:
(1) hydrogen,
(2) $CO_2R^4$,
(3) $CONR^4R^5$,
(4) 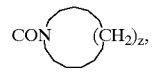

(5) $COR^5$,
(6) $S(O)_nR^5$,
(7) $NHCO_2R^4$,
(8) CN,
(9) $COSR^5$,
(10) methyl, and
(11) $C_xX_y$;

$R^3$ is selected from
(1) hydrogen,
(2) methyl,
(3) $CO_2R^4$,
(4) $CONR^4R^5$,
(5) $COR^5$,
(6) $S(O)_nR^5$,
(7) CN, and
(8) $C_xX_y$;

$R^4$ is selected from: hydrogen, and $C_{1-10}$ straight or branched-chain alkyl;

$R^5$ is selected from:
(1) hydrogen,
(2) aryl,
(3) aryl $C_{1-4}$alkyl,
(4) diaryl $C_{1-4}$alkyl,
(5) heteroaryl,
(6) heteroaryl $C_{1-4}$alkyl,
(7) $C_{3-10}$cycloalkyl, and
(8) substituted aryl substituted by one, two or three substituents independently selected from:
  (a) —$SC_1$–$C_4$alkyl,
  (b) —CN,
  (c) —CO—$C_{1-8}$ alkyl,
  (d) —CO—aryl,
  (e) —$C_{1-8}$alkyl,
  (f) —$C_3$–$C_8$ cycloalkyl,
  (g) -aryl,
  (h) -heteroaryl,
  (i) —CO—heteroaryl,
  (j) —$C_{1-4}$alkyl-aryl,
  (k) —$CONR^6R^7$ where $R^6$ and $R^7$ are independently selected from:
    (i) H,
    (ii) $C_{1-8}$ alkyl,
    (iii) $C_{3-8}$ cycloalkyl,
    (iv) aryl,
    or $R^6$ and $R^7$ together with the nitrogen to which they are attached form a 5–7 membered saturated heterocyclic ring containing 1–2 nitrogen atoms, and 0–1 oxygen atoms;
  (l) —$NHCOR^6$,
  (m) —$OCOR^6$,
  (n) —$NR^6(CO)R^7$,
  (o) —$NR^6(CO)NHR^7$,
  (p) —$NHSO_2R^6$,
  (q) —$OR^6$,
  (r) —$NR^6R^7$,
  (s) —$CO_2R^6$,
  (t) $C_xX_y$;

X is independently selected from F and Cl at each occurrence;

n is selected from 1 and 2;

x is an integer from 1 to 4;

y is 2x+1; and z is an integer from 3 to 5, or a pharmaceutically acceptable salt, ester or stereoisomer thereof.

3. The compound of claim 1 wherein:

$R^1$ is selected from hydrogen and methyl;

$R^2$ is selected from:
  (1) hydrogen,
  (2) $CO_2R^4$,
  (3) $CONR^4R^5$,
  (4)

CON⟨(CH2)z⟩, (5) $COR^5$,
  (6) $S(O)_nR^5$,
  (7) $NHCO_2R^4$,
  (8) $NHCOR^4$,
  (9) $NHCOR^5$,
  (10) CN,
  (11) $COSR^5$, and
  (12) $CF_3$;

$R^3$ is selected from:
  (1) hydrogen,
  (2) $CO_2R^4$,
  (3) $CONR^4R^5$,
  (4) $COR^5$,
  (5) $S(O)_nR^5$,
  (6) CN, and
  (7) $CF_3$;

$R^4$ is selected from: hydrogen, and $C_{1-10}$ straight or branched-chain alkyl;

$R^5$ is selected from:
  (1) hydrogen,
  (2) aryl,
  (3) aryl $C_{1-4}$alkyl,
  (4) diphenylmethyl,
  (5) heteroaryl,
  (6) heteroaryl $C_{1-4}$alkyl,
  (7) $C_{3-10}$cycloalkyl, and
  (8) substituted aryl substituted by one, two or three substituents independently selected from:
    (a) —$SC_1$–$C_4$alkyl,
    (b) —CN,
    (c) —CO—$C_{1-8}$ alkyl,
    (d) —CO—aryl,
    (e) —$C_{1-8}$alkyl,
    (f) —$C_3$–$C_8$ cycloalkyl,
    (g) -aryl,
    (h) -heteroaryl,
    (i) —CO—heteroaryl,
    (j) —$C_{1-4}$alkyl-aryl,
    (k) —$CONR^6R^7$ where $R^6$ and $R^7$ are independently selected from:
      (i) H,
      (ii) $C_{1-8}$ alkyl,
      (iii) $C_{3-8}$ cycloalkyl,
      (iv) aryl,
      or $R^6$ and $R^7$ together with the nitrogen to which they are attached form a 5–7 membered saturated heterocyclic ring containing 1–2 nitrogen atoms, and 0–1 oxygen atoms;
    (l) —$NHCOR^6$,
    (m) —$OCOR^6$,
    (n) —$NR^6(CO)R^7$,
    (o) —$NR^6(CO)NHR^7$,
    (p) —$NHSO_2R^6$,
    (q) —$OR^6$,
    (r) —$NR^6R^7$,
    (s) —$CO_2R^6$,
    (t) $C_xX_y$;

X is independently selected from F and Cl at each occurrence;

n is selected from 1 and 2;

x is an integer from 1 to 4;

y is 2x+1; and z is an integer from 3 to 5, or a pharmaceutically acceptable salt, ester or stereoisomer thereof.

4. The compound according to claim 1 wherein "a", "b", and "d" each represent single bonds and "c" represents a double bond.

5. The compound of claim 4 of structural formula:

[structural formula of steroid-like compound with Me, H, $R_3$, $R_2$, $CH_3$, N, O substituents]

selected from:

| Compound | $R^2$ | $R^3$ | |
|---|---|---|---|
| 16a,b | —H | —H | |
| 14a–c | —(H) | —($CO_2CH_3$) | |
| 17a–c | —($CH_3$) | —($CO_2CH_2CH_3$) | |
| 15a,b | —(H) | —($SO_2Ph$) | |
| 15c | —($SO_2Ph$) | —(H) | |
| 18a,b | —$CO_2CH_2CH_3$ | —$CO_2CH_2CH_3$ | |
| 19a,b | —CN | —CN | |
| 23a,b | —(CN) | —($CF_3$) | |
| 19a–d | —($CO_2CH_2CH_3$) | —($CF_3$) | |
| 24a,b | —(COPh) | —($CF_3$) | Isomers A,B,C |
| 24a,b | —CO—Ph | —$CF_3$ | Isomer A |
| 24a,b | —CO—Ph | —$CF_3$ | Isomer B&C |
| 25a,b,c | 4-(trifluoromethyl)-phenyl-carbamoyl | —$CF_3$ | | wherein substituents enclosed in parentheses may be reversed and the $R^2$ substituent may appear at $R^3$ and the $R^3$ substituent may appear at $R^2$;

or a pharmaceutically acceptable salt, ester or stereoisomer thereof.

6. The compound of claim 4 of structural formula:

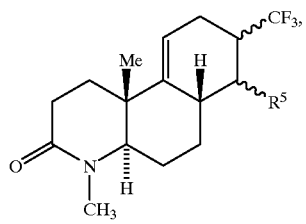

selected from:

| Compound | R² |
|---|---|
| 29a,b | —COS-(2-pyridyl) |
| 28a,b | —CO₂—C(CH₃)₃ |
| 27 | —CO₂CH₃ |
| 26a-c | —CO₂H |
| 32a,b | —CONHCH(Ph)₂ |
| 33a,b | —CONHCH₂CH(CH₃)₂ |
| 34a,b | —CO—N(pyrrolidinyl) |
| 35a,b | —CONH—C(CH₃)₃ |
| 36a,b | —CONH(CH₂)₄CH₃ |
| 31a,b | —CONH—(3-CF₂CF₃-phenyl) |
| 30a,b | —CONH—C(CH₃)₃ |
| 37a,b | —CONH—(3-C₂H₅-phenyl) |
| 38a,b | —CONH—(4-CF₃-phenyl) |
| 39a,b | —CONH—(3-CF₃-phenyl) |
| 40a,b | —CONH—(3-CCl₂Cl₃-phenyl) |
| 41a,b | —CONH—(4-CF₂CF₂CF₃-phenyl) |
| 42a,b | —CONH—(3-CF₂CF₂CF₃-phenyl) |
| 43a,b | —CONH—(3-CCl₂CCl₃-phenyl) |
| 44a,b | —CONH—phenyl |
| 45a,b | —CONH—(3-Ph-phenyl) |
| 46a,b | —CONH—(3-CF(CF₃)₂-phenyl) |
| 47a,b | —CON—(CH(CH₃)₂)₂ |
| 48a,b | —CONH—CH₂-cyclopropyl |
| 49a,b | —CONH-adamantyl |
| 50a,b | —CONHC(CH₃)₂CH₂C(CH₃)₃ | or a pharmaceutically acceptable salt, ester or stereoisomer thereof.

7. The compound according to claim 1 wherein "a" and "d" each represent single bonds and "b" and "c" each represent double bonds.

8. The compound of claim 1 of structural formula:

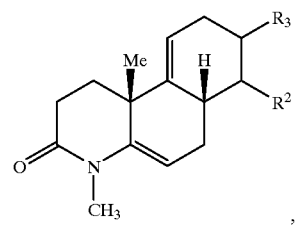

selected from:

| Compound | R² | R³ |
|---|---|---|
| 51a,b | —CO₂CH₂CH₃ | —CF₃ |
| 52a,b | —CONH—C₆H₄—C(CH₃)₂ | —CF₃ |
| 53 | —CO₂H | —CF₃ |
| 54 | —NHCO₂CH₂CH₃ | —CF₃ |
| 55 | CONH—C₆H₄—C(CH₃)₃ | —CF₃ |
| 56 | —CONHC(CH₃)₂CH₂C(CH₃)₃ | —CF₃ |
| 57 | —CONHC(CH₃)₃ | —CF₃ | or a pharmaceutically acceptable salt, ester or stereoisomer thereof.

9. The compound according to claim 1 wherein "a", "b", c and "d" each represent single bonds.

10. The compound of claim 9 of structural formula:

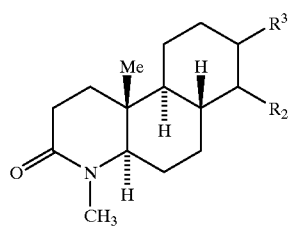

selected from:

| Compound | R² | R³ |
|---|---|---|
| 60 | —CONH—C₆H₅ | —CF₃ |
| 59 | —CO₂H | —CF₃ |
| 58 | —CO₂CH₃ | —CF₃ |
| 61 | —CONH—C₆H₄—C₂F₅ | —CF₃ |
| 68 | —CONHC(CH₃)₃ | —CF₃ |
| 69 | —CONHC(CH₃)₃ | —CF₃ |
| 67 | —NHCO₂CH₂CH₃ | —CF₃ |
| 64 | —CONH—C₆H₄—CH₂CH₃ | —CF₃ |

-continued

| Compound | R² | R³ |
|---|---|---|
| 65 | —CONH—C₆H₄—C(CH₃)₃ | —CF₃ |
| 66 | —CO—O—C₆H₅ | —CF₃ |
| 62 | —CO₂CH₂CH₃ | —CF₃ |
| 63 | —CO₂H | —CF₃ |
| 70 | —CONHC(CH₃)₂CH₂C(CH₃)₃ | —CF₃, | or a pharmaceutically acceptable salt, ester or stereoisomer thereof.

11. The compound according to claim 1 wherein "a" and "b" each represent single bonds and "c" and "d" each represent double bonds.

12. The compound of claim 11 of structural formula:

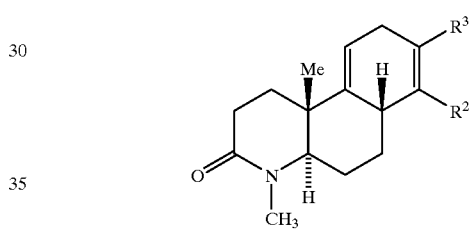

selected from:

| Compound | R² | R³ |
|---|---|---|
| 21a–c | —CO₂CH₂CH₃ | —CF₃ |
| 20a,b | —CF₃ | —CF₃ |
| 79a–c | —CO₂H | —CF₃ |
| 80a–c | —CONH—C₆H₄—C(CH₃)₃ | —CF₃ |
| 81a–c | —CONHC(CH₃)₃ | —CF₃ |
| 82a–c | —CONHC(CH₃)₂CH₂C(CH₃)₃ | —CF₃ |
| 83a–c | —CONH—C₆H₅ | —CF₃ |
| 84a–c | —CONH—C₆H₄—CF₂CF₃ | —CF₃ |

-continued

| Compound | R² | R³ |
|---|---|---|
| 85a–c | —CONH—(3-CF₂CF₂CF₃-phenyl) | —CF₃ |
| 86a–c | —CONH—(3-CF₂CCl₃-phenyl) | —CF₃ |
| 87a–c | —CONH—(3-C₂H₅-phenyl) | —CF₃ | or a pharmaceutically acceptable salt, ester or stereoisomer thereof.

13. The compound of claim 1 wherein "b", "c", and "d" each represent single bonds and "a" represents a double bond.

14. The compound of claim 13 of structural formula:

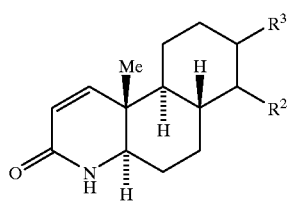

which is:

| Compound | R² | R³ |
|---|---|---|
| 71 | —CO₂CH₂CH₃ | —CF₃ |
| 88 | —CO₂H | —CF₃ |
| 89 | —CONH—(3-C(CH₃)₃-phenyl) | —CF₃ |
| 90 | —CONHC(CH₃)₃ | —CF₃ |
| 91 | —CONHC(CH₃)₂CH₂C(CH₃)₃ | —CF₃ |
| 92 | —CONH—phenyl | —CF₃ |
| 93 | —CONH—(3-CF₂CF₃-phenyl) | —CF₃ |

-continued

| Compound | R² | R³ |
|---|---|---|
| 94 | —CONH—(3-CF₂CF₂CF₃-phenyl) | —CF₃ |
| 95 | —CONH—(3-CF₂CCl₃-phenyl) | —CF₃ |
| 96 | —CONH—(3-C₂H₅-phenyl) | —CF₃ |

15. A compound of structural formula (II) having the nonsteroidal trans-anti-trans absolute configuration at the A,B and B,C ring junctures:

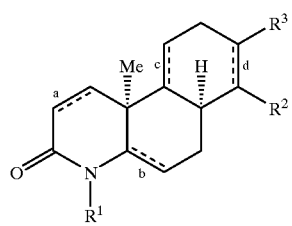

(II)

or a pharmaceutically acceptable salt, ester, or stereoisomer thereof.

16. The compound of claim 15 wherein:
R¹ is selected from hydrogen and methyl;
R² is selected from:
(1) hydrogen,
(2) CO₂R⁴,
(3) CONR⁴R⁵,
(4)

(5) COR⁵,
(6) S(O)ₙR⁵,
(7) NHCO₂R⁴,
(8) CN,
(9) COSR⁵,
(10) methyl, and
(11) CₓXᵧ;
R³ is selected from
(1) hydrogen,
(2) methyl,
(3) CO₂R⁴,
(4) CONR⁴R⁵,
(5) COR⁵,
(6) S(O)ₙR⁵,
(7) CN, and (8) $C_xX_y$;

$R^4$ is selected from: hydrogen, and $C_{1-10}$ straight or branched-chain alkyl;

$R^5$ is selected from:
(1) hydrogen,
(2) aryl,
(3) aryl $C_{1-4}$alkyl,
(4) diaryl $C_{1-4}$alkyl,
(5) heteroaryl,
(6) heteroaryl $C_{1-4}$alkyl,
(7) $C_{3-10}$cycloalkyl, and
(8) substituted aryl substituted by one, two or three substituents independently selected from:
  (a) —$SC_1$–$C_4$alkyl,
  (b) —CN,
  (c) —CO—$C_{1-8}$ alkyl,
  (d) —CO—aryl,
  (e) —$C_{1-8}$alkyl,
  (f) —$C_3$–$C_8$ cycloalkyl,
  (g) -aryl,
  (h) -heteroaryl,
  (i) —CO—heteroaryl,
  (j) —$C_{1-4}$alkyl-aryl,
  (k) —$CONR^6R^7$ where $R^6$ and $R^7$ are independently selected from:
    (i) H,
    (ii) $C_{1-8}$ alkyl,
    (iii) $C_{3-8}$ cycloalkyl,
    (iv) aryl,
    or $R^6$ and $R^7$ together with the nitrogen to which they are attached form a 5–7 membered saturated heterocyclic ring containing 1–2 nitrogen atoms, and 0–1 oxygen atoms;
  (l) —$NHCOR^6$,
  (m) —$OCOR^6$,
  (n) —$NR^6(CO)R^7$,
  (o) —$NR^6(CO)NHR^7$,
  (p) —$NHSO_2R^6$,
  (q) —$OR^6$,
  (r) —$NR^6R^7$,
  (s) —$CO_2R^6$,
  (t) $C_xX_y$;

X is independently selected from F and Cl at each occurrence;

n is selected from 1 and 2;

x is an integer from 1 to 4;

y is 2x+1; and z is an integer from 3 to 5, or a pharmaceutically acceptable salt, ester or stereoisomer thereof.

17. The compound of claim 15 wherein:

$R^1$ is selected from hydrogen and methyl;

$R^2$ is selected from:
(1) hydrogen,
(2) $CO_2R^4$,
(3) $CONR^4R^5$,
(4)

(5) $COR^5$,
(6) $S(O)_nR^5$,
(7) $NHCO_2R^4$,
(8) $NHCOR^4$,
(9) $NHCOR^5$,
(10) CN,
(11) $COSR^5$, and
(12) $CF_3$;

$R^3$ is selected from:
(1) hydrogen,
(2) $CO_2R^4$,
(3) $CONR^4R^5$,
(4) $COR^5$,
(5) $S(O)_nR^5$,
(6) CN, and
(7) $CF_3$;

$R^4$ is selected from: hydrogen, and $C_{1-10}$ straight or branched-chain alkyl;

$R^5$ is selected from:
(1) hydrogen,
(2) aryl,
(3) aryl $C_{1-4}$alkyl,
(4) diphenylmethyl,
(5) heteroaryl,
(6) heteroaryl $C_{1-4}$alkyl,
(7) $C_{3-10}$cycloalkyl, and
(8) substituted aryl substituted by one, two or three substituents independently selected from:
  (a) —$SC_1$–$C_4$alkyl,
  (b) —CN,
  (c) —CO—$C_{1-8}$ alkyl,
  (d) —CO—aryl,
  (e) —$C_{1-8}$alkyl,
  (f) —$C_3$–$C_8$ cycloalkyl,
  (g) -aryl,
  (h) -heteroaryl,
  (i) —CO—heteroaryl,
  (j) —$C_{1-4}$alkyl-aryl,
  (k) —$CONR^6R^7$ where $R^6$ and $R^7$ are independently selected from:
    (i) H,
    (ii) $C_{1-8}$ alkyl,
    (iii) $C_{3-8}$ cycloalkyl,
    (iv) aryl,
    or $R^6$ and $R^7$ together with the nitrogen to which they are attached form a 5–7 membered saturated heterocyclic ring containing 1–2 nitrogen atoms, and 0–1 oxygen atoms;
  (l) —$NHCOR^6$,
  (m) —$OCOR^6$,
  (n) —$NR^6(CO)R^7$,
  (o) —$NR^6(CO)NHR^7$,
  (p) —$NHSO_2R^6$,
  (q) —$OR^6$,
  (r) —$NR^6R^7$,
  (s) —$CO_2R^6$,
  (t) $C_xX_y$;

X is independently selected from F and Cl at each occurrence;

n is selected from 1 and 2;

x is an integer from 1 to 4;

y is 2x+1; and z is an integer from 3 to 5, or a pharmaceutically acceptable salt, ester or stereoisomer thereof.

18. The compound according to claim 15 wherein "a", "b", and "d" each represent single bonds and "c" represents a double bond.

19. The compound of claim 18 of structural formula:

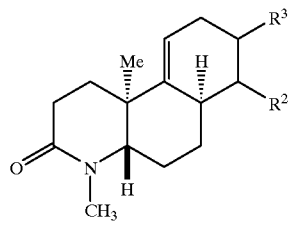

selected from:

| R² | R³ | |
|---|---|---|
| —H | —H | |
| —(H) | —(CO₂CH₃) | |
| —(CH₃) | —(CO₂CH₂CH₃) | |
| —(H) | —(SO₂Ph) | |
| —(SO₂Ph) | —(H) | |
| —CO₂CH₂CH₃ | —CO₂CH₂CH₃ | |
| —CN | —CN | |
| —(CN) | —(CF₃) | |
| —(CO₂CH₂CH₃) | —(CF₃) | |
| —(COPh) | —(CF₃) | Isomers A,B,C |
| —CO—Ph | —CF₃ | Isomer A |
| —CO—Ph | —CF₃ | Isomer B&C |
| 4—(trifluoro-methyl)-phenyl-carbamoyl | —CF₃ | | wherein substituents enclosed in parentheses may be reversed and the R² substituent may appear at R³ and the R³ substituent may appear at R².

20. The compound of claim 18 of structural formula:

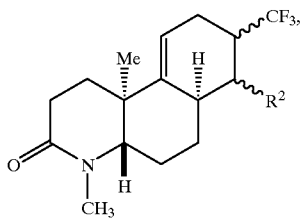

selected from:

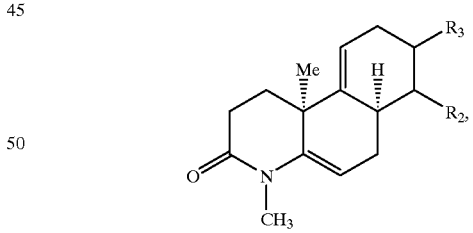

or a pharmaceutically acceptable salt, ester or stereoisomer thereof.

21. The compound according to claim 15 wherein "a" and "d" each represent single bonds and "b" and "c" each represent double bonds.

22. The compound of claim 15 of structural formula:

selected from:

| R² | R³ |
|---|---|
| —CO₂CH₂CH₃ | —CF₃ |
| | —CF₃ |

-continued

| R² | R³ |
|---|---|
| —CO₂H | —CF₃ |
| —NHCO₂CH₂CH₃ | —CF₃ |
| 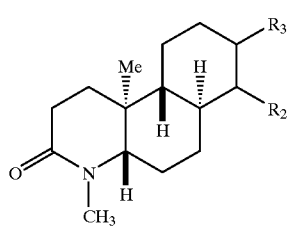 | —CF₃ |
| —CONHC(CH₃)₂CH₂C(CH₃)₃ | —CF₃ |
| —CONHC(CH₃)₃ | —CF₃ | or a pharmaceutically acceptable salt, ester or stereoisomer thereof.

23. The compound according to claim 15 wherein "a", "b", "c", and "d" each represent single bonds.

24. The compound of claim 23 of structural formula:

![structure]

selected from:

| R² | R³ |
|---|---|
| —CONH—⟨phenyl⟩ | —CF₃ |
| —CO₂H | —CF₃ |
| —CO₂CH₃ | —CF₃ |
| —CONH—⟨phenyl-C₂F₅⟩ | —CF₃ |
| —CONHC(CH₃)₃ | —CF₃ |
| —CONHC(CH₃)₃ | —CF₃ |
| —NHCO₂CH₂CH₃ | —CF₃ |
| —CONH—⟨phenyl-CH₂CH₃⟩ | —CF₃ |
| —CONH—⟨phenyl-C(CH₃)₃⟩ | —CF₃ |

-continued

| R² | R³ |
|---|---|
| 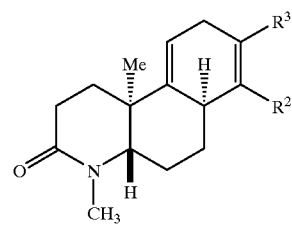 | —CF₃ |
| —CO₂CH₂CH₃ | —CF₃ |
| —CO₂H | —CF₃ |
| —CONHC(CH₃)₃ | —CF₃ |
| —CONHC(CH₃)₂CH₂C(CH₃)₃ | —CF₃, | or a pharmaceutically acceptable salt, ester or stereoisomer thereof.

25. The compound according to claim 15 wherein "a" and "b" each represent single bonds and "c" and "d" each represent double bonds.

26. The compound of claim 25 of structural formula:

![structure]

selected from:

| R² | R³ |
|---|---|
| —CO₂CH₂CH₃ | —CF₃ |
| —CF₃ | —CF₃ |
| —CO₂H | —CF₃ |
| —CONH—⟨phenyl-C(CH₃)₃⟩ | —CF₃ |
| —CONHC(CH₃)₃ | —CF₃ |
| —CONHC(CH₃)₂CH₂C(CH₃)₃ | —CF₃ |
| —CONH—⟨phenyl⟩ | —CF₃ |
| —CONH—⟨phenyl-CF₂CF₃⟩ | —CF₃ |
| —CONH—⟨phenyl-CF₂CF₂CF₃⟩ | —CF₃ |

-continued

| R² | R³ |
|---|---|
| 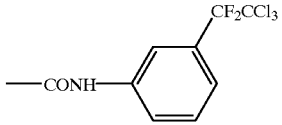 | —CF₃ |
| 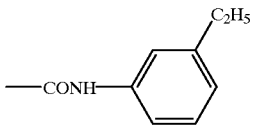 | —CF₃ | or a pharmaceutically acceptable salt, ester or stereoisomer thereof.

27. The compound of claim 15 wherein "b", c and "d" each represent single bonds and "a" represents a double bond.

28. The compound of claim 27 of structural formula:

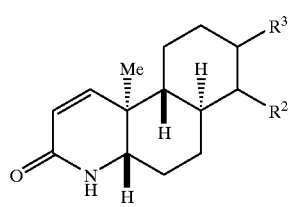

which is:

| R² | R³ |
|---|---|
| —CO₂CH₂CH₃ | —CF₃ |
| —CO₂H | —CF₃ |
| 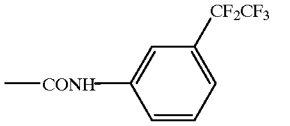 | —CF₃ |
| —CONHC(CH₃)₃ | —CF₃ |
| —CONHC(CH₃)₂CH₂C(CH₃)₃ | —CF₃ |
| 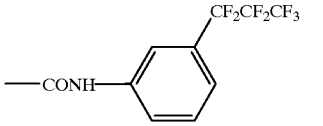 | —CF₃ |

-continued

| R² | R³ |
|---|---|
| 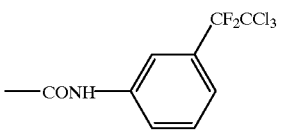 | —CF₃ |
| 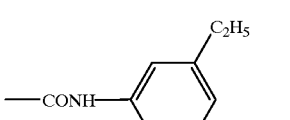 | —CF₃ |
| 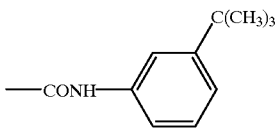 | —CF₃ |
| 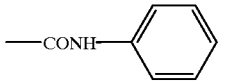 | —CF₃ |

29. A method of inhibiting 5α-reductase in a mammal, comprising the step of administering to a mammal in need of such inhibition a 5α-reductase inhibiting amount of a compound of claim 1.

30. A method for treating acne vulgaris, seborrhea, androgenic alopecia, female hirsutism, benign prostatic hyperplasia, prostatitis, apocrine gland sweating, hyperhidrosis and hydradenitis suppurativea, polycystic ovary syndrome, or prostatic cancer in a human by inhibiting 5α-reductase comprising the step of administering to a human in need of such treatment a 5α-reductase inhibiting amount of a compound of claim 1.

31. A pharmaceutical composition comprising a pharmaceutically acceptable carrier and a therapeutically effective amount of a compound of claim 1.

32. A method for treating acne vulgaris, seborrhea, androgenic alopecia, female hirsutism, benign prostatic hyperplasia, prostatitis, apocrine gland sweating, hyperhidrosis and hydradenitis suppurativea, polycystic ovary syndrome, or prostatic cancer in a human by inhibiting 5α-reductase comprising the step of administering to a human in need of such treatment a 5α-reductase inhibiting amount of a compound of claim 15.

* * * * *